(12) United States Patent
Kathirgamanathan

(10) Patent No.: US 10,439,147 B2
(45) Date of Patent: Oct. 8, 2019

(54) HETEROCYCLIC COMPOUNDS AND THEIR USE IN ELECTRO-OPTICAL OR OPTO-ELECTRONIC DEVICES

(71) Applicant: Power OLEDs Limited, London (GB)

(72) Inventor: Poopathy Kathirgamanathan, Middlesex (GB)

(73) Assignee: Power OLEDs Limited, London (GB)

( * ) Notice: Subject to any disclaimer, the term of this patent is extended or adjusted under 35 U.S.C. 154(b) by 237 days.

(21) Appl. No.: 14/879,979

(22) Filed: Oct. 9, 2015

(65) Prior Publication Data

US 2016/0035983 A1 Feb. 4, 2016
US 2018/0323378 A9 Nov. 8, 2018

Related U.S. Application Data

(63) Continuation-in-part of application No. PCT/GB2014/050970, filed on Mar. 27, 2014.

(30) Foreign Application Priority Data

Apr. 9, 2013 (GB) .................................. 1306365.6
Jul. 20, 2015 (GB) .................................. 1512720.2

(51) Int. Cl.
*H01L 51/54* (2006.01)
*H01L 51/00* (2006.01)
(Continued)

(52) U.S. Cl.
CPC ........ *H01L 51/0061* (2013.01); *C07D 339/08* (2013.01); *C07D 409/10* (2013.01);
(Continued)

(58) Field of Classification Search
CPC .... Y02E 10/549; C07F 7/0812; C07F 9/4028; C07F 9/5355; C07F 9/655372; C07F 15/00; C07F 15/002; C07F 15/0033; C07F 15/0086; C07D 279/24; C07D 279/26; C07D 339/00; C07D 339/08; C07D 409/00; C07D 409/12; C07D 409/14; C07D 417/00; C07D 417/10; H01L 51/0032;
(Continued)

(56) References Cited

U.S. PATENT DOCUMENTS 5,374,489 A 12/1994 Imai
7,879,462 B2 2/2011 Lyu
(Continued)

FOREIGN PATENT DOCUMENTS

CN 101976728 A 2/2011
EP 0562883 A2 9/1993
(Continued)

OTHER PUBLICATIONS

Machine translation of JP2005-314239. Date of publication: Nov. 10, 2005.*
Machine translation of JP2010-034548. Date of publication: Feb. 12, 2010.*
PCT/GB2014/050970, International Search Report and Written Opinion, dated Jan. 9, 2015, 17 pgs.
Ahn, Y., et al., "Electroluminescence Characteristic of a New Green-Emitting Phenylphenothiazine Dreivative with Phenylbenzimidazole Substituent", Bull. Korean Chem. Soc., 34, (2013), 107-111.
Lovell, J.M., et al., "Convenient Synthesis of 1,8-Diiodoanthracene and Its Coupling with Thianthrene Boronic Acids", Synthetic Communications, 27, abstract only, (1997), 1 pg.
Lovell, J.M., et al., "Synthesis of 1- and 2-substituted thianthrenes", J. Chem. Soc., Perkin Trans., 1, (1996), 2391-2395.
Swist, A., et al., "Thianthrene-based oligomers as hole transporting materials", ARKIVOC, (iii), (2012), 193-209.
PCT/GB2014/050970, International Preliminary Report on Patentability, dated Oct. 22, 2015, 12 pgs.
"United Kingdom Application Serial No. GB1405474.6, Search Report dated May 27, 2014", 7 pgs.
"Chinese Application Serial No. 201480025560.0, Office Action dated Sep. 11, 2017", (w/ English Translation), 8 pgs.
"Chinese Application Serial No. 201480025560.0, Office Action dated Nov. 17, 2016", (w/ English Translation), 12 pgs.
(Continued)

*Primary Examiner* — Andrew K Bohaty
(74) *Attorney, Agent, or Firm* — Schwegman Lundberg & Woessner, P.A.

(57) ABSTRACT

Compounds exhibiting high hole mobility and/or high glass transition temperatures are provided which are of the formula $[Ar^1]_m[Ar^2]_n$ wherein:
m is an integer from 1-3 and n is an integer and may be 1 or 2;
$Ar^1$ represents a thianthrene residue having a linkage to $Ar^2$ at one or two positions selected from ring positions 1-4 and 5-8 and optionally mono-, bi- or poly-substituted with $C_1$-$C_4$-alkyl-, $C_1$-$C_4$-alkoxy-, fluoro, phenyl or biphenyl which in the case of phenyl or biphenyl may be further substituted with $C_1$-$C_4$-alkyl-, $C_1$-$C_4$-alkoxy- or fluoro;
$Ar^2$ represents a residue derived from an arylamine in which the aryl rings are phenyl, naphthyl or anthracenyl optionally substituted with $C_1$-$C_4$-alkyl-, $C_1$-$C_4$-alkoxy- or fluoro, a polycyclic fused or chain aromatic ring system optionally containing nitrogen or sulphur and in a chain aromatic ring system optionally containing one or more chain oxygen or sulphur atoms, a triarylphosphine oxide or an arylsilane the rings of any of which are optionally substituted with $C_1$-$C_4$-alkyl-, $C_1$-$C_4$-alkoxy- or fluoro.
Certain of the compounds may be used in electron transport layers and may be doped with p-type dopants. They may be incorporated into OLEDs, organic photovoltaic devices, imaging members and thin film transistors.
In further embodiments there are provided OLEDs or other devices e.g. electrostatic latent image forming members in which improved efficiency is obtained by using as electron transport layers, electron injectors, hosts and emitters (dopants) ambipolar or electron-transmitting compounds in which thianthrene is bonded to aryl e.g. 1-anthracenyl-9-yl-thianthrene, 1-biphenyl-4-yl-thianthrene and 9,10-Bis(1-thianthrenyl) anthracene.

14 Claims, 12 Drawing Sheets

(51) Int. Cl.
    *H01L 51/50*      (2006.01)
    *C07D 339/08*     (2006.01)
    *C07D 409/10*     (2006.01)
(52) U.S. Cl.
    CPC ...... H01L 51/0074 (2013.01); H01L 51/5012 (2013.01); H01L 51/5072 (2013.01); *H01L 51/0072* (2013.01); *H01L 51/5056* (2013.01); *H01L 51/5088* (2013.01); *H01L 2251/301* (2013.01)
(58) Field of Classification Search
    CPC ............... H01L 51/005; H01L 51/0052; H01L 51/0059; H01L 51/0061; H01L 51/0071; H01L 51/0072; H01L 51/0074; H01L 51/50; H01L 51/5012; H01L 51/5016; H01L 51/5056; H01L 51/5072; H01L 51/5088; H01L 51/5096
    USPC ....... 428/690, 691, 917, 411.4, 336; 427/58, 427/66; 313/500–512; 257/40, 88–104, 257/E51.001–E51.052; 252/301.16–301.35
    See application file for complete search history.

(56)         References Cited

U.S. PATENT DOCUMENTS

| 8,012,606 | B2 | 9/2011 | Kai et al. | |
|---|---|---|---|---|
| 2006/0246317 | A1 | 11/2006 | Lyu et al. | |
| 2007/0138953 | A1* | 6/2007 | Tobise | H01L 51/5048 313/506 |
| 2007/0224446 | A1* | 9/2007 | Nakano | C09K 11/06 428/690 |
| 2007/0278938 | A1* | 12/2007 | Yabunouchi | C07D 307/91 313/504 |
| 2007/0290610 | A1 | 12/2007 | Park et al. | |
| 2009/0153031 | A1 | 6/2009 | Kai et al. | |
| 2011/0006295 | A1* | 1/2011 | Kathirgamanathan | C07D 215/04 257/40 |
| 2012/0085997 | A1 | 4/2012 | Sugita et al. | |
| 2012/0326141 | A1* | 12/2012 | Pflumm | C09K 11/06 257/40 |
| 2013/0175507 | A1 | 7/2013 | Ma | |
| 2013/0241401 | A1 | 9/2013 | Kwong et al. | |
| 2014/0077175 | A1 | 3/2014 | Jung et al. | |
| 2015/0162542 | A1 | 6/2015 | Ryu et al. | |
| 2015/0280133 | A1 | 10/2015 | Parham | |

FOREIGN PATENT DOCUMENTS

| JP | 06-220447 A | 8/1994 |
|---|---|---|
| JP | 200-63335 A | 2/2000 |
| JP | 2000-63335 A | 2/2000 |
| JP | 2000-186066 A | 7/2000 |
| JP | 2000-327640 A | 11/2000 |
| JP | 2001-039934 A | 2/2001 |
| JP | 2001-226331 A | 8/2001 |
| JP | 2005-314239 | 11/2005 |
| JP | 2005314239 A * | 11/2005 |
| JP | 2006-306870 A | 11/2006 |
| JP | 2009-196919 A | 9/2009 |
| JP | 2009-267255 A | 11/2009 |
| JP | 2010034548 A * | 2/2010 |
| JP | 2010-507224 A | 3/2010 |
| JP | 2011-523184 A | 8/2011 |
| JP | 2011-178742 A | 9/2011 |
| JP | 2012-500235 A | 1/2012 |
| JP | 2012-507590 A | 3/2012 |
| WO | WO-2007/015412 A1 | 2/2007 |
| WO | WO-2008/012581 A2 | 1/2008 |
| WO | WO-2009/149860 A2 | 12/2009 |
| WO | WO-2010/002848 A1 | 1/2010 |
| WO | WO-2010/020352 A1 | 2/2010 |
| WO | WO-2010/050779 A1 | 5/2010 |
| WO | WO-2011021803 A2 | 2/2011 |
| WO | WO-2011/081451 A2 | 7/2011 |
| WO | WO-2011110262 A1 * | 9/2011 ............ C09K 11/06 |
| WO | WO-2012093852 A2 | 7/2012 |
| WO | WO-2012/141393 A1 | 10/2012 |
| WO | WO-2013009032 A2 | 1/2013 |
| WO | WO-2014030822 A1 | 2/2014 |
| WO | WO-2014/067614 A1 | 5/2014 |
| WO | WO-2014/167286 A2 | 10/2014 |
| WO | WO-2014167286 A2 | 10/2014 |
| WO | WO-2015/080182 A1 | 6/2015 |

OTHER PUBLICATIONS

"International Application Serial No. PCT/GB2016/052176, International Preliminary Report on Patentability dated Jan. 23, 2018", 8 pgs.
"International Application Serial No. PCT/GB2016/052176, International Search Report dated Sep. 6, 2016", 5 pgs.
"International Application Serial No. PCT/GB2016/052176, Written Opinion dated Sep. 6, 2016", 6 pgs.
"Japanese Application Serial No. 2016-507045, Office Action dated Dec. 26, 2017", (w/ English Translation), 26 pgs.
"United Kingdom Appication Serial No. GB1405474.6, Examiniation Report dated Jun. 30, 2015", 3 pgs.
"United Kingdom Appication Serial No. GB1405474.6, Examiniation Report dated Sep. 15, 2014", 6 pgs.
"United Kingdom Appication Serial No. GB1405474.6, Response filed Jul. 14, 2014 to Search Report dated May 27, 2014", 272 pgs.
"United Kingdom Appication Serial No. GB1405474.6, Response filed Sep. 9, 2015 to Examiniation Report dated Jun. 30, 2015", 144 pgs.
"United Kingdom Appication Serial No. GB1405474.6, Response filed Oct. 31, 2014 to Examiniation Report dated Sep. 15, 2014", 189 pgs.
"United Kingdom Application Serial No. GB1512720.2, Search Report under Section 17(5) dated Feb. 24, 2017", 4 pgs.
Jang, Sang, et al., "Synthesis and device performances of phenothiazine based red phosphorescent host materials", *Journal of Industrial and Engineering Chemistry*, 17(3), (2011), 575-579.
Xu, Bingjia, et al., "Facile synthesis of a new class of aggregation-induced emission materials derived from triphenylethylene", *Journal of Materials Chemistry*, Issue 20, (2010), 4135-4141.

* cited by examiner

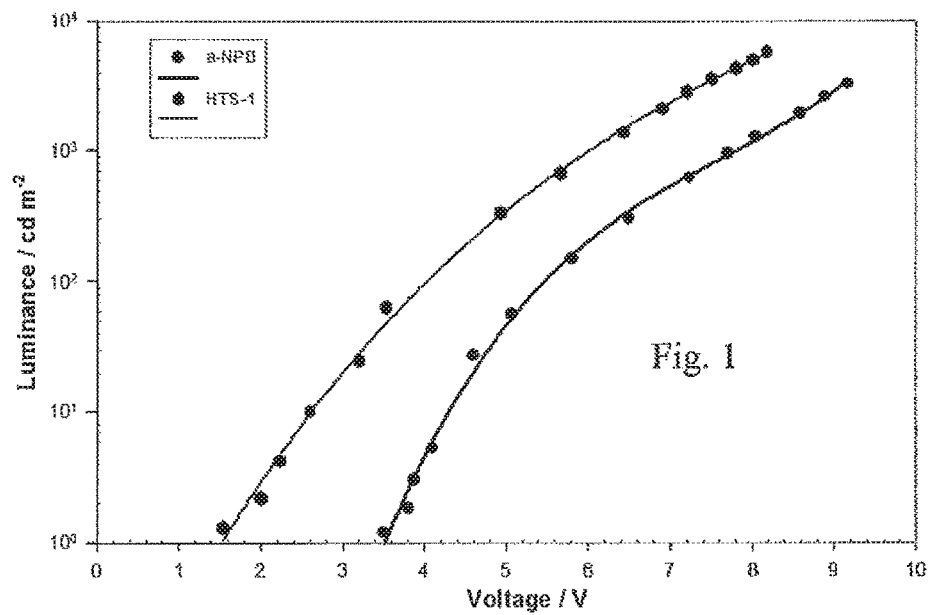
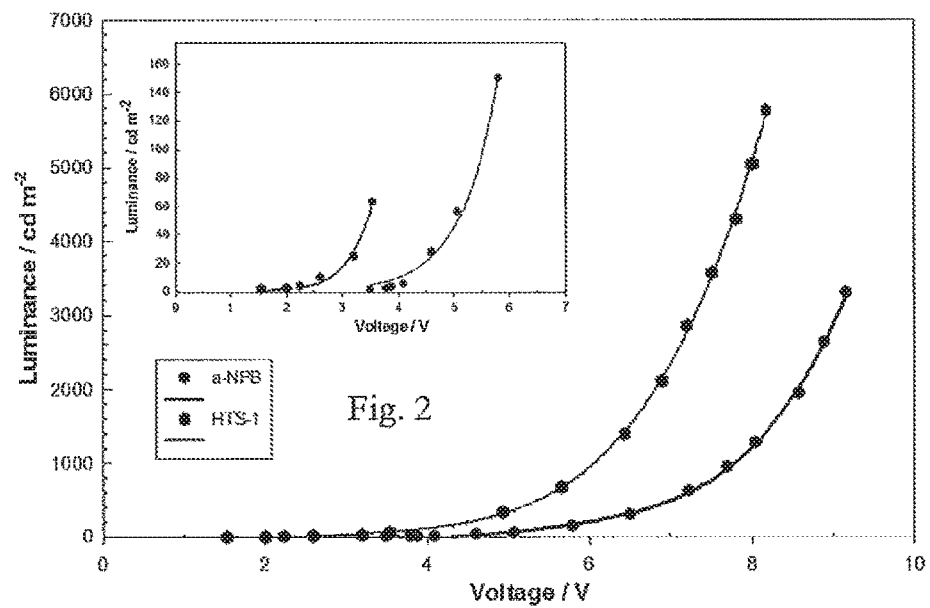

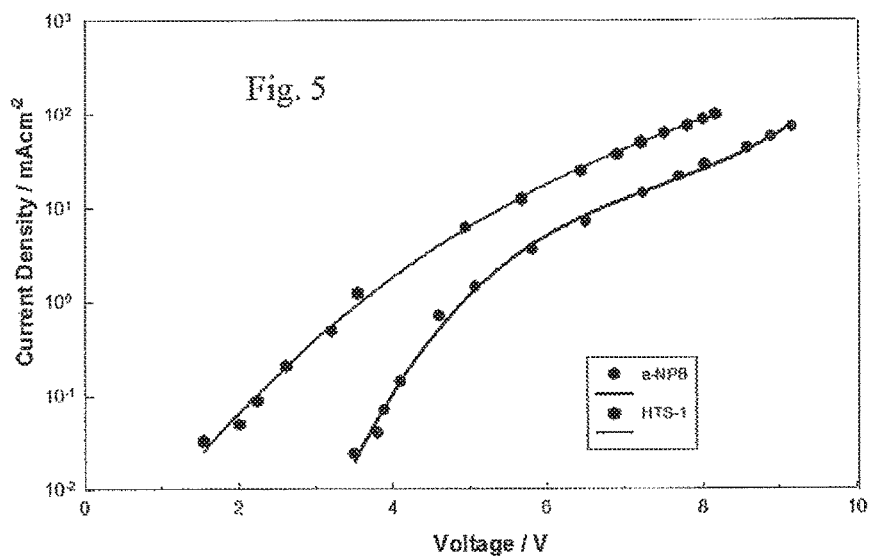
TO/ZnTp TP (E9363, 20 nm) /HTL(100 nm)/Alq3:DPQA(40:0.1 nm)/ Alq3 (20 nm)/Liq (6 nm)/Al
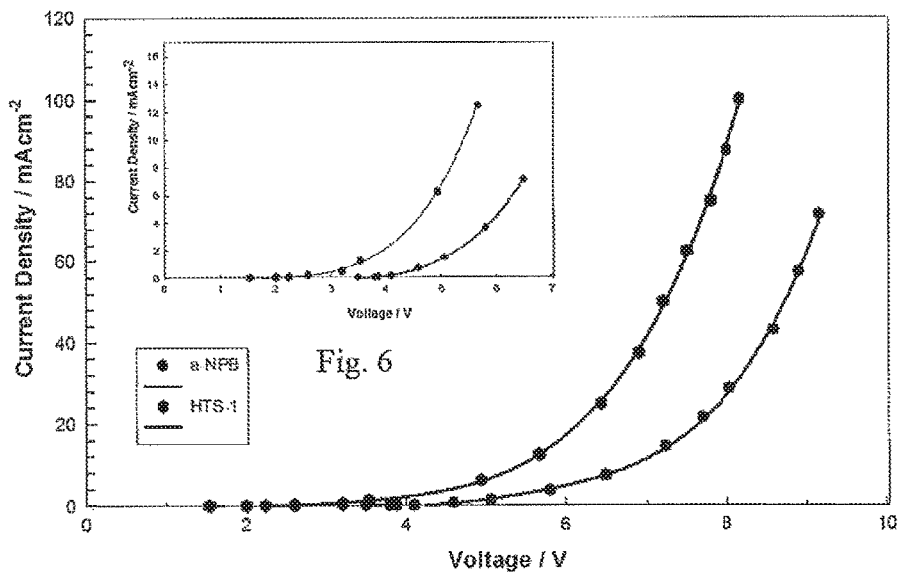
ITO/ZnTp TP (E9363, 20 nm) /HTL(100 nm)/Alq3:DPQA(40:0.1 nm)/ Alq3 (20 nm)/Liq (6 nm)/Al

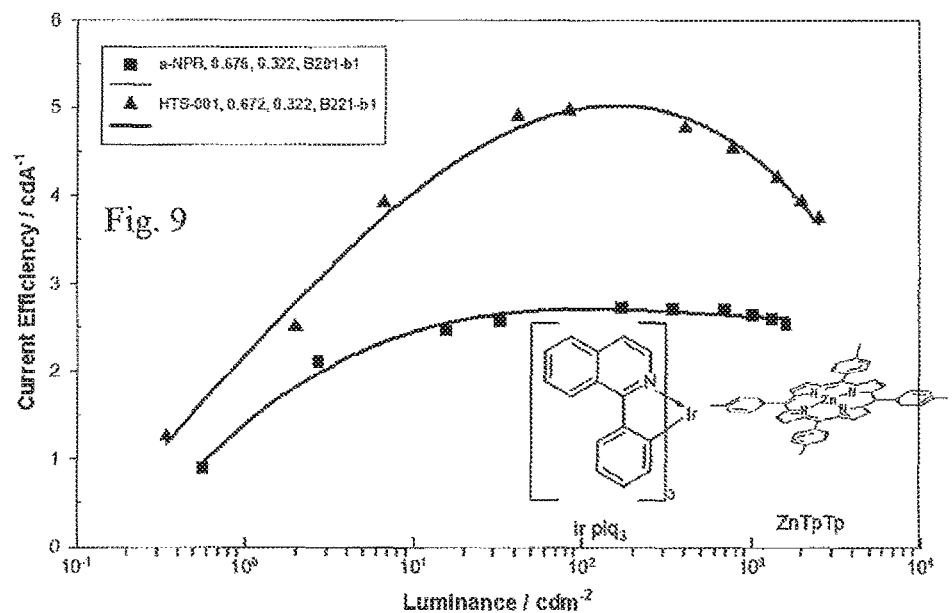
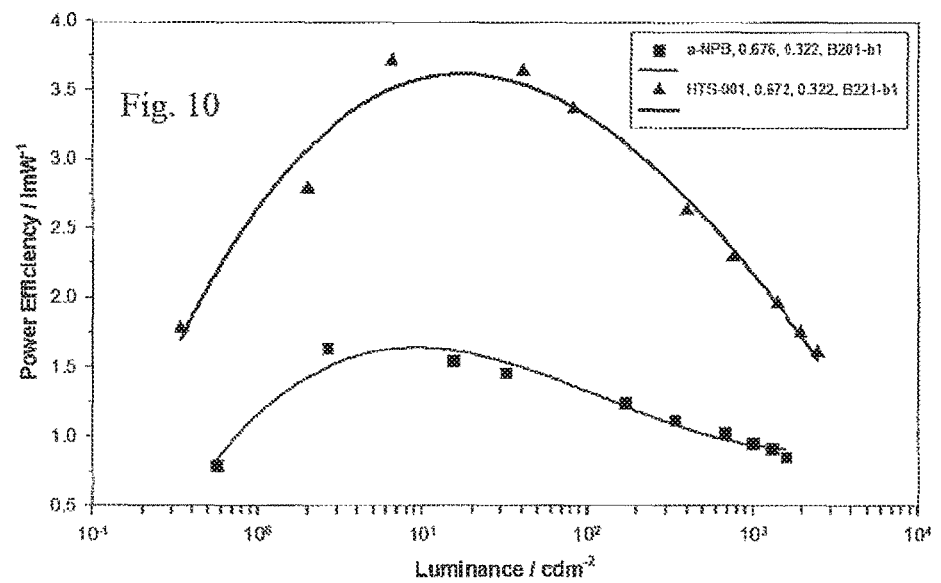

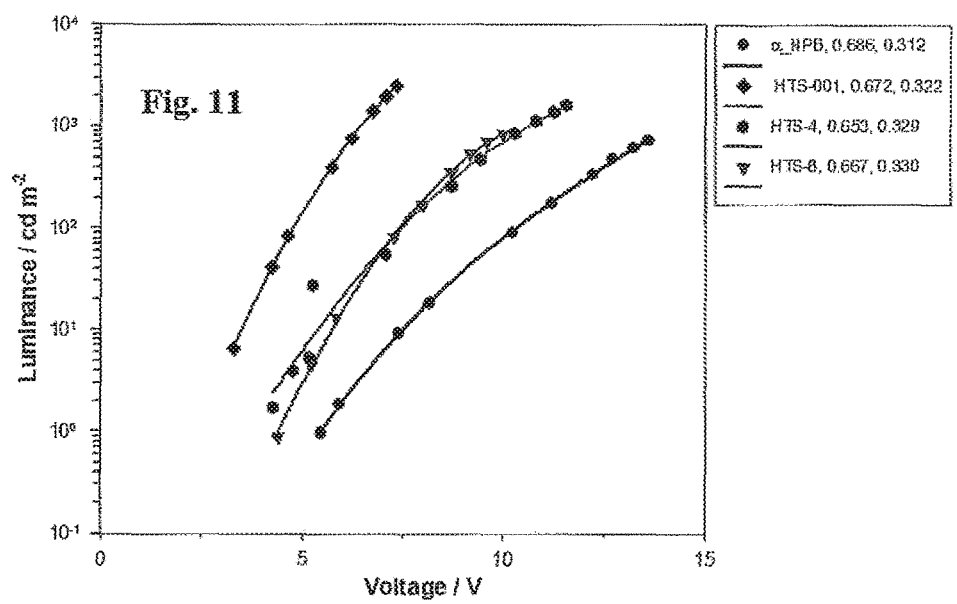
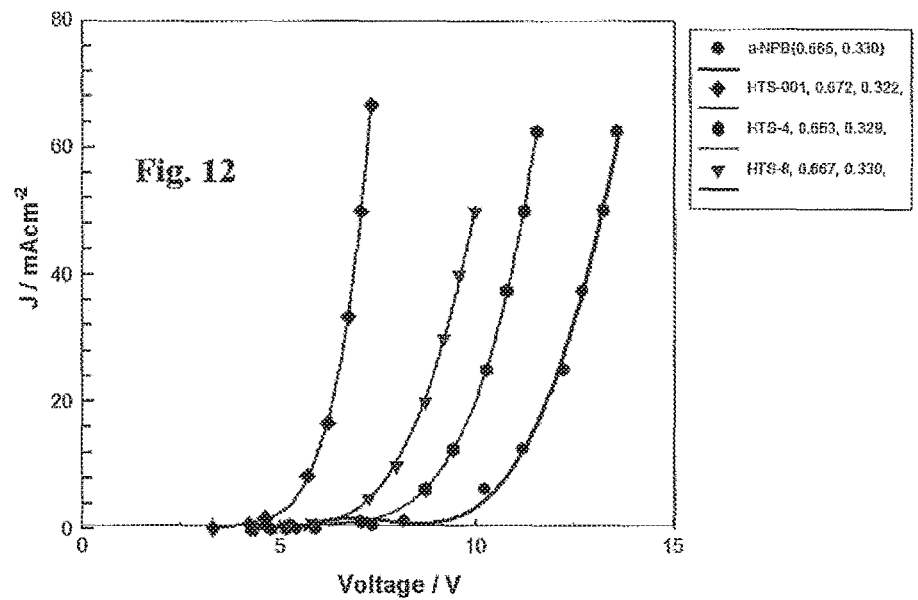

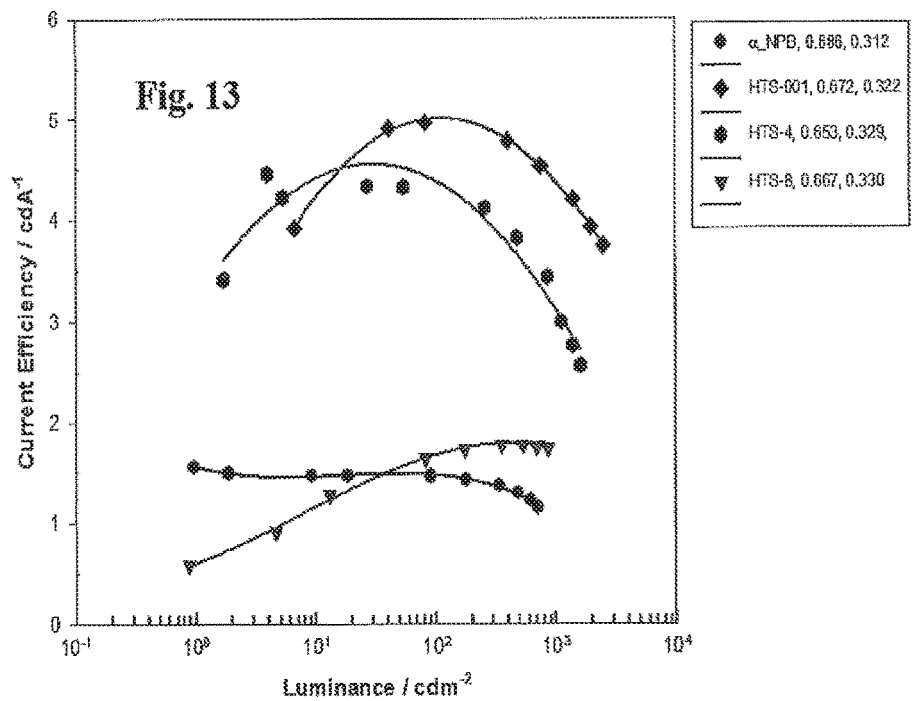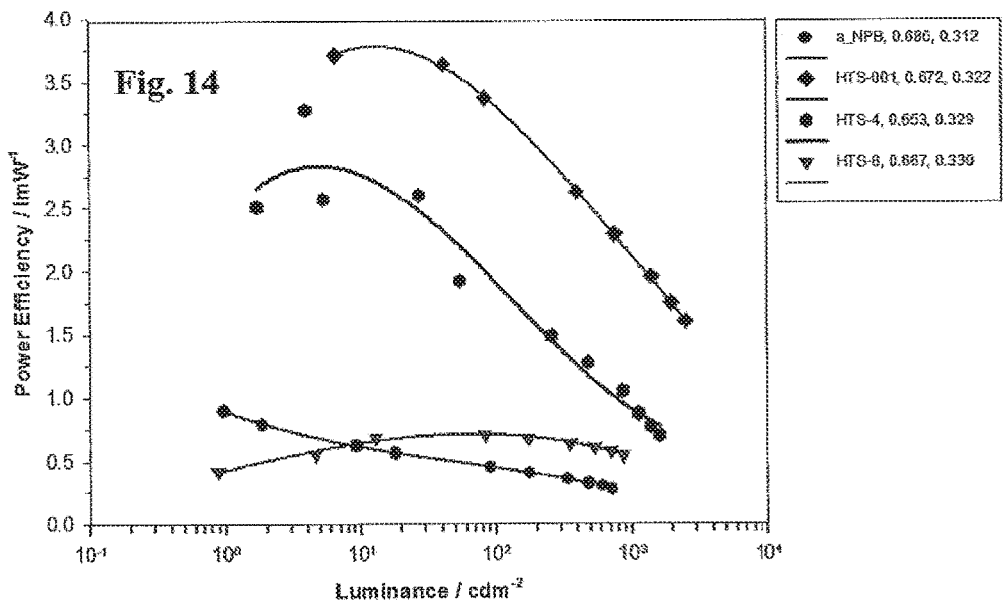

US 10,439,147 B2

HETEROCYCLIC COMPOUNDS AND THEIR USE IN ELECTRO-OPTICAL OR OPTO-ELECTRONIC DEVICES

CLAIM OF PRIORITY

This application is a continuation-in-part of and claims the benefit of priority under 35 U.S.C. § 120 to International Patent Application No. PCT/GB2014/050970, filed on Mar. 27, 2014, and which claims the benefit of priority under 35 U.S.C. § 119 to United Kingdom Patent Application No. 1306365.6, filed on Apr. 9, 2013, each of which are incorporated by reference herein in its entirety. This application also claims the benefit of priority under 35 U.S.C. § 119 to United Kingdom Patent Application No. 1512720.2, filed on Jul. 20, 2015, which is incorporated by reference herein in its entirety.

FIELD OF THE INVENTION

This invention relates to novel compounds and to their use in electro-optical or opto-electronic devices, inters alia optical light emitting devices, for example in a hole transport layer. It also relates to a second class of compounds having ambipolar properties. It further relates to novel compounds and to their use in electro-optical or opto-electronic devices, inter alia optical light emitting devices, for example in an electroluminescent device in the field of flat panel displays and lighting in an electron transport layer, hole blocking layer, host layer and emissive layer. The invention also relates to novel compounds which can be used as electron transporters in organic photovoltaics and semiconductors in thin film transistor devices.

BACKGROUND TO THE INVENTION

Hole Transport Materials

One class of hole transport materials comprises aromatic tertiary amines including at least two aromatic tertiary amine moieties (e.g. those based on biphenyl diamine or of a "starburst" configuration), of which the following are representative and of which at this time α-NPB (formula in the specific description below) is believed to be the most widely accepted and used in commercial production.

WO 2011/021803 (Duksan) discloses compounds having a thianthrene structure and their use in OLEDs. In examples, the five compounds below were synthesized.

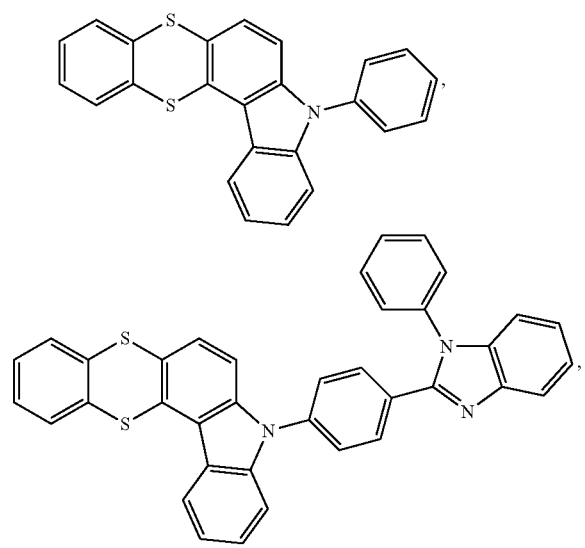

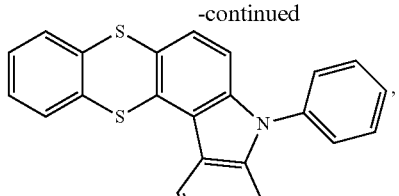

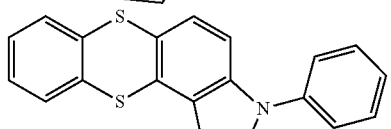

and

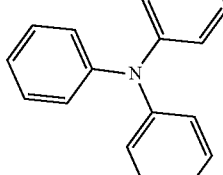

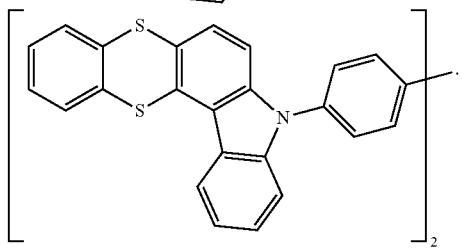

The above compounds were tested as host materials forming part of a doped electroluminescent layer in an OLED. A layer of 10 nm copper phthalocyanine on an ITO electrode had deposited thereon 30 nm of α-NPB (also known as α-NPD) as hole transporter, a layer of one of the above thianthrene compounds or of CBP to serve as host material for Ir(ppy)$_3$ as dopant, 10 nm of aluminium biphenoxy bis(2-methyl quinolate) as hole blocker, 40 nm of aluminium quinolate as electron transporter, 0.2 nm of lithium fluoride as electron injector and aluminium as cathode. Green electroluminescence with substantially the same colour coordinates was obtained when the test thianthrene compounds were used as host as when CBP was used as host, and turn-on voltage and luminous efficiency (cd/A) ranged from slightly worse than with CBP to somewhat better. However, the fused carbazole ring structures of the Duksan compounds exhibit relatively low hole mobility so that these compounds would be expected to exhibit poorbried performance if used as hole transporters. It should be mentioned that CBP, which also has carbazole rings linked directly to an extended aromatic system, has relatively low hole mobility and is also better as a host material in an electroluminescent layer than as a hole transport layer material. It is unsurprising, therefore, that Duksan employs a conventional hole transporter and does not employ any of the thianthrene compounds for that purpose.

Functionalised thianthrenes alleged to have hole transport properties and alleged to be blue emitters are disclosed by Swist et al., ARKIVOC 2012 (iii), 193-209 (2012). Suzuki coupling of thianthren-2-yl-2-boronic acid with a variety of brominated aromatic amino compounds having $C_4H_9$, $C_{12}H_{25}$ or $C_{16}H_{33}$ substituents gave oils or, in one instance, a solid of low melting point. Stille coupling of 2,8-dibromothianthrene with $(Bu)_3Sn$— derivatives of thiophene, oxazole, furan and pyridine gave 2,8-bis(2-oxazolyl) thianthrene which was an oil, 2,8-bis(2-thiophenyl) thianthrene m.p, 176-179° C., 2,8-bis(2-furanyl)thianthrene m.p. 204-206° C. and 2,8-bis(2-pyridyl)thianthrene (m.p. 113-114° C., all of which are undesirably low for device applications. Although the compounds were investigated by cyclic voltammetry, DPV spectroscopy, UV-Visible spectroscopy and fluorescence—were alleged to have band gaps in a range appropriate for semiconductors, no hole mobility measurements were made, and the compounds were not tested in OLEDs or other practical devices. They are alleged to be castable into uniform films, but this would not be a property shared by those compounds which are oils. There is no disclosure or suggestion that the materials reported, or any of them, should be used as hole transport layers in OLEDs as opposed to alternative devices such as organic photovoltaic devices, or that any of them give better properties in a hole transport layer of an OLED than established materials e.g. α-NPB and no reason to suppose that this is the case.

U.S. Pat. No. 8,012,606 (Takahiro et al, Nippon Steel) discloses heterocyclic compounds represented by the general formulae

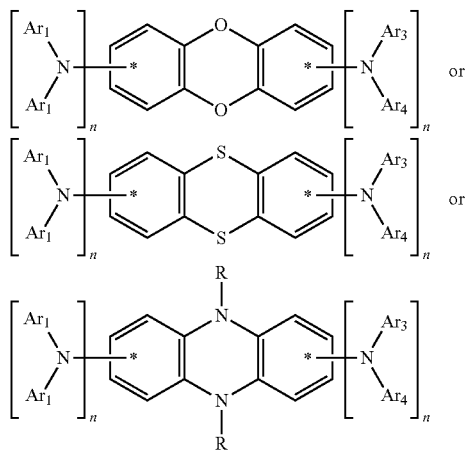

wherein: R represents a hydrogen atom, a substituted or unsubstituted alkyl group, or a substituted or unsubstituted aryl group, $Ar_1$, $Ar_2$, $Ar_3$, and $Ar_4$ denote independently a substituted or unsubstituted aryl group or $Ar_1$, $Ar_2$ together with the nitrogen atom bonded thereto or $Ar_3$, $Ar_4$ together with the nitrogen atom bonded thereto may form a nitrogen-containing hetero ring (e.g. N-carbazolyl, N-phenoxazinyl, N-phenothiazinyl), and m and n are independently 1 or 2. Examples disclose compounds as described above serving as components of the light-emissive layer of an OLED and in one instance as a hole transport layer. The compounds are alleged when applied to an organic EL device to enables the device to be driven at low voltage. When used as a host material, electrons and holes are alleged to move in a well-balanced way to form a wide range of emission of light and attain high luminous efficiency. Furthermore, the heterocyclic compounds have a high triplet energy which is important in an electroluminescent device utilizing phosphorescence. Hence, when used as a host material or an electron-transporting material for a phosphorescent device, the energy of the triplet excited state of a phosphorescent dopant can be confined efficiently and phosphorescence can be obtained at high efficiency. In addition to these good electrical properties, the said heterocyclic compounds are alleged to be stable when formed into thin film. An organic EL device comprising the heterocyclic compound of this invention in its organic layer efficiently emits light of high brightness at low voltage and shows excellent durability and it is applicable to flat panel displays Representative compounds include:
2,7-bis(phenylamino)dibenzodioxin,
2,7-bis(9-carbazolyl)dibenzodioxin,
2,7-bis(N-3-biphenylyl-N-phenylamino)dibenzodioxin,
2,7-bis(N-1-naphthyl-N-phenylamino)dibenzodioxin and
2,7-bis(9-carbazolyl) thianthrene Light Emission Materials that emit light when an electric current is passed through them are well known and used in a wide range of display applications. Devices which are based on inorganic semiconductor systems are widely used. However these suffer from the disadvantages of high energy consumption, high cost of manufacture, low quantum efficiency and the inability to make flat panel displays. Organic polymers have been proposed as useful in electroluminescent devices, but it is not possible to obtain pure colours; they are expensive to make and have a relatively low efficiency. Another electroluminescent compound which has been proposed is aluminium quinolate, but it requires dopants to be used to obtain a range of colours and has a relatively low efficiency.

Patent application WO 98/58037 describes a range of transition metal and lanthanide complexes which can be used in electroluminescent devices which have improved properties and give better results. Patent Applications WO 98/58307, WO 00/26323, WO 00/32719, WO 00/32717, WO 00/32718 and WO 00/44851 describe electroluminescent complexes, structures and devices using rare earth chelates. U.S. Pat. No. 5,128,587 discloses an electroluminescent device which consists of an organometallic complex of rare earth elements of the lanthanide series sandwiched between a transparent electrode of high work function and a second electrode of low work function, with a hole conducting layer interposed between the electroluminescent layer and the transparent high work function electrode, and an electron conducting layer interposed between the electroluminescent layer and the electron injecting low work function cathode. The hole conducting layer and the electron conducting layer are required to improve the working and the efficiency of the device. The hole transporting layer serves to transport holes and to block the electrons, thus preventing electrons from moving into the electrode without recombining with holes. The recombination of carriers therefore mainly takes place in the emissive layer.

JP 2005-314239 Mitsui Chemicals discloses compounds said to be suitable for incorporation into electroluminescent layers of OLED devices and having thianthrene bonded to anthracene. However, there is no disclosure or suggestion of the suitability of incorporating such compounds into an electron transport layer of such a device, and in exemplified cells the electron transport layer used was of well-known materials such as aluminium quinolate.

In order to enhance the performance of electroluminescent organometallic complexes the electroluminescent organometallic complex can be mixed with a host material and we have now devised an improved electroluminescent material using a metal quinolate as the host material.

Electron Transport Materials

Kulkarni et al., *Chem. Mater.* 2004, 16, 4556-4573 (the contents of which are incorporated herein by reference) have reviewed the literature concerning electron transport materials (ETMs) used to enhance the performance of organic light-emitting diodes (OLEDs). In addition to a large number of organic materials, they discuss metal chelates including aluminium quinolate, which they explain remains the most widely studied metal chelate owing to its superior properties such as high EA (~−3.0 eV; measured by the present applicants as −2.9 eV) and IP (~−5.95 eV; measured by the present applicants as about −5.7 eV), good thermal stability (Tg ~172° C.) and ready deposition of pinhole-free thin films by vacuum evaporation. Aluminium quinolate remains a preferred material both for use as a host to be doped with various fluorescent materials to provide an electroluminescent layer and for use as an electron transport layer. For a hole transporter or electron transporter to work effectively in a phosphorescent device, the triplet levels of the respective materials should be higher than the triplet level of the phosphorescent emitter.

SUMMARY OF THE INVENTION

A problem with which the invention is concerned is to provide further, or in the alternative improved, compounds having good hole transport properties when used in OLEDs and other electro-optic or opto-electronic devices. A further problem with which invention is concerned is to provide OLEDs of improved performance and lifetime e.g. by the linkage of nitrogen to a tricyclic ring structure not directly but via an aryl spacer group.

In one aspect the invention provides a compound of the formula [$Ar^1$]m[$Ar^2$]$_n$ wherein:

m is an integer from 1-3 and n is an integer and may be 1 or 2;

$Ar^1$ represents a thianthrene residue having a linkage to $Ar^2$ at one or two positions selected from ring positions 1-4, 2,7 and 6-9 optionally mono-, bi- or poly-substituted with $C_1$-$C_4$-alkyl-, $C_1$-$C_4$-alkoxy-, fluoro, phenyl or biphenyl which in the case of phenyl or biphenyl may be further substituted with $C_1$-$C_4$-alkyl-, $C_1$-$C_4$-alkoxy- or fluoro;

$Ar^2$ represents a residue derived from an arylamine in which the aryl rings are phenyl, naphthyl or anthracenyl optionally substituted with $C_1$-$C_4$-alkyl-, $C_1$-$C_4$-alkoxy- or fluoro and in which there is aryl between nitrogen and $Ar^1$, a polycyclic fused or chain aromatic ring system optionally containing nitrogen or sulphur and in a chain aromatic ring system optionally containing one or more chain oxygen or sulphur atoms, a triarylphosphine oxide or an arylsilane the rings of any of which are optionally substituted with $C_1$-$C_4$-alkyl-, $C_1$-$C_4$-alkoxy- or fluoro.

In such compounds, as explained above, $Ar^1$ represents thianthrene. In embodiments $Ar^1$ is linked to $Ar^2$ at the 1-position, at the 2-position, the 1- and 8-positions or the 2- and 7-positions.

In many embodiments $Ar^2$ represents a diarylamine residue the nitrogen of which is linked to $Ar^1$, and whose rings are optionally substituted $C_1$-$C_4$-alkyl-, $C_1$-$C_4$-alkoxy- or fluoro, phenyl, naphthyl, anthracenyl or phenylpyridyl. In other embodiments $Ar^2$ represents a triarylamine residue whose rings are optionally substituted $C_1$-$C_4$-alkyl-, $C_1$-$C_4$-alkoxy- or fluoro. In the diarylamine series e.g. diphenylamine, N-phenyl-1-naphthylamino, N-phenyl-2-naphthylamino or in the triarylamine series e.g. triphenylamine the rings may optionally be substituted with $C_1$-$C_4$-alkyl-, $C_1$-$C_4$-alkoxy- or fluoro. In the triarylamine series m may be 1, 2 or 3. In further embodiments $Ar^2$ represents carbazole, spiro-bicarbazole or dibenzothiophene residue optionally ring-substituted with $C_1$-$C_4$-alkyl-, $C_1$-$C_4$-alkoxy- or fluoro.

Embodiments of the above compounds are (a) of the formula

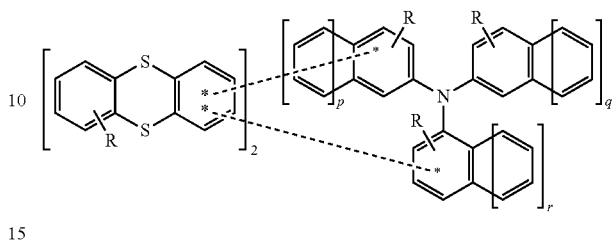

wherein:

linkages to the thianthrene rings may be at the 1- or 2-position;

linkages may be o- or p- to the phenyl or naphthyl rings to which they are attached;

p, q and r are independently 0 or 1; and the groups R which may be the same or different independently represent hydrogen or ring substituents selected from methyl, methoxy, ethyl, ethoxy, aryl (e.g. phenyl) and fluoro; or (b) of the formula

[$Ar^1$]m[$Ar^2$]$_n$ wherein m is 1 or 2 and n is 1;

$Ar^1$ represents thianthrene optionally mono-, bi- or poly-substituted with methyl, methoxy, ethyl, ethoxy or fluoro; and $Ar^2$ represents bis-triphenylamine optionally mono-, bi- or poly-substituted with methyl, methoxy, ethyl, ethoxy or fluoro, the groups $Ar^1$ each being bonded to $Ar^2$ at a phenyl ring, said substituted phenyl rings being bonded to the same or different nitrogen atoms;

(c) of the formula

[$Ar^1$]m[$Ar^2$]$_n$ wherein m is 1 or 2, n is 1;

$Ar^1$ represents thianthrene optionally mono-, bi- or poly-substituted with methyl, methoxy, ethyl, ethoxy, fluoro, phenyl or biphenyl which in the case of phenyl or biphenyl may be further substituted with methyl, methoxy, ethyl, ethoxy- or fluoro; and $Ar^2$ when m is 1 represents dibenzothiophene ring-substituted with tripehylmethyl and optionally further substituted with methyl, methoxy, ethyl, ethoxy- or fluoro and when m is 2 presents dibenzothiophene optionally ring-substituted with methyl, methoxy, ethyl, ethoxy or fluoro.

Embodiments of the present compounds exhibit a surprisingly favourable combination of hole mobility and high glass transition temperature or melting point, and the compounds also find utility in a hole injection layer and/or in an electron blocking layer. Since they are in general small molecules, many of them are purifiable by sublimation, which is desirable for the production of compounds of the purity required for OLEDs and other device applications. Embodiments of these compounds exhibit ambipolarity i.e they can be doped to form either electron or hole transport layers depending upon whether they are doped with p-type or n-type dopants. Such molecules are sought-after by device manufacturers because in some embodiments the number of different materials in different layers that have to be used is reduced.

HOMO and LUMO levels compared to α-NBP are shown in FIG. 22.

In a further aspect the invention provides the compounds 2-(4'-diphenylamino)phenyl-8-(1'-thianthrenyl)-dibenzothiophene and 4-(1-thianthrenyl)-bis(triphenylamine). As apparent in FIG. 17, these compounds have favourable physical properties including HOMO levels, LUMO levels and triplet levels.

Embodiments of the above compounds may be purified by sublimation. Their physical properties and those of related materials are summarised in the table below:

| Compound | α-NPB | HTS-4 | HTS-8 | HTS-10 | HTS-11 | HTS-13 |
|---|---|---|---|---|---|---|
| M.P/° C. | 279-283 | — | — | — | — | — |
| Tg/° C. | — | 122 | 135 | 96 | 124 | 107 |
| Td/° C. | — | 450 | 510 | 450 | 500 | 425 |
| Band gap/eV | 3.1 | 3.3 | 3.9 | 3.2 | 3.3 | 3.1 |

In a further aspect the invention provides a hole transport material comprising a heterotricyclic compound as defined above and a p-dopant which is an acceptor-type organic molecule. In some embodiments the dopant is present in an amount such that when the material is deposited to form a layer the dopant contributes about 10-40% to the layer thickness, e.g. about 33%. Other materials that may be present in the composition, in embodiments in minor amounts e.g. <50 wt % based on the weight of the heterotricyclic compound, include known organic hole transport agents e.g. an aromatic tertiary amine of biphenyl or starburst configuration, in some embodiments α-NPB.

In a further aspect the invention provides an optical light-emitting diode having first and second electrodes and between said electrodes a layer comprising a compound as defined above or a material as defined above. The layer may be a hole transport layer or a hole injection layer. The device may include an emissive layer comprising a fluorescent emitter, a phosphorescent emitter, an ion fluorescent (rare earth based) emitter or an optical light-emissive quantum dots. A hole injection layer may be provided comprising CuPC, ZnTpTP (zinc tetraphenylporphyrin), 2-TNATA, $MoO_3$, $MoO_x$, $WO_3$, $WO_x$, NiOx or hexacyanohexaazatriphenylene of structure

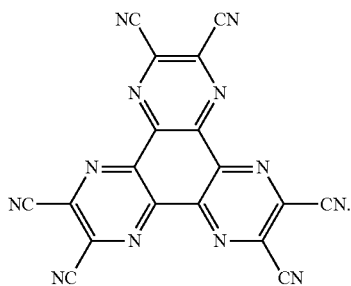 [SMILES: N#Cc1nc2c3nc(C#N)c(C#N)nc3c3nc(C#N)c(C#N)nc3c2nc1C#N]

The device may form part of a flat panel display or a lighting panel. Other end-uses may include organic photovoltaic devices, imaging members for forming an electrostatic latent image, organic thin film transistors and dye-sensitised solar cells.

A further problem with which the invention is concerned is to provide compounds which may be used in OLEDs as electron transport materials, electron injectors, hosts, hole blockers and emissive materials and in some embodiments materials emitting in the blue region of the electromagnetic spectrum.

That problem is solved, according to a further aspect of the invention, by compounds in which there is employed a compound in which thianthrene is bonded to polycyclic aryl, or a composition comprising a compound as aforesaid in admixture with a p-type dopant. Examples include the materials ETS-1, ETS-2 and ETS-3 described in the examples together with other materials discussed in relation to the electron transport layer of an OLED. The exemplified compounds, in particular, exhibit a surprisingly favourable combination of electron mobility and high glass transition temperature. Also, these compounds show intense fluorescence as thin films, powders and in solution, particularly in the blue and green region of the visible spectrum.

In a further aspect, the invention provides an electro-optical or opto-electronic device having a layer comprising of compounds described above and further discussed in relation to the electron transport layer. Such devices include OLED Displays, OLED Lighting and also e.g. organic thin film transistors, organic phototransistors, organic photovoltaic cells, organic photodetectors, electronic storage devices based on bistable organic molecules and photoconductive imaging members for creating electrostatic latent images.

In a yet further aspect the invention provides an optical light emitting diode device having a first electrode, a layer comprising any of the compounds in Table 1 or its derivatives and a second electrode. The layer is in an embodiment of an electron transport layer (either neat or doped with low work function metals or metal complexes) or an electron injecting layer or host or emissive layer (host or dopant along with another dopant or host respectively).

The same layer can also act as a hole blocking layer.

It will be appreciated that OLEDs according to the invention may have the aforesaid thianthrene compounds in both the hole and in the electron transport layers or in the hole transport layer, in the electroluminescent layer and in the electron transport layer.

In a further aspect there is provided an OLED having a compound having one or two thianthrene moieties linked to conjugated or aromatic hydrocarbon other than alkyl-substituted fluorene. The OLED may incorporate a compound which is of one of the formulae set out below, X and Y being S:

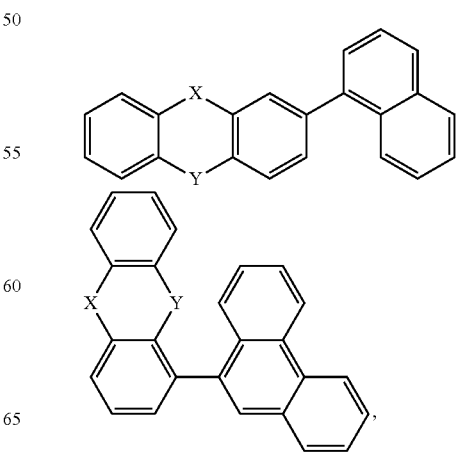

-continued

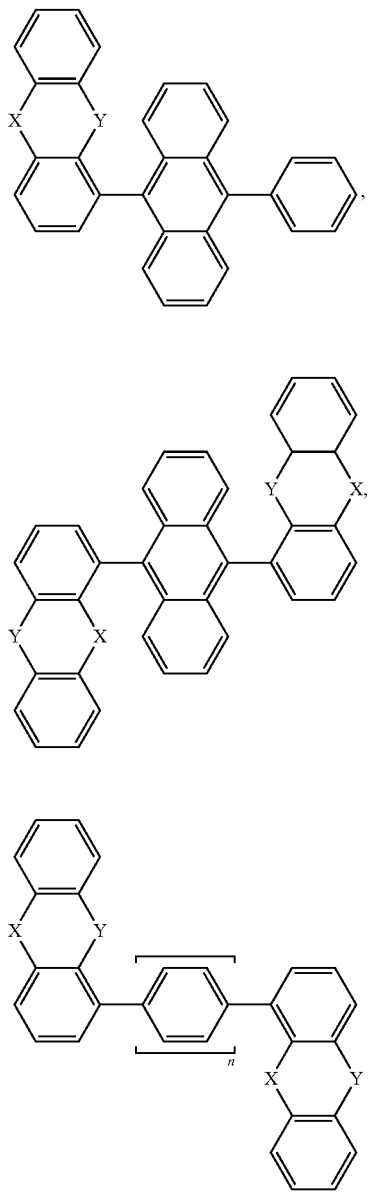

(wherein n is an integer and refers to a polyphenyl chain or fused rings),

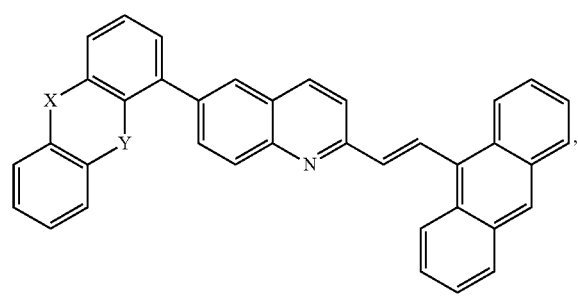

1-phenyl-2-(4-(thianthren-9-yl)phenyl)-1H-benzo[d]imidazole,

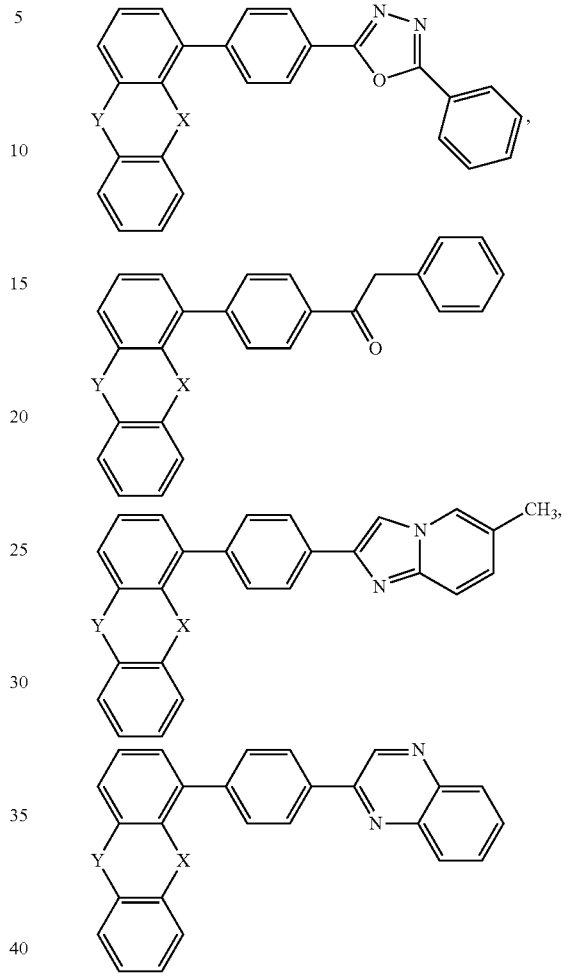

wherein X and Y are both S, the rings optionally being substituted e.g. with methyl.

The compound may be 1-anthracenyl-9-yl-thianthrene, 1-biphenyl-4-yl-thianthrene or 9,10-Bis (1-thianthrenyl) anthrance or a mixture thereof. It may be mixed with a low work function metal complex or may be doped with a fluorescent dopant or may be doped with a phosphorescent dopant or may be doped with a rare earth chelate. For example, the compound may be mixed with either lithium quinolinolate (LiQ) or its derivatives (e.g. having one or two ring $C_1$-$C_4$ alkyl substituents e.g. methyl or t-butyl) or Lithium Schiff base complexes from 1 to 99% by mass, e.g. 10 to 90% by mass, e.g. 20-90% by mass, commonly 30-80% by mass. Specific substituted quinolinolates that may be used include lithium 2-methyl-8-quinolinate, lithium 3-methyl-8-quinolinate, lithium 4-methyl-8-quinolinate, lithium 2,3 dimethyl-8-quinolinate, lithium 2,5 dimethyl-8-quinolinate, lithium 4,5 dimethyl-8-quinolinate and lithium 4,6 dimethyl-8-quinolinate. There may also be used a lithium pyrazolone.

In one embodiment there is provided an optical light emitting diode device having a first electrode, an electron transport layer comprising 1-anthracenyl-9-yl-thianthrene, 1-biphenyl-4-yl-thianthrene or 9,10-bis (1-thianthrenyl) anthracene and a second electrode and optionally a low work function material.

An electron transport layer may comprise a compound having one or two thianthrene moieties linked to conjugated or aromatic hydrocarbon other than alkyl-substituted fluorene, e.g. 1-anthracenyl-9-yl-thianthrene, 1-biphenyl-4-yl-thianthrene or 9,10-bis (1-thianthrenyl) anthracene and a compound of the formula

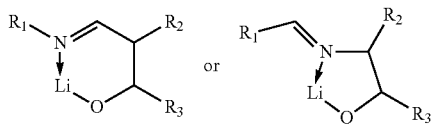

wherein

R$_1$ is a phenyl or naphthyl group (preferably phenyl) which may be substituted with one or more C$_1$-C$_4$ alkyl or alkoxy substituents; and R$_2$ and R$_3$ together form a phenyl or naphthyl group (preferably phenyl) which may be substituted with one or more C$_1$-C$_4$ alkyl or alkoxy substituents. A compound of the above formula may be used alone or in combination with another electron injection material e.g. a quinolate such as lithium or zirconium quinolate or a derivative thereof. Where substituents are present they may be methyl, ethyl, propyl or butyl, including t-butyl substituted, or may be methoxy, ethoxy, propoxy or butoxy including t-butoxy. A particular compounds that may be found in admixture with 1-anthracenyl-9-yl-thianthrene, 1-biphenyl-4-yl-thianthrene or 9,10-bis (1-thianthrenyl) anthracene is

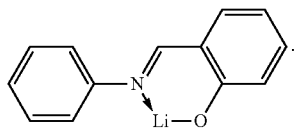

The above OLEDs may have any of the following features:

(a) the emissive layer is composed of a fluorescent emitter;

(b) emissive layer is composed of a phosphorescent emitter;

(c) the emissive layer is composed of ion fluorescent (rare earth based emitters);

(d) a hole injection layer comprising CuPC, ZnTpTP, 2-TNATA, MoO$_3$, MoO$_x$, WO$_3$, WO$_x$ or NiO$_x$ or

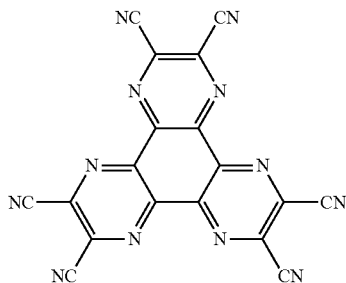 [SMILES: N#Cc1nc2c3nc(C#N)c(C#N)nc3c3nc(C#N)c(C#N)nc3c2nc1C#N]

(e) the hole transporting layer is doped or mixed with an electron acceptor (f) the hole transporting layer is doped or mixed with an electron acceptor such TCNQ or F$_4$TCNQ;

(g) the hole transporter is mixed with another hole transporter;

(h) the electron transporter is mixed with a Li, K, Cs compounds or any other compounds of low work function metals or materials;

(i) the electron transporter is mixed with a rare earth metal or its complexes;

(j) the electron transporter is mixed with Lithium Quinolinoates (Liq) or Lithium Schiff Bases;

(k) the electron transporter is mixed with another electron transporter or electron injector;

(l) the electroluminescent layer comprises a metal complex;

(m) the electroluminescent layer comprises zirconium or hafnium quinolate as host material doped with a dopant;

(n) the electroluminescent layer comprises aluminium quinolate as the host material doped with a dopant.

(o) the electroluminescent layer comprises an aromatic tertiary amine as host material doped with a dopant;

(p) the electroluminescent layer comprises a light emitting material which is a metal or metalloid complex;

(q) the electroluminescent layer comprises as luminescent material a metal quinolate, an iridium, ruthenium, osmium, rhodium, iridium, palladium or platinum complex, a boron complex or a rare earth complex;

(r) the electroluminescent layer comprises as electroluminescent material lithium quinolate or aluminium quinolate;

(s) the electroluminescent layer comprises a light-emitting conjugated polymer or copolymer or a dendrimer;

(t) a hole transport layer comprising α-NPB.

The above compounds may be incorporated into other opto-electronic or electro-optic devices as described below.

BRIEF DESCRIPTION OF THE DRAWINGS

The accompanying FIGS. 1-16 show data obtained with practical green and red OLED devices incorporating compounds or materials of the invention;

DESCRIPTION OF PREFERRED FEATURES

Cell Structure

Figure 3:
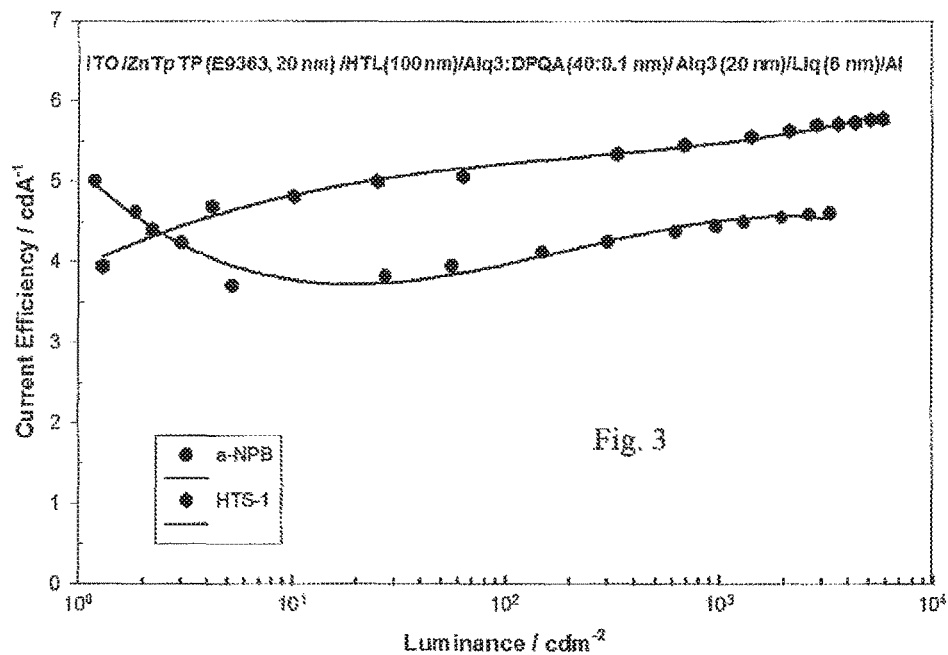
Figure 4:
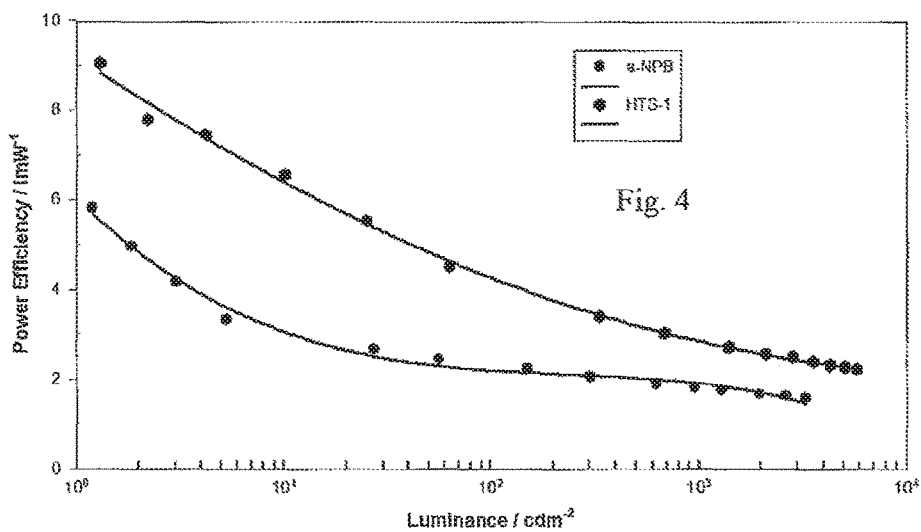
Figure 7:
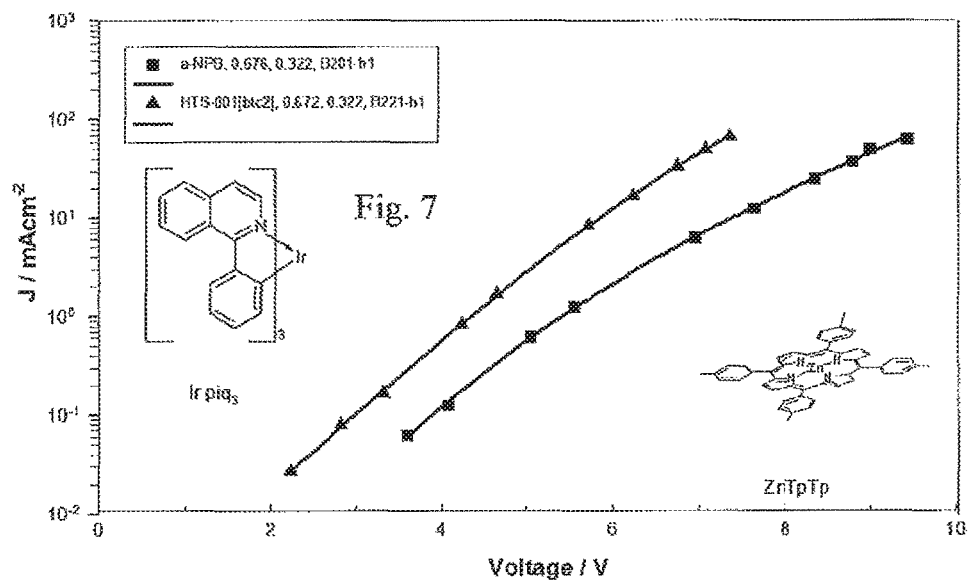
Figure 8:
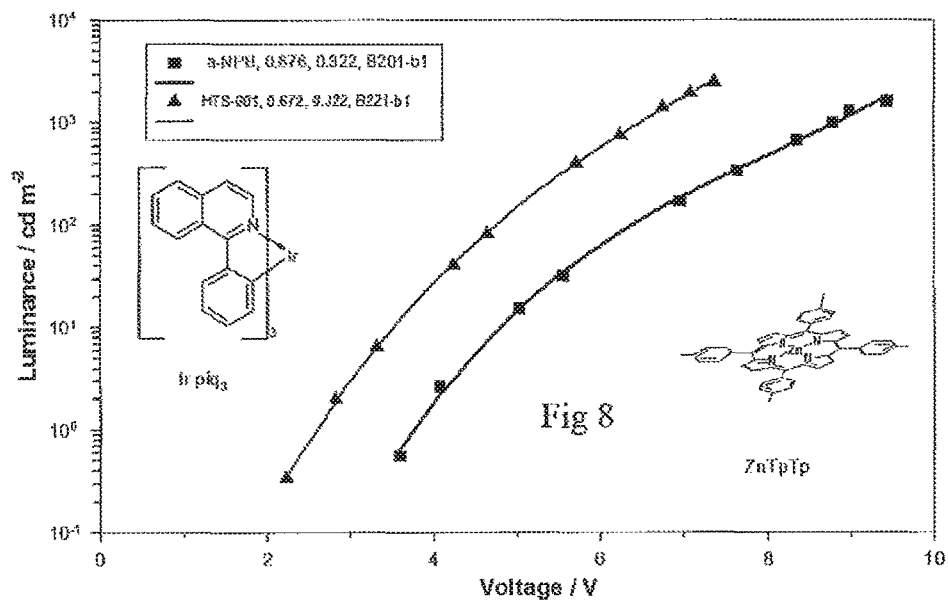

The OLEDs of the invention are useful inter alia in flat panel displays and typically comprise an anode and a cathode between which is sandwiched a multiplicity of thin layers including an electroluminescent layer, electron injection and/or transport layer(s), hole injection and/or transport layer(s) and optionally ancillary layers. The layers are typically built up by successive vacuum vapour deposition operations, although it may be convenient to form one or more of the layers e.g. the hole injection and hole transport layers by other methods e.g. spin coating or ink jet printing.

A typical device comprises a transparent substrate (examples include glass, plastics (PET, PEN etc.), metals or alloys, semiconductors (organic or inorganic)) on which are successively formed an anode layer, a hole injector (buffer) layer, a hole transport layer, an electroluminescent layer, an electron transport layer, an electron injection layer and a cathode layer which may in turn be laminated to a second transparent substrate. Top emitting OLED's are also possible in which an aluminium or other metallic substrate carries an ITO layer, a hole injection layer, a hole transport layer, an electroluminescent layer, an electron transport layer, an electron injection layer and an ITO or other transparent cathode, light being emitted through the cathode. A further possibility is an inverted OLED in which a cathode of aluminium or aluminium alloyed with a low work function metal carries successively an electron injection layer, an electron transport layer, an electroluminescent layer, a hole transport layer, a hole injection layer and an ITO or other transparent conductive anode, emission of light being through the anode. If desired a hole blocking layer may be inserted e.g. between the electroluminescent layer and the electron transport layer.

OLEDs of the invention include small molecule OLEDs, polymer light emitting diodes (p-OLEDs), OLEDs that emit light by fluorescence, OLEDs that emit light by phosphorescence (PHOLEDs) and OLEDs that emit light by ion fluorescence (rare earth complexes) and include single-colour or multi-colour active or passive matrix displays.

Anode

In many embodiments the anode is formed by a layer of tin oxide or indium tin oxide coated onto glass or other transparent substrate. Other materials that may be used include antimony tin oxide, aluminium zinc oxide and indium zinc oxide. Other anode materials also include conducting polymers (example: poly(thiophene)(s), poly (aniline)(s) and poly(pyrrole)(s)). If desired a modified anode may be produced e.g. by subsequently treating the ITO surface with oxygen plasma, and then conditioned as a modified anode by decomposing $CHF_3$ gas in a plasma treatment chamber to deposit a ~1-nm-thick layer of $CF_x$. In active matrix embodiments the anode may be a high work function metal or alloy e.g. gold or platinum or may be crystalline, polycrystalline, continuous grain or amorphous silicon which may be p-doped or metal oxides such Mo, W and Ni oxides. Cells in which the anode is of doped or un-doped graphene are also within the invention.

Hole Injection and Hole Transport Layers

Commonly OLEDs have distinct hole injection and hole transport layers. The applicant has considered the properties that are desirable for the material of a hole injection layer and for the material of a hole transport layer of an OLED, and these are set out in the table below:

| Property | Hole Injectors (HI's) | Hole Transporters (HT's) |
|---|---|---|
| LUMO Level | Not critical | Critical<br>E LUMO ≥ −2.6 eV<br>(i.e. \|E LUMO\| ≤2.6 eV) |
| HOMO Level | E HOMO ≤ −5.2 eV<br>(i.e. \|EHOMO\| ≥5.2 eV) | Deeper than the hole injector<br>E HOMO ≤ −5.7 eV<br>(i.e. \|E HOMO\| ≥5.7 eV) |
| Hole mobility ($\mu_e$) | As high as possible | As high as possible, preferably greater than<br>$1 \times 10^{-5}$ cm$^2$V$^{-1}$s$^{-1}$ |
| Capable of acting as a planarization layer for the anode | Yes | Not a pre-requisite as it is normally deposited on the hole injector. |
| Interface to the anode | Must act as an "anchoring" agent with good adhesion. Must improve the film forming properties of the subsequent organic layers. | Capable of forming amorphous films. |
| Thermal stability | High Tg (glass transition temperature), Tm (melting point) and Td (decomposition point)<br>Tg > 150° C., Tm > 250° C., Td > 350° C. (under nitrogen) | High Tg (glass transition temperature), Tm (melting point) and Td (decomposition point)<br>Tg > 120° C., Tm > 250° C., Td > 250° C. (under nitrogen) |
| Doping | N. A | Capable of being doped with acceptor molecules to enhance the conductivity. |
| Typical thickness | 1 nm-100 nm | 20-200 nm |

It will be appreciated that many of the above characteristics are desirable rather than essential. For example, although Tg (where such a transition occurs or is detectable) should be as high as possible, many current hole injection materials have Tg of 100-120° C., or in some instances lower e.g. about 90° C.

Hole Injection Materials

A single layer may be provided between the anode and the electroluminescent material, but in many embodiments there are at least two layers one of which is a hole injection layer (buffer layer) and the other of which is a hole transport layer, the two layer structure offering in some embodiments improved stability and device life, see U.S. Pat. No. 4,720,432 (VanSlyke et al., Kodak). The hole injection layer may serve to improve the film formation properties of subsequent organic layers and to facilitate the injection of holes into the hole transport layer.

Suitable materials for the hole injection layer which may be of thickness e.g. 0.1-200 nm depending on material and cell type include hole-injecting porphyrinic compounds— see U.S. Pat. No. 4,356,429 (Tang, Eastman Kodak) e.g. zinc phthalocyanine, copper phthalocyanine and ZnTpTP, whose formula is set out below:

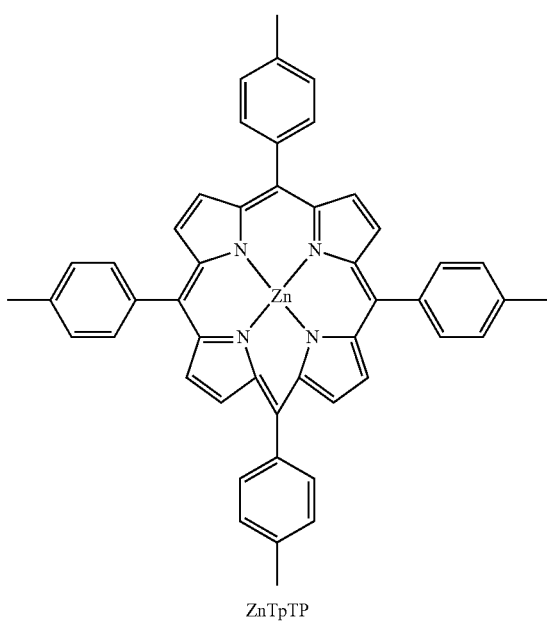

ZnTpTP

Particularly good device efficiencies, turn/on voltages and/or lifetimes may be obtained where the hole injection layer is ZnTpTP. A further material that may be used is hexacyanohexaazatriphenylene (CHATP) of structure:

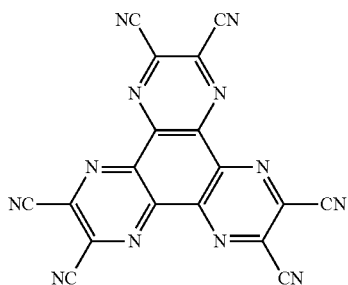 [SMILES: N#Cc1nc2c3nc(C#N)c(C#N)nc3c3nc(C#N)c(C#N)nc3c2nc1C#N]

The hole injection layer may also be a fluorocarbon-based conductive polymer formed by plasma polymerization of a fluorocarbon gas—see U.S. Pat. No. 6,208,075 (Hung et al; Eastman Kodak), a triarylamine polymer—see EP-A-0891121 (Inoue et al., TDK Corporation) or a phenylenediamine derivative—see EP-A-1029909 (Kawamura et al., Idemitsu) or the materials described in U.S. Pat. No. 6,436,559 (Ueno, Canon) and 6720573 (Se-Hwan, LG Chemical Co., Ltd.). It may also be a solution-processable hole injecting polymer e.g. PEDOT/PSS (poly-3,4-ethylenedioxythiophene doped with poly(styrenesulfonate) or a block copolymer of PEDOT and a flexible polymer such as a polyether, polysiloxane, polyester, or polyacrylate. Poly(aniline)(s) and Poly(pyrrole)(s) are also part of this invention. Methods of applying such materials include solution processing methods, e.g. spin coating, printing through a mask and ink jet printing e.g. of a relatively dilute solution where thin hole injection layers are desired.

Other hole injectors include oxides of Mo, W and Ni.

Hole-Transport Materials

Hole transport layers which may be used are in some embodiments preferably of thickness 10 to 200 nm, e.g. 20-200 nm.

The hole transport compounds used herein include compounds having at least one thianthrene residue per molecule. In some embodiments the thianthrene residue serves as scaffold and may have one or two ring substituents which are aryl or heteroaryl. Linkage may be at any ring position or in the case of compounds having two ring aryl or heteroaryl substituents they may be at any pair of stereochemically compatible ring positions e.g. the 1-, 2-, 1,9- or 2,7-positions of the tricyclic ring. Said residue or residues may be optionally mono-, bi- or poly-substituted with $C_1$-$C_4$-alkyl-, $C_1$-$C_4$-alkoxy-, fluoro, phenyl or biphenyl which in the case of phenyl or biphenyl substituents may be themselves further substituted with $C_1$-$C_4$-alkyl- (preferably methyl), $C_1$-$C_4$-alkoxy-(preferably methoxy) or fluoro. Alkyl substituents include methyl, ethyl, n-propyl, i-propyl and t-butyl. Alkoxy substituents include methoxy, ethoxy, n-propoxy, i-propoxy and t-butoxy. The residue or residues may also include an aryl linking group attached at one end as a substituent to the thianthrene residue e.g. 1,4-phenylene optionally substituted by $C_1$-$C_4$-alkyl- (preferably methyl), $C_1$-$C_4$-alkoxy- (preferably methoxy) or fluoro. The hole transport material may, for example, include one, two or three thianthrene residues per molecule, with two such residues at present being believed an optimum.

The following numbering system is used for the thianthrene ring and the other related ring structures mentioned herein:

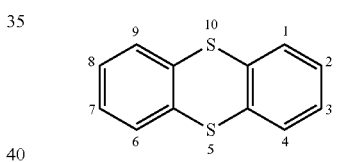

A sub-genus of the above hole transport compounds has a tricyclic structure attached to a triarylamine or triaryl phosphine oxide having a single nitrogen or phosphorus atom and includes compounds having a favourable combination of melting points, phase transition temperatures and hole mobilities for use in electronic devices.

A broad genus of compounds has one or more nitrogen, phosphorus or silicon atoms bonded to thianthrene via aryl. Such compounds may be of the formula:

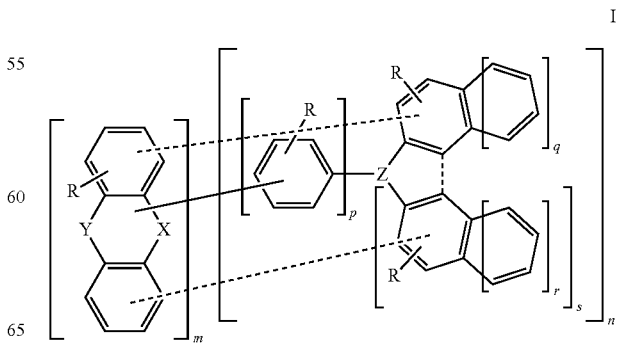

I wherein:

Z is N, P=O or Si;

X and Y each represent S;

the groups R which may be the same or different independently represent hydrogen or one or more ring substituents selected from methyl, methoxy, ethyl, ethoxy, aryl (e.g. phenyl) and fluoro;

m is 1-3 when Z is N or P=O or may be 1-4 when Z is Si;

n is 0 or 1;

p is 0, 1 or 2;

q and r are 0 or 1, s is 1 when Z is N or P=O or is 2 when Z is Si;

the dotted linkage when present indicates that the two phenyl rings form part of a 9H-carbazol-9-yl residue the solid line indicates a linkage between the tricyclic ring directly, by phenyl or by biphenyl; and linkages to the tricyclic ring may be at its 1- or 2-position or may be at its 2, 7 or 2,8-positions.

A group of the above compounds has n=1, p=1 or 2 and m is 1, 2 or 2, the linkages between triaryl and Z being phenyl or biphenyl. Another group has m=1, n=1 or 2 and p=0 or 1.

Triarylamines and Related Phosphine Oxides and Silane Derivatives

A particular sub-group of compounds incorporating a single triarylamine residue may be of the formula:

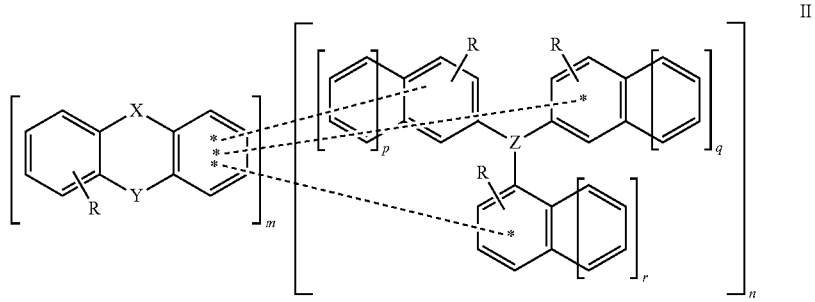

wherein:

m is 1, 2 or 3, the dotted lines correspondingly representing bonds for each phenothiazine residue to one of the phenyl or naphthyl rings;

n is 1 or 2;

p, q and r are independently 0 or 1;

X and Y each represent S;

Z represents N or P=O;

the groups R which may be the same or different independently represent hydrogen or ring substituents selected from methyl, methoxy, ethyl, ethoxy, aryl (e.g. phenyl) and fluoro; and linkages may be at the 1- or 2-position of the tricyclic ring or rings or may be at the 2, 7 or 2,8-positions and may be o- or p- to the phenyl or naphthyl rings to which they are attached.

In one group of these compounds m is 1 and n is 1, 2 or 3. In another group of compounds m is 1 and n is 1 or 2.

For example, the scaffold may be triphenylamine with one, two or three of the phenyl rings substituted with a thianthrene residue of the type described above. The thiazine residue may be attached to the phenyl ring at any sterically available position, commonly the 4-position as in many of the compounds shown below.

In compounds where X is NH and Y is O, S or Se, attachment may be between the nitrogen atom and a phenyl ring at any sterically available position, most usually the 4-position.

The compound N-4-(thianthren-1-yl)triphenylamine (also phenyl-N-(4-(thianthren-7-yl)phenyl)benzenamine) can be made by brominating thianthrene under reflux in acetic acid to give 2-bromothianthrene which is reacted with aqueous acidic trimethyl borate to give thianthren-2-yl-2-boronic acid which is a widely useful intermediate for Suzuki coupling reactions to provide thianthren-2-yl compounds herein. The above intermediate is Suzuki coupled (Pd(0)/K$_2$CO$_3$) with N-(4-bromophenyl)-N-phenylbenzenamine to give the desired product. Likewise the compound N,N-bis(4-bromophenyl)benzenamine can be Suzuki coupled with thianthren-2-yl-2-boronic acid to give 4,4"-di-(thianthren-1-yl)triphenylamine (also phenyl-bis-4-thianthren-2-yl)phenylamine) of structure

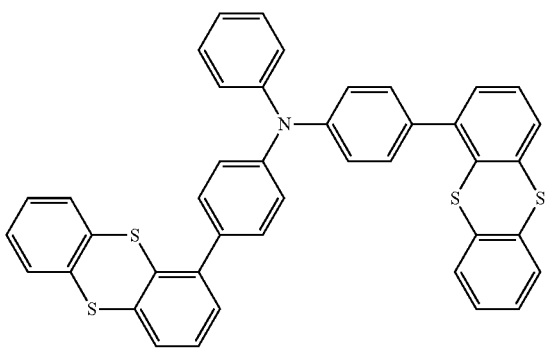 [SMILES: c1ccc(N(c2ccc(-c3cccc4c3Sc3ccccc3S4)cc2)c2ccc(-c3cccc4c3Sc3ccccc3S4)cc2)cc1]

The compound 4-(thianthren-1-yl)-4',4"-dimethoxytriphenylamine (also 4-methoxy-N-(4-methoxyphenyl)-N-(4-(thianthren-9-yl)phenyl)benzenamine) may be made as follows:

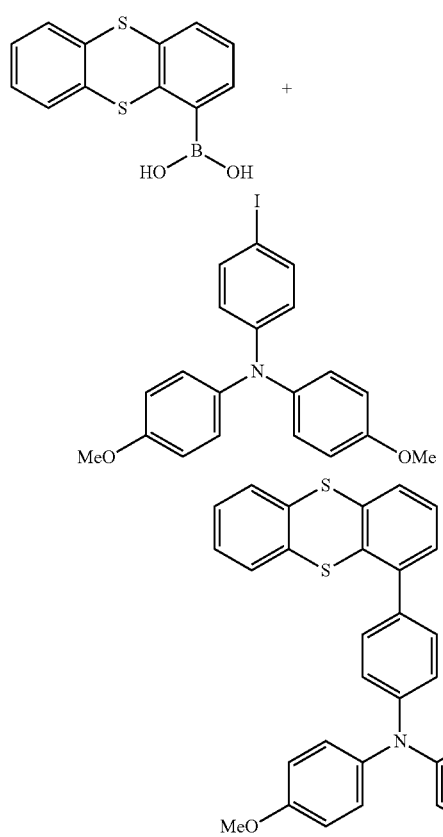
N-4-(2,8-dimethoxythianthren-1-yl)triphenylamine (also (4-(2,8-dimethoxy-thianthren-9-yl)phenyl)-N-phenylbenzenamine) may be made by the following sequence of reactions:
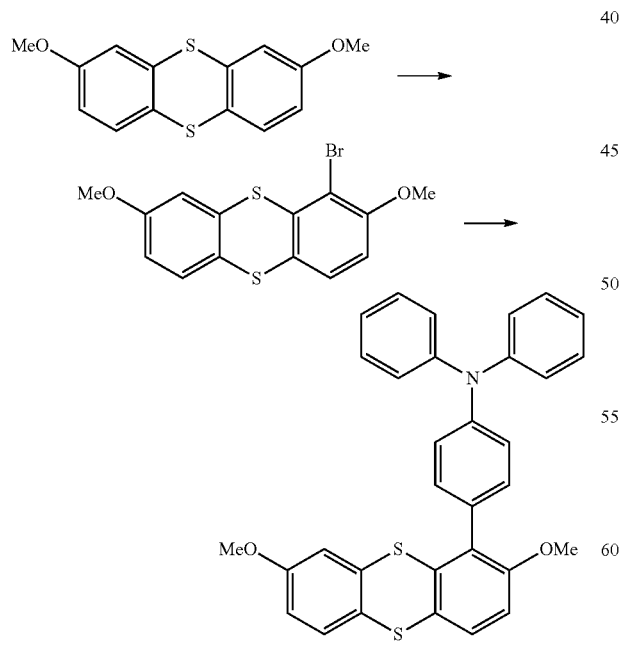
4-(N-Phenyl-N-m-tolylamino)-4'-(thianthren-1-yl)biphenyl may also be made by Suzuki coupling as shown:
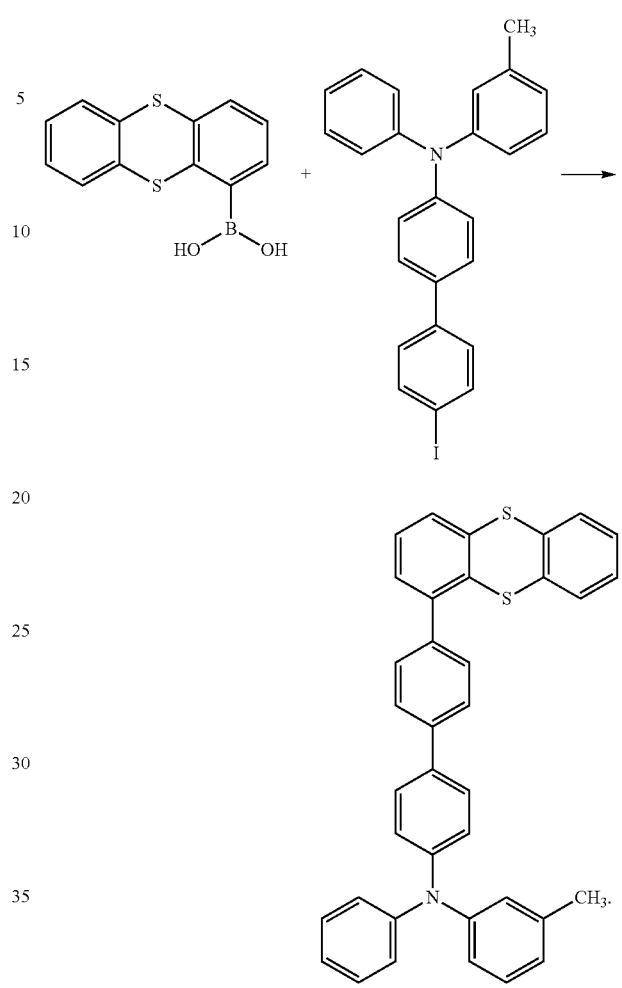
See also the following compounds:
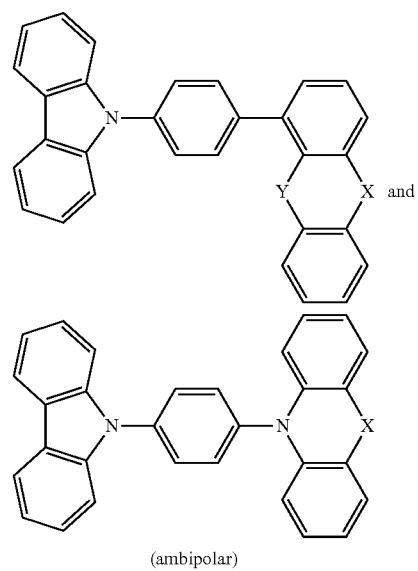
(ambipolar)
wherein X and Y are S.

Compounds within this sub-genus include compounds of name and/or structural formula below.

4-(thianthren-1-yl)triphenylamine (HTS-1);
4,4'-di-(thianthren-1-yl)triphenylamine (HTS-4);
4,4',4"-tri-(thianthren-1-yl)triphenylamine (HTS-2);
4-(thianthren-2-yl)triphenylamine;
4,4'-di-(thianthren-2-yl)triphenylamine;
4,4',4"-tri-(thianthren-2-yl)triphenylam
2,7-bis-(4-diphenylaminophenyl)thianthrene
2,7-bis-(4-diphenylaminophenyl)-3,8-dimethylthianthrene
3-(thianthren-2-yl)triphenylamine;
N-(4-thianthren-1-ylphenyl)-di-p-tolylamine;
4-(thianthren-1-yl)-4',4"-dimethoxytriphenylamine;
4-(2,8-dimethoxythianthren-1-yl)triphenylamine;
1,9-di-(4-(diphenylamino)phenyl)thianthrene;
4-(thianthren-1-yl)triphenylphosphine oxide;
N-phenyl-N-(1-(thianthren-1-yl)naphthalen-4-yl)naphthalen-1-amine;
N-(naphthalen-1-yl)-N-(4-(thianthren-1-yl)phenyl)naphthalen-1-amine;
N-(naphthalen-1-yl)-N-(1-(thianthren-1-yl)naphthalen-4-yl)naphthalen-1-amine;
4-(N-Phenyl-N-m-tolylamino)-4'-(thianthren-1-yl)biphenyl;

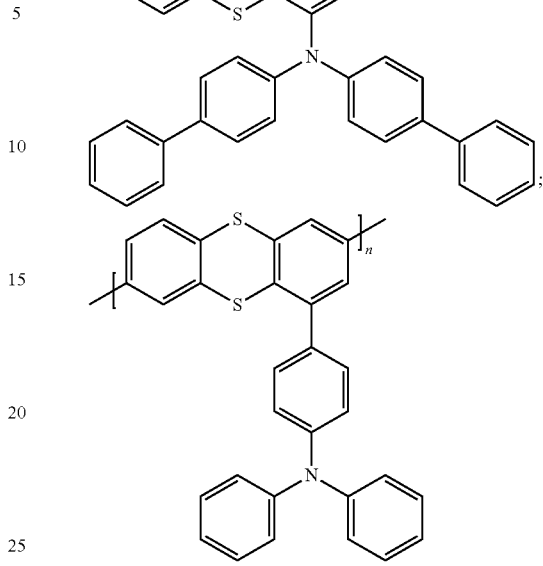

Triphenylphosphine Oxide Compounds

Compounds containing triphenyl phosphine e.g. 4-(thianthren-1-yl)triphenylphosphine oxide and 4-(thianthren-2-yl)triphenylphosphine oxide and may be generically represented as indicated below, X and Y both represent S:

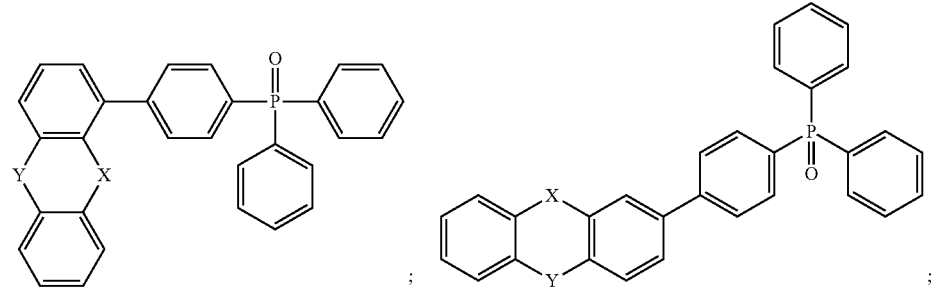

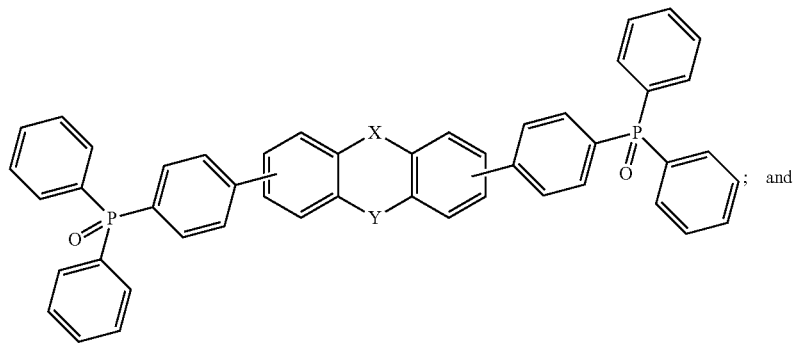

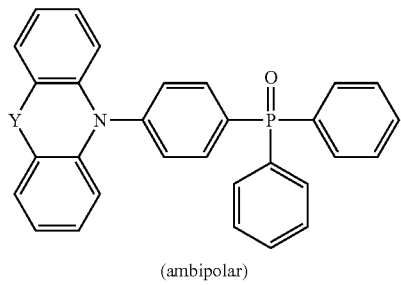

(ambipolar)

Similar to the above sub-genus are compounds where an above defined tricyclic structure is attached to tetraphenyl-silane to give a compound of formula III of which examples in the thianthrene and appear below:

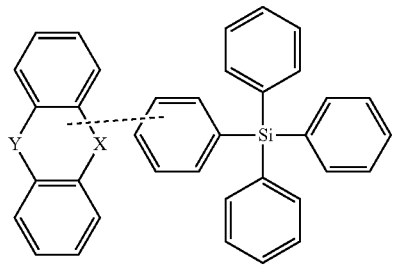

III

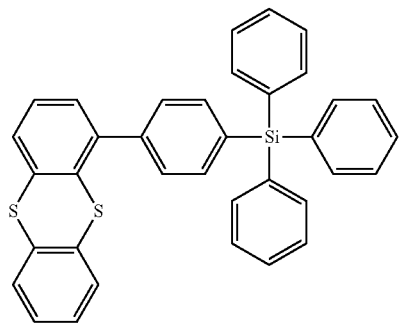

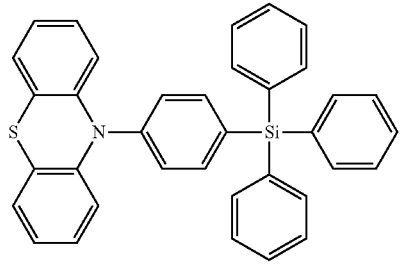

Ring substitution with methyl, methoxy or fluoro is also possible, and the molecules could contain 2, 3 or 4 thianthrene residues per molecule.

Compounds Containing Aminobiphenyl, Diaminobiphenyl, 2,7-Diaminofluorene, 2,7-Dimaninospirobifluorene and 2,7,2',7'Tetraaminospirobifluorene Residues Hole transport materials of the above type may, for example be of the formula

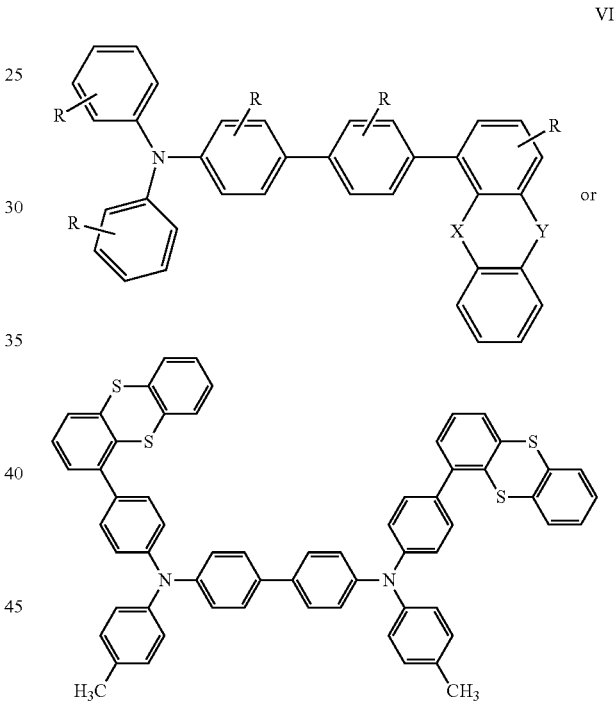

wherein X and Y are S, R is as defined above and $R_1$ may be phenyl which may be substituted with methyl, methoxy or fluoro (e.g. to give m-tolyl or p-tolyl) or the groups R may together form part of a spirobifluorene group. In formulae VI and VII, it will be understood that the groups R on the biphenyl rings may form fluorine or spirobifluorene.

Examples of such compounds include:
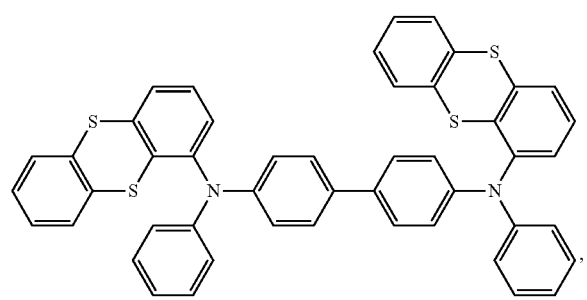
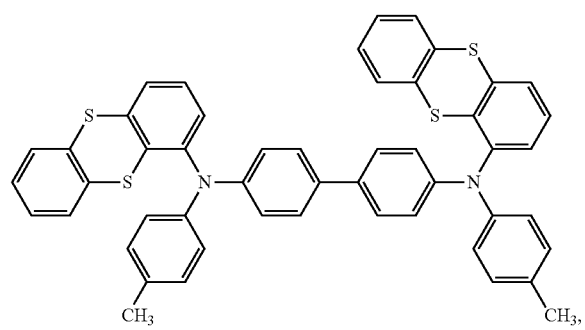
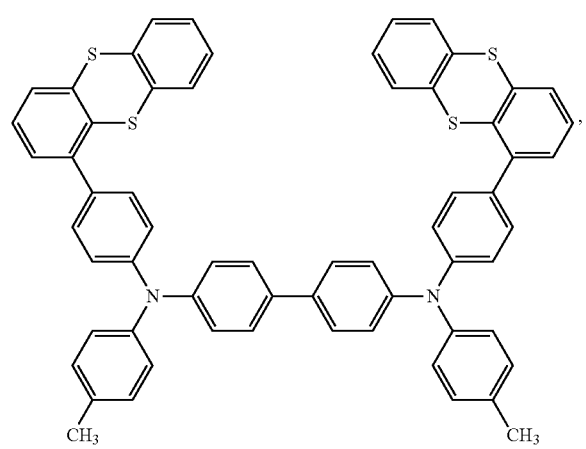
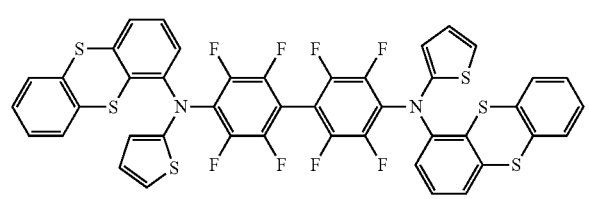
Examples of preparative methods are shown below
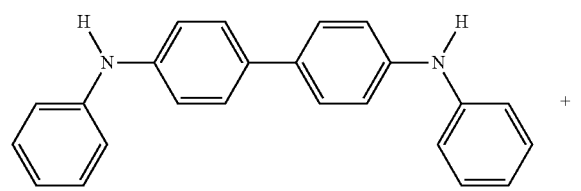
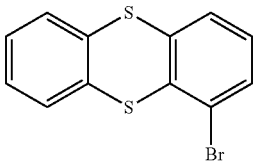
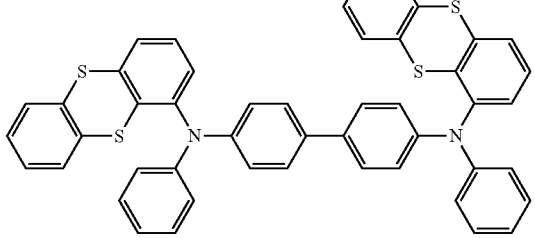
and
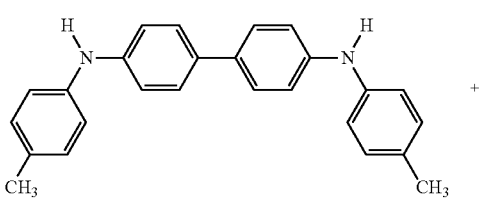
+
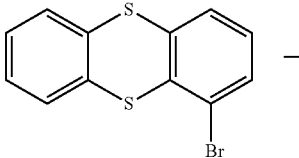
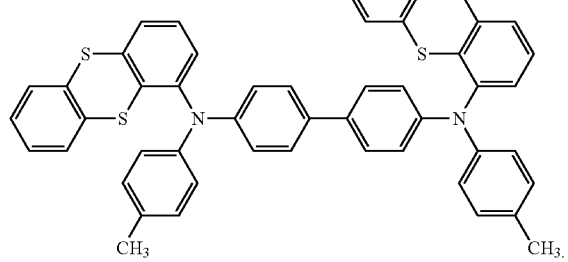
The following structures (which may be varied along the general lines indicated above are also analogous:
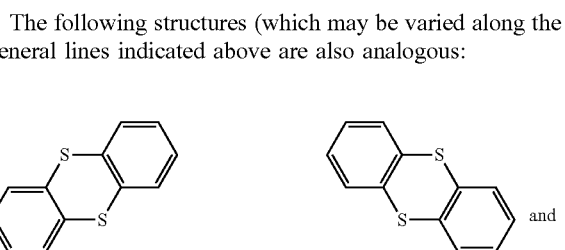
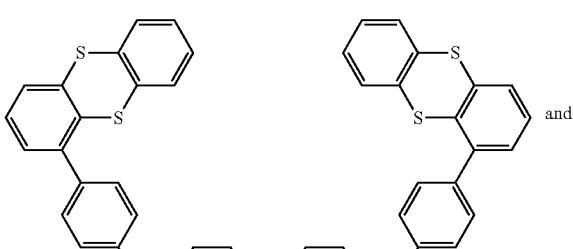
and
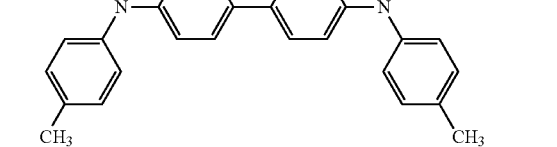

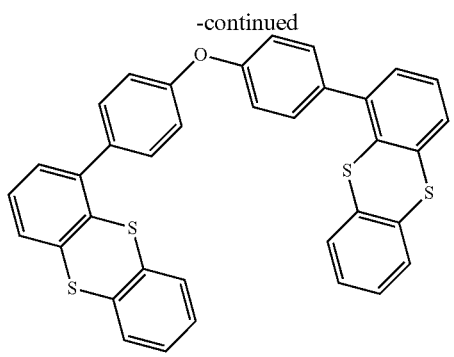

Compounds Having One, Two or Three Thianthrene Moieties Linked to Conjugated or Aromatic Hydrocarbon Other than Alkyl-Substituted Fluorene

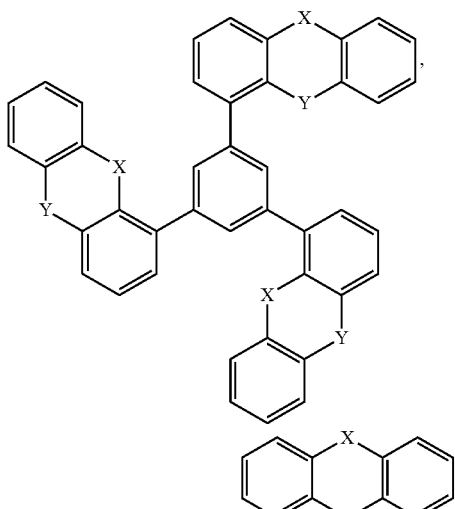

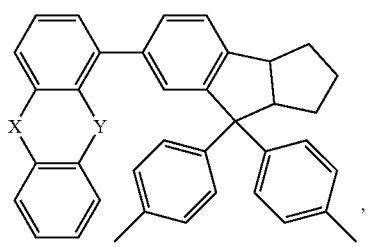

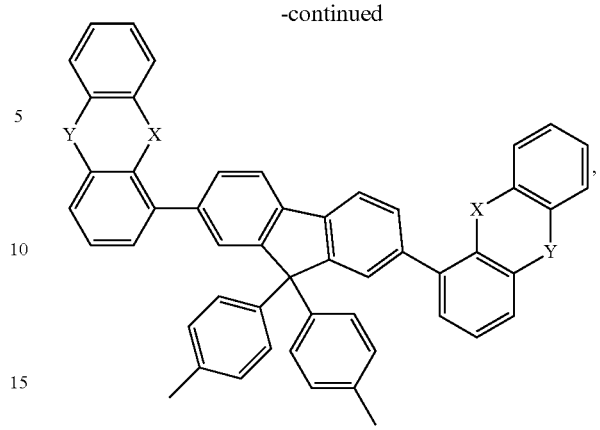

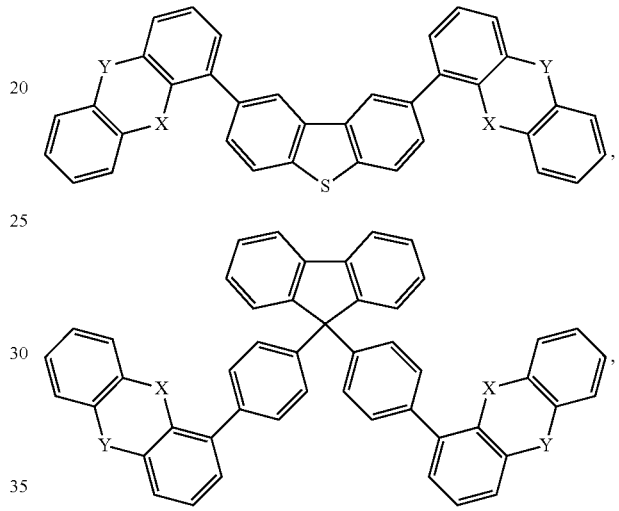

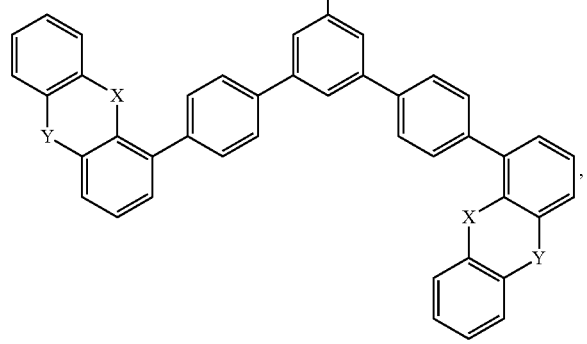

wherein R, X and Y is as defined in claim 1 and in embodiments X and Y are both S.

Compounds in this class include the following:
2-(naphthalen-1-yl)thianthrene
1-(phenanthren-9-yl)thianthrene,
1-(10-phenylanthracen-9-yl)thianthrene,
1-(4-(thiophen-2-yl)phenyl)thianthrene
1-(9,10-di(naphthalen-2-yl)anthracen-6-yl)thianthrene
10-(4-(9H-carbazol-9-yl)phenyl)-10H-phenothiazine
2-(10H-phenothiazinyl)dibenzothiophene
9,10-di(thianthren-1 yl)anthracene
1,3,5-tri(thianthren-1-yl)benzene
1,3,5-tris-(4-(thianthren-1-yl)phenyl)benzene
(4(9-(4-(thianthren-1-yl)phenyl)-9H-carbazole
9-(4-(thianthren-1-yl)benzyl)-9H-carbazole
1-phenyl-2-(4-(thianthren-9-yl)phenyl)-1H-benzo[d]imidazole
2-phenyl-1-(4-(thianthren-1-yl)phenyl)ethanone
1-(9,9-di-p-tolyl-9H-fluoren-2-yl)thianthrene
1-(2-(thianthren-1-yl)-9,9-di-p-tolyl-9H-fluoren-7-yl)thianthrene
1-(9,9-dipropyl-2-(thianthren-1-yl)-9H-fluoren-7-yl)thianthrene,
1-(4-(9-(4-(thianthren-1-yl)phenyl)-9H-fluoren-9-yl)phenyl)thianthrene
1-(4-(9-(4-(thianthren-1-yl)phenyl)-9H-fluoren-9-yl)phenyl)thianthren

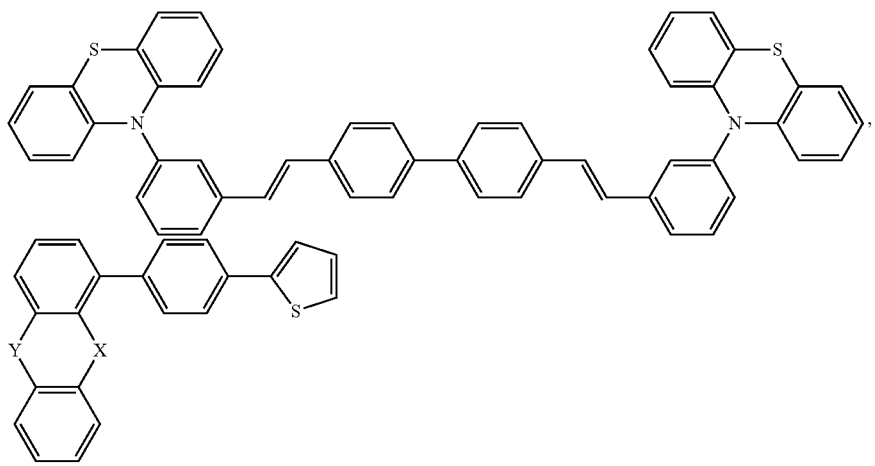

The compound 9-(4-(thianthren-1-yl)phenyl)-9H-carbazole can be prepared by reacting 9H-carbazole with 1-bromo-4-iodobenzene under reflux in NMP in the presence of CuI and $K_2CO_3$ to give 9-(4-bromophenyl)-9H-carbazole which in turn is Suzuki coupled with thianthren-1-yl-1-boronic acid (a generally useful intermediate for thianthren-1-yl compounds herein) to give the desired product.

Dopants for the Hole Transport Layer

The hole transport layer may comprise any of the above mentioned compounds which are sublimable small molecules and which may be p-doped e.g. with an acceptor-type organic molecule e.g. tetracyanoquinodimethane or tetrafluorotetracyano-quinodimethane ($F_4$-TCNQ). The amount of dopant may be such as to contribute 10-40% e.g. about 33% to layer thickness. In addition to one of the above mentioned thianthrene compounds and optionally p-type dopant, there may be present additionally one or more known hole transport compounds which may also be sublimable small molecules. For example, aromatic tertiary amines provide a class of preferred hole-transport materials, e.g. aromatic tertiary amines having at least two aromatic tertiary amine moieties (e.g. those based on biphenyl diamine or of a "starburst" configuration).

For example, aromatic amines may be used of the general formulae (i)-(vii) below:

(i)

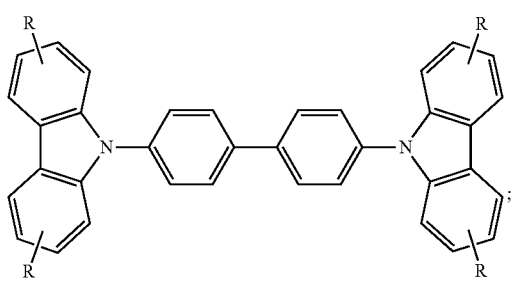

(ii)

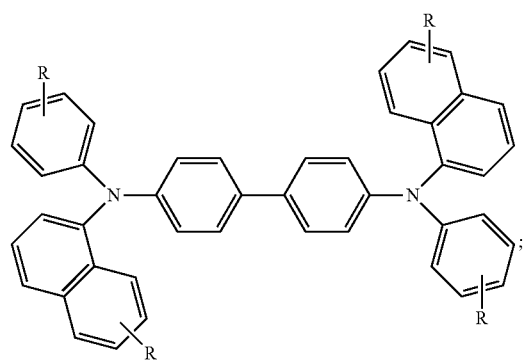

(iii)

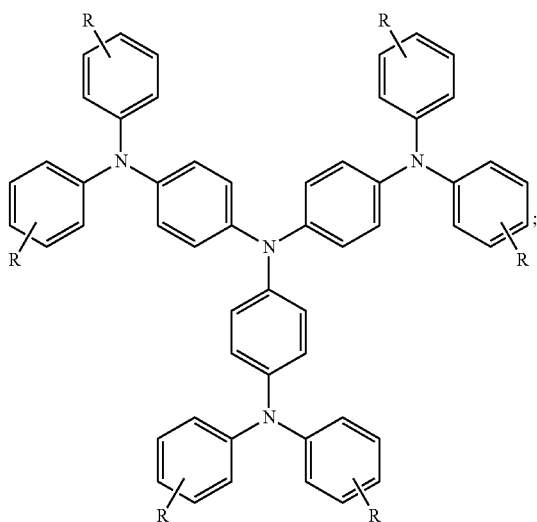

(iv)

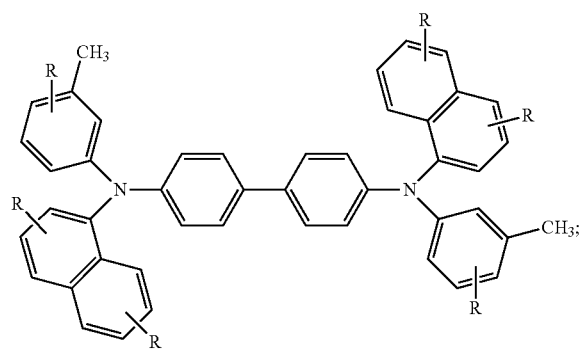

(v)

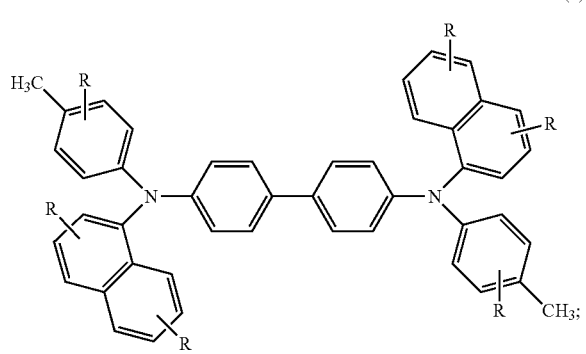

(vi)

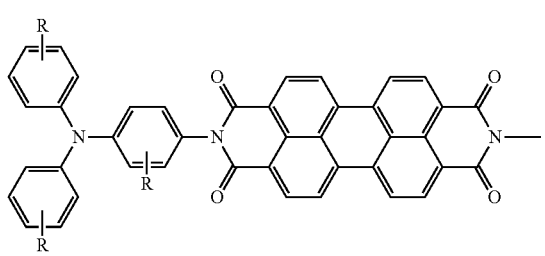

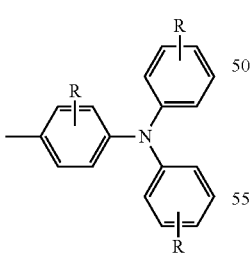

wherein the groups R in any of the formulae in (i) to (vi) can be the same or different and are selected from hydrogen; substituted and unsubstituted aliphatic groups; substituted and unsubstituted aromatic, heterocyclic and polycyclic ring structures; halogens; and thiophenyl groups; and wherein in formula (i) the methyl groups may be replaced by $C_1$-$C_4$ alkyl or monocyclic or polyclic aryl or heteroraryl which may be further substituted e.g. with alkyl, aryl or arylamino.

Further hole transport materials comprise

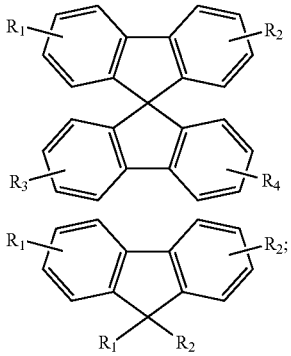

wherein the groups $R_1$-$R_4$ when appearing in either of the above formulae can be the same or different and are selected from hydrogen; substituted and unsubstituted aliphatic groups; substituted and unsubstituted aromatic, heterocyclic and polycyclic ring structures; halogens; and thiophenyl groups.

The following are representative of suitable aromatic tertiary amines:

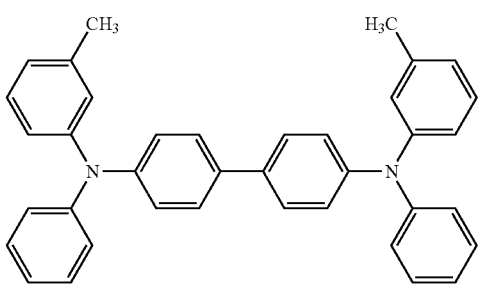

TPD
Tg (° C.) 61
µh (cm² V⁻¹ s⁻¹) 1 x 10⁻³

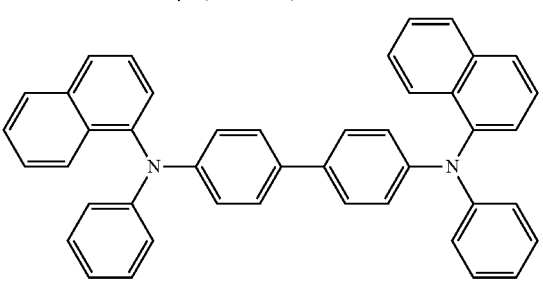

α-NPB
Tg (° C.) 98
µh (cm² V⁻¹ s⁻¹) 1 x 10⁻⁴

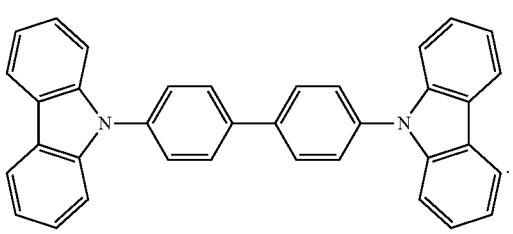

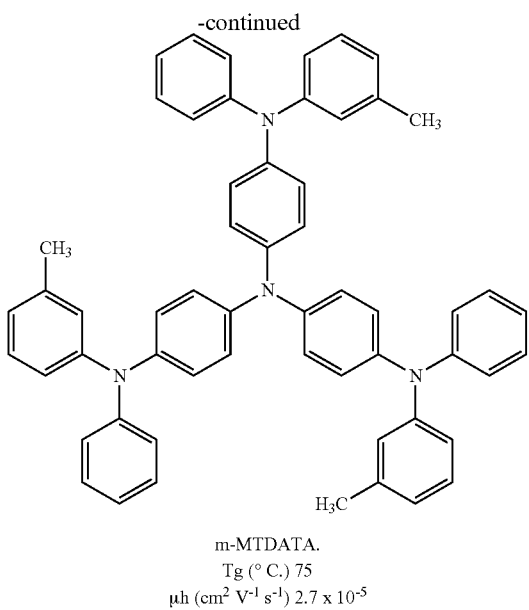

m-MTDATA.
Tg (° C.) 75
μh (cm$^2$ V$^{-1}$ s$^{-1}$) 2.7 x 10$^{-5}$

A further possible material is 4,4',4"-tris(carbazolyl)-triphenylamine (TCTA) which is a hole transport material with a wider band gap than α-NPB and which can in some embodiments assist in confining excitation to the emissive layer.

Further possible materials are spiro-linked molecules which are aromatic amines e.g. spiro-TAD (2,2',7,7'-tetrakis-(diphenylamino)-spiro-9,9'-bifluorene).

A further class of small molecule hole transport materials is disclosed in WO 2006/061594 (Kathirgamanathan et al) and is based on diamino dianthracenes. Typical compounds include:
9-(10-(N-(naphthalen-1-yl)-N-phenylamino)anthracen-9-yl)-N-(naphthalen-1-yl)-N-phenylanthracen-10-amine;
9-(10-(N-biphenyl-N-2-m-tolylamino)anthracen-9-yl)-N-biphenyl-N-2-m-tolylamino-anthracen-10-amine; and
9-(10-(N-phenyl-N-m-tolylamino)anthracen-9-yl)-N-phenyl-N-m-tolylanthracen-10-amine.

Hole transport layers which may be used are preferably of thickness 10 to 200 nm.

Electroluminescent Materials

In principle any electroluminescent material may be used, including molecular solids which may be fluorescent dyes e.g. perylene dyes, metal complexes e.g. Alq$_3$, Ir(III)L$_3$, rare earth chelates e.g. Tb(III) complexes, dendrimers and oligomers e.g. sexithiophene, or polymeric (conjugated or otherwise) emissive materials. The electroluminescent layer may comprise as luminescent material a metal quinolate, iridium, ruthenium, osmium, rhodium, palladium or platinum complex, a boron complex or a rare earth complex One preferred class of electroluminescent materials comprises host materials doped with dyes which may be fluorescent, phosphorescent or ion-phosphorescent (rare earth). The term "electroluminescent device" includes electrophosphorescent devices.

Preferably the host is doped with a minor amount of a fluorescent material as a dopant, preferably in an amount of 0.01 to 25% by weight of the doped mixture. As discussed in U.S. Pat. No. 4,769,292 (Tang et al., Kodak), the contents of which are included by reference, the presence of the fluorescent material permits a choice from amongst a wide latitude of wavelengths of light emission. In particular, as disclosed in U.S. Pat. No. 4,769,292 by blending with the organo metallic complex a minor amount of a fluorescent material capable of emitting light in response to hole-electron recombination, the hue of the light emitted from the luminescent zone, can be modified. In theory, if a host material and a fluorescent material could be found for blending which have exactly the same affinity for hole-electron recombination, each material should emit light upon injection of holes and electrons in the luminescent zone. The perceived hue of light emission would be the visual integration of both emissions. However, since imposing such a balance of host material and fluorescent materials is limiting, it is preferred to choose the fluorescent material so that it provides the favoured sites for light emission. When only a small proportion of fluorescent material providing favoured sites for light emission is present, peak intensity wavelength emissions typical of the host material can be entirely eliminated in favour of a new peak intensity wavelength emission attributable to the fluorescent material.

While the minimum proportion of fluorescent material sufficient to achieve this effect varies, in no instance is it necessary to employ more than about 10 mole percent fluorescent material, based of host material and seldom is it necessary to employ more than 1 mole percent of the fluorescent material. On the other hand, limiting the fluorescent material present to extremely small amounts, typically less than about 10$^{-3}$ mole percent, based on the host material, can result in retaining emission at wavelengths characteristic of the host material. Thus, by choosing the proportion of a fluorescent material capable of providing favoured sites for light emission, either a full or partial shifting of emission wavelengths can be realized. This allows the spectral emissions of the EL devices to be selected and balanced to suit the application to be served. In the case of fluorescent dyes, typical amounts are 0.01 to 5 wt %, for example 2-3 wt %. In the case of phosphorescent dyes typical amounts are 0.1 to 15 wt %. In the case of ion phosphorescent materials typical amounts are 0.01-25 wt % or up to 100 wt %.

Choosing fluorescent materials capable of providing favoured sites for light emission, necessarily involves relating the properties of the fluorescent material to those of the host material. The host can be viewed as a collector for injected holes and electrons with the fluorescent material providing the molecular sites for light emission. One important relationship for choosing a fluorescent material capable of modifying the hue of light emission when present in the host is a comparison of the reduction potentials of the two materials. The fluorescent materials demonstrated to shift the wavelength of light emission have exhibited a less negative reduction potential than that of the host. Reduction potentials, measured in electron volts, have been widely reported in the literature along with varied techniques for their measurement. Since it is a comparison of reduction potentials rather than their absolute values which is desired, it is apparent that any accepted technique for reduction potential measurement can be employed, provided both the fluorescent and host reduction potentials are similarly measured. A preferred oxidation and reduction potential measurement techniques is reported by R. J. Cox, *Photographic Sensitivity*, Academic Press, 1973, Chapter 15.

A second important relationship for choosing a fluorescent material capable of modifying the hue of light emission when present in the host is a comparison of the band-gap potentials of the two materials. The fluorescent materials demonstrated to shift the wavelength of light emission have exhibited a lower band gap potential than that of the host.

The band gap potential of a molecule is taken as the potential difference in electron volts (eV) separating its ground state and first singlet state. Band gap potentials and techniques for their measurement have been widely reported in the literature. The band gap potentials herein reported are those measured in electron volts (eV) at an absorption wavelength which is bathochromic to the absorption peak and of a magnitude one tenth that of the magnitude of the absorption peak. Since it is a comparison of band gap potentials rather than their absolute values which is desired, it is apparent that any accepted technique for band gap measurement can be employed, provided both the fluorescent and host band gaps are similarly measured. One illustrative measurement technique is disclosed by F. Gutman and L. E. Lyons, *Organic Semiconductors*, Wiley, 1967, Chapter 5.

With host materials which are themselves capable of emitting light in the absence of the fluorescent material, it has been observed that suppression of light emission at the wavelengths of emission characteristics of the host alone and enhancement of emission at wavelengths characteristic of the fluorescent material occurs when spectral coupling of the host and fluorescent material is achieved. By "spectral coupling" it is meant that an overlap exists between the wavelengths of emission characteristic of the host alone and the wavelengths of light absorption of the fluorescent material in the absence of the host.

Optimal spectral coupling occurs when the emission wavelength of the host is within ±25 nm of the maximum absorption of the fluorescent material alone. In practice advantageous spectral coupling can occur with peak emission and absorption wavelengths differing by up to 100 nm or more, depending on the width of the peaks and their hypsochromic and bathochromic slopes. Where less than optimum spectral coupling between the host and fluorescent materials is contemplated, a bathochromic as compared to a hypsochromic displacement of the fluorescent material produces more efficient results.

Useful fluorescent materials are those capable of being blended with the host and fabricated into thin films satisfying the thickness ranges described above forming the luminescent zones of the EL devices of this invention. While crystalline organometallic complexes do not lend themselves to thin film formation, the limited amounts of fluorescent materials present in the host permit the use of fluorescent materials which are alone incapable of thin film formation. Preferred fluorescent materials are those which form a common phase with the host. Fluorescent dyes constitute a preferred class of fluorescent materials, since dyes lend themselves to molecular level distribution in the host. Although any convenient technique for dispersing the fluorescent dyes in the host can be used preferred fluorescent dyes are those which can be vacuum vapour deposited along with the host materials.

One class of host materials comprises metal complexes e.g. metal quinolates such as lithium quinolate, aluminium quinolate, titanium quinolate, zirconium quinolate or hafnium quinolate which may be doped with fluorescent materials or dyes as disclosed in patent application WO 2004/058913.

In the case of quinolates e.g. aluminium quinolate:
(a) the compounds below, for example, can serve as red dopants:

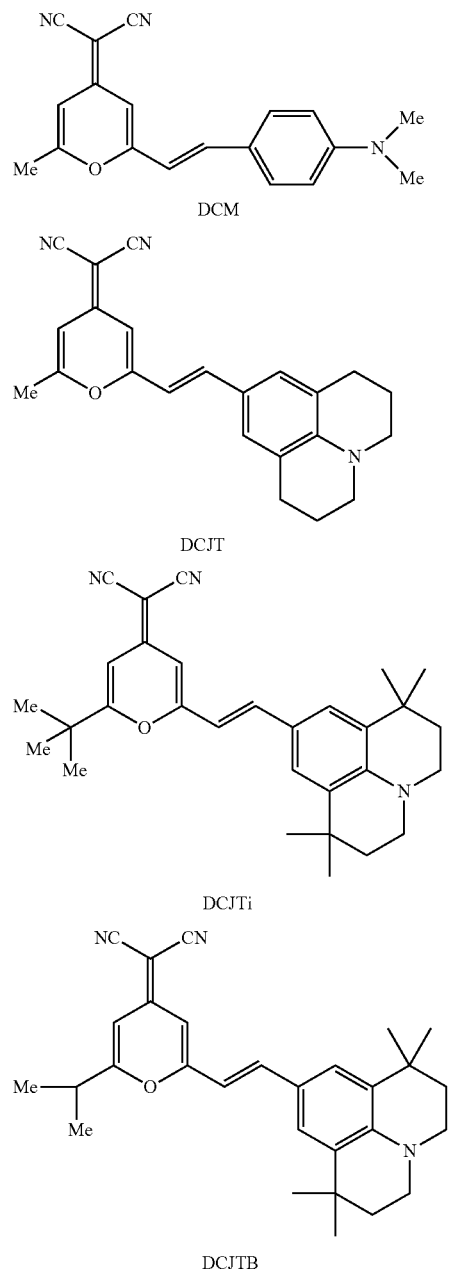

(b) the compounds below, for example can serve as green dopants:

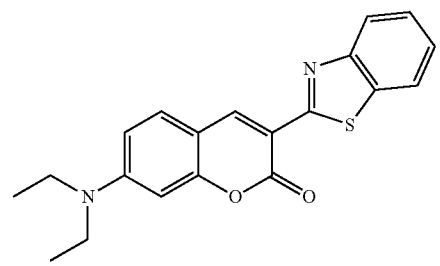

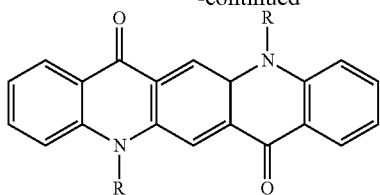

wherein R is $C_1$-$C_4$ alkyl, monocyclic aryl, bicycic aryl, monocyclic heteroaryl, bicyclic heteroaryl, aralkyl or thienyl, preferably phenyl; and (c) for biphenyloxy aluminium bis-quinolate ($BAlQ_2$), $BAq_2$ (aluminium bis(-2-methylquinolate) or aluminium quinolate the compounds perylene and 9-(10-(N-(naphthalen-8-yl)-N-phenylamino)anthracen-9-yl)-N-(naphthalen-8-yl)-N-phenylanthracen-10-amine can serve as a blue dopants.

Another preferred class of hosts is small molecules incorporating conjugated aromatic systems with e.g. 4-10 aryl or heteroaryl rings which may bear substituents e.g. alkyl (especially methyl), alkoxy and fluoro and which may also be doped with fluorescent materials or dyes.

An example of a system of the above kind is a blue-emitting material based on the following compound (Compound H) as host

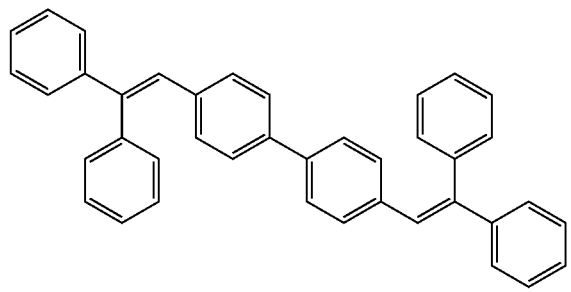 [SMILES: C(=C(c1ccccc1)c1ccccc1)c1ccc(-c2ccc(C=C(c3ccccc3)c3ccccc3)cc2)cc1]

and perylene or 9-(10-(N-(naphthalen-8-yl)-N-phenylamino)anthracen-9-yl)-N-(naphthalen-8-yl)-N-phenylanthracen-10-amine as dopant. Further examples of host materials which are small aromatic molecules are shown below:

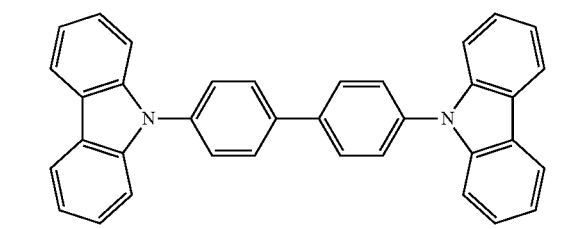

CBP

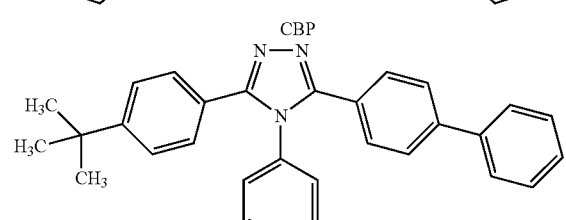

TAZ

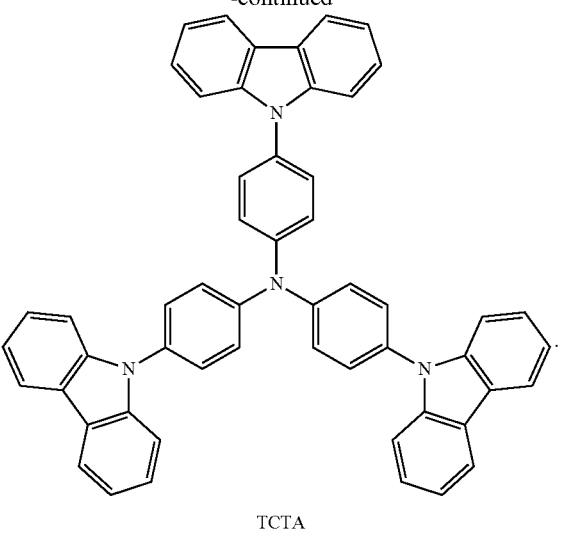

TCTA 2,9-Bis(2-thiophen-2-yl-vinyl)-[1,10] phenanthroline may, as explained above, may be used as host in the electroluminescent layer or may be present on its own. Other blue emitting systems include

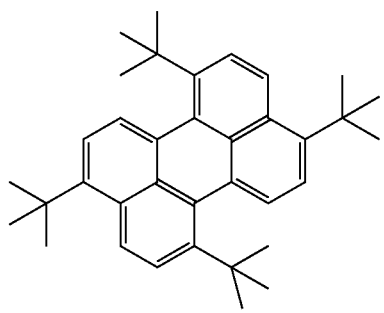

Tetra-tert-Butyl Perylene

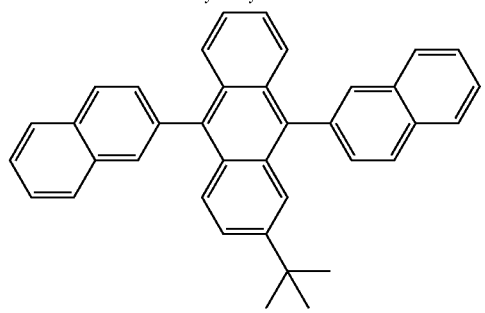

TBADN

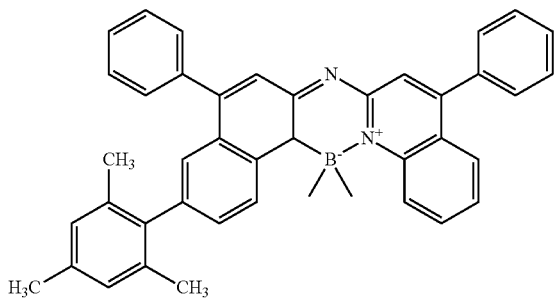

BD-3

Blue-emitting materials may be based on an organic host (e.g. a conjugated aromatic compound as indicated above) and diarylamine anthracene compounds disclosed in WO 2006/090098 (Kathirgamanathan et al.) as dopants. For example, CBP may be doped with blue-emitting substituted anthracenes inter alia 9,10-bis(-4-methylbenzyl)-anthracene, 9,10-bis-(2,4-dimethylbenzyl)-anthracene, 9,10-bis-(2,5-dimethylbenzyl)-anthracene, 1,4-bis-(2,3,5,6-tetramethylbenzyl)-anthracene, 9,10-bis-(4-methoxybenzyl)-anthracene, 9,10-bis-(9H-fluoren-9-yl)-anthracene, 2,6-di-t-butylanthracene, 2,6-di-t-butyl-9,10-bis-(2,5-dimethylbenzyl)-anthracene, 2,6-di-t-butyl-9,10-bis-(naphthalene-1-ylmethyl)-anthracene.

Further blue-emitting materials may employ TCTA as host and it may be doped with the blue phosphorescent materials set out below, see WO 2005/080526 (Kathirgamanathan et al.):

Blue Phosphorescent Materials

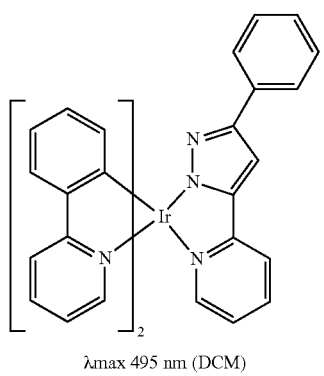

λmax 495 nm (DCM)

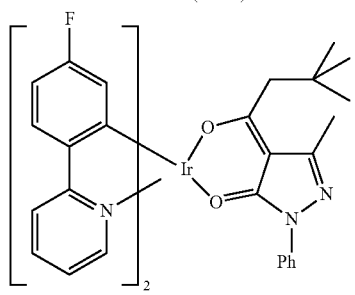

λmax 493 nm (DCM)

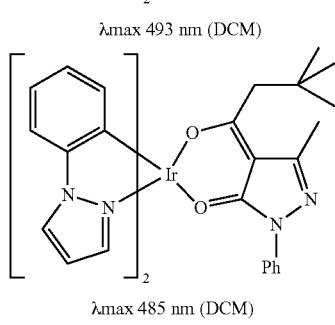

λmax 485 nm (DCM)

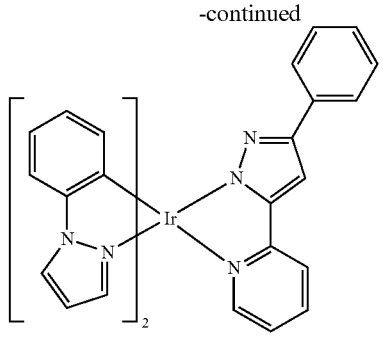

λmax 485 nm (DCM)

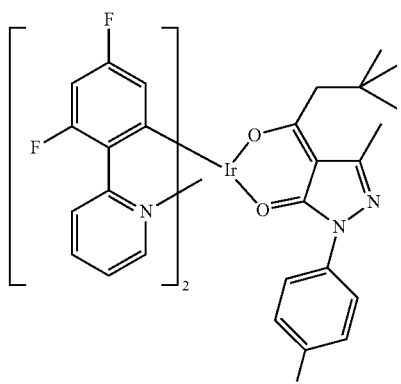

λmax 484 nm (DCM)

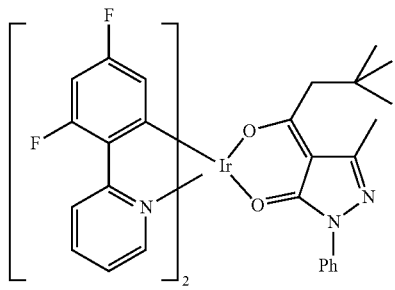

λmax 483 nm (DCM)

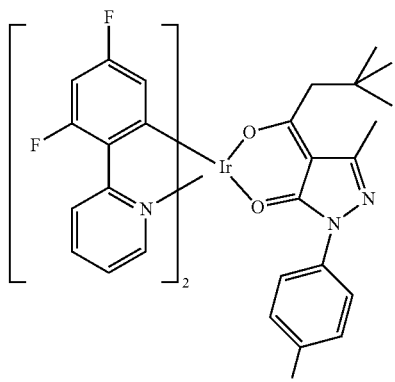

λmax 480 nm (DCM)

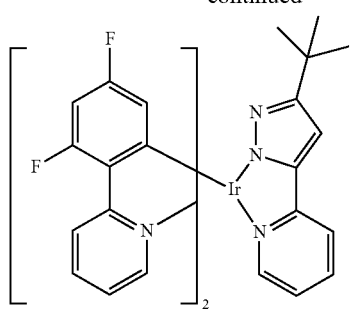
λmax 479 nm (DCM)
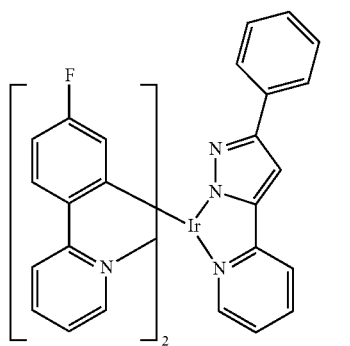
λmax 477 nm (DCM)
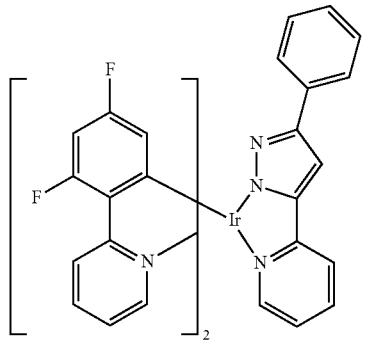
λmax 470 nm (DCM)
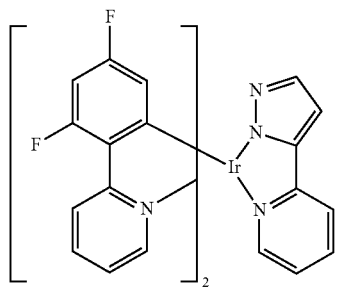
λmax 469,493 nm (DCM)
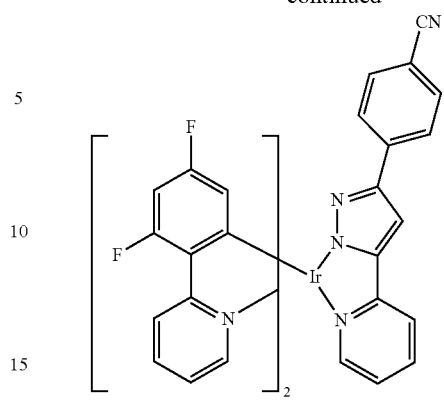
λmax 468 nm (DCM)
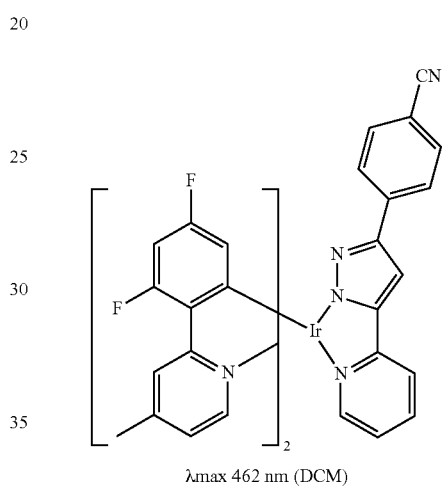
λmax 462 nm (DCM)
Examples of green phosphorescent materials that may be employed with CBP or TAZ are set out below (see WO 2005/080526):
Green Phosphorescent Materials
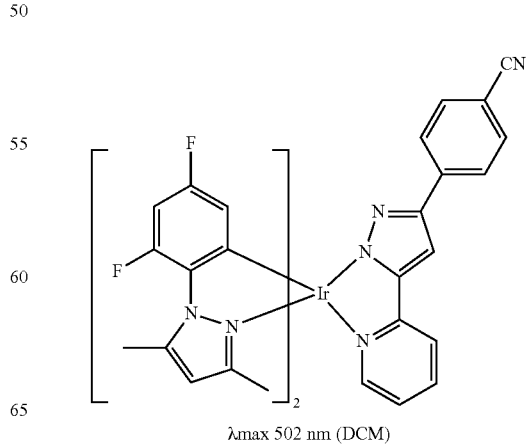
λmax 502 nm (DCM)

-continued
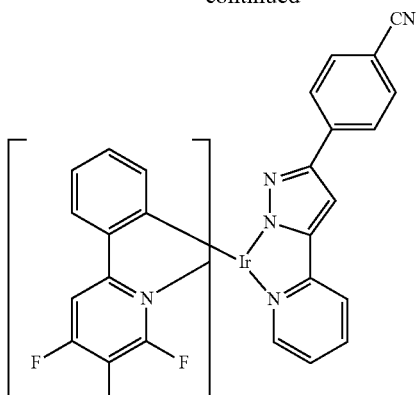
λmax 509 nm (DCM)
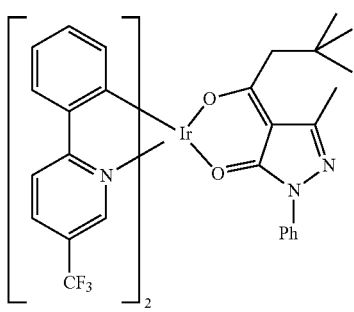
λmax 520 nm (DCM)
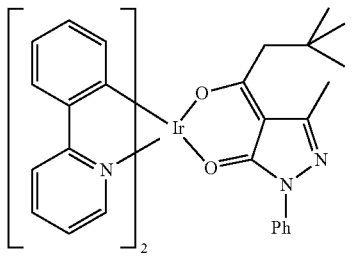
λmax 526 nm (DCM)
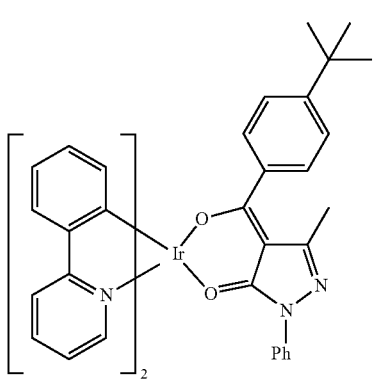
λmax 528 nm (DCM)
-continued
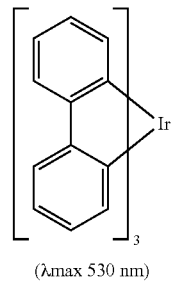
(λmax 530 nm)
Examples of red phosphorescent materials that may be employed with CBP or TAZ are set out below (see WO 2005/080526):
Red Phosphorescent Materials
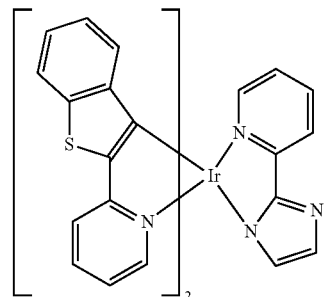
λmax 596 nm (DCM)
λmax 596 nm (DCM)
λmax 597 nm (DCM)

-continued
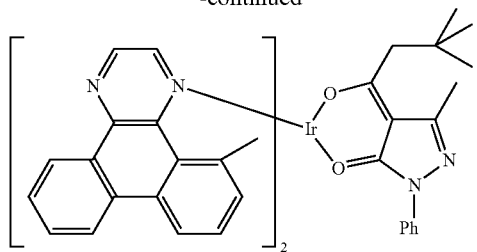
λmax 600 nm (DCM)
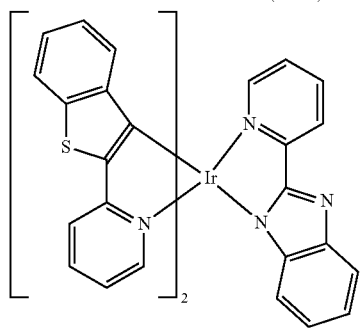
λmax 604 nm (DCM)
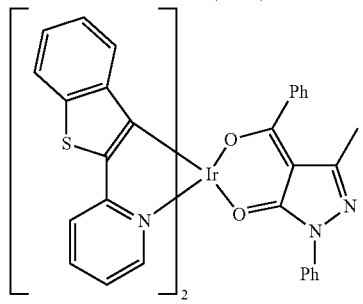
λmax 614 nm (DCM)
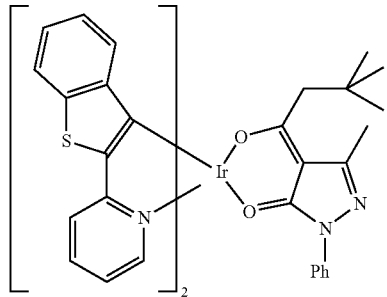
λmax 615 nm (DCM)
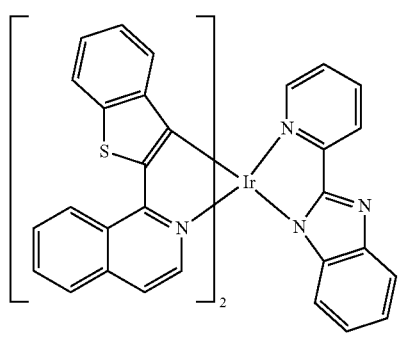
λmax 682 nm (DCM)
Further examples are:
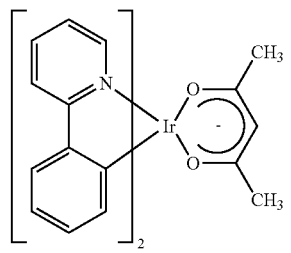
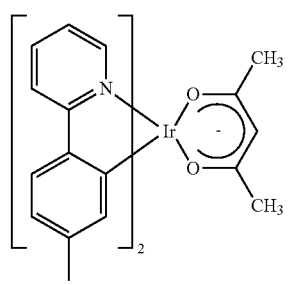
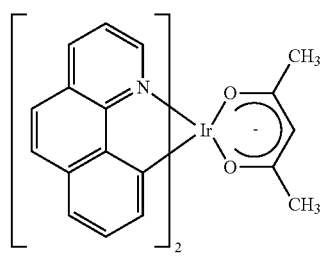
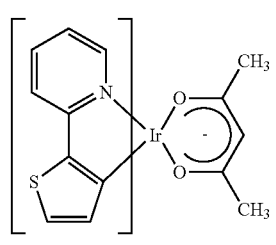
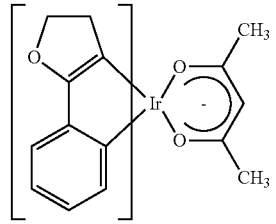
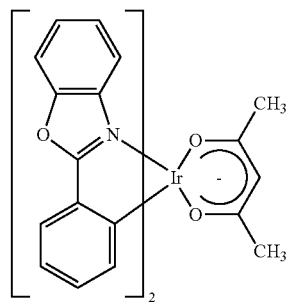

-continued
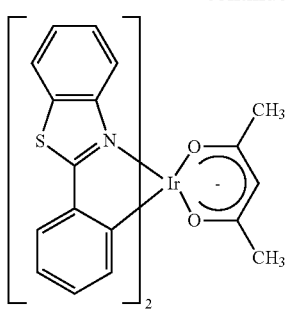
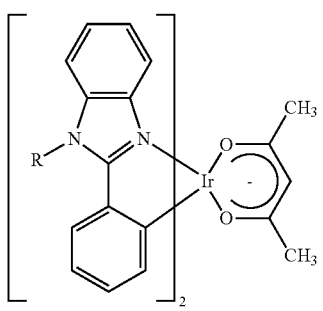
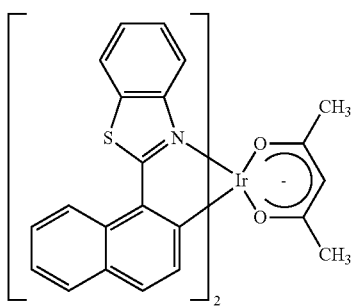
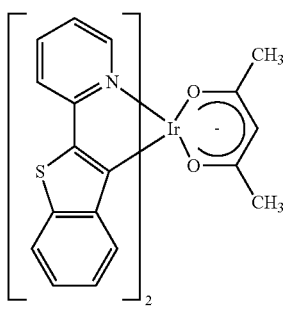
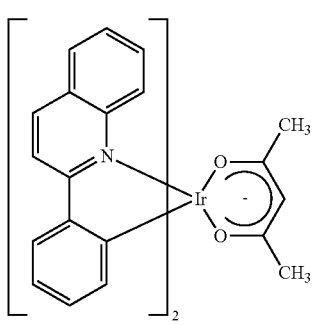
-continued
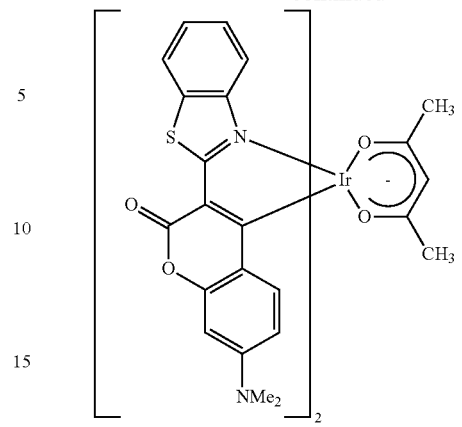
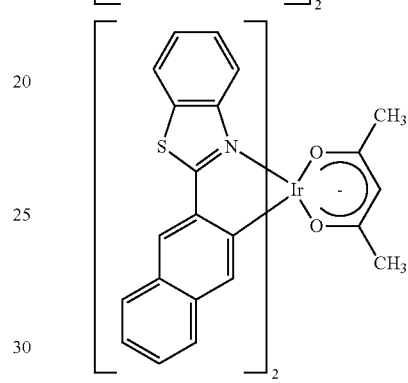
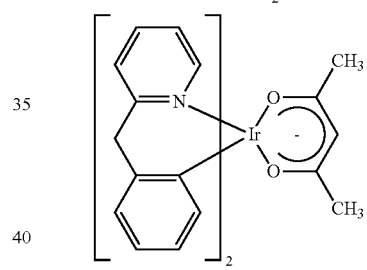
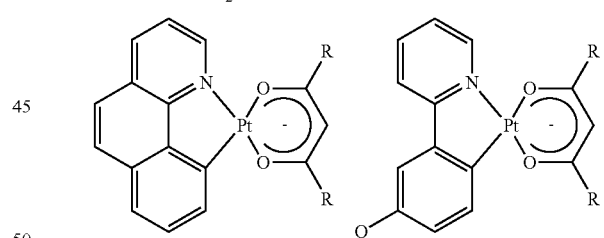
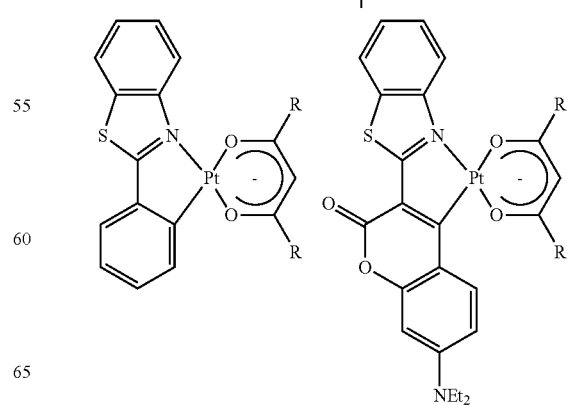

49
-continued
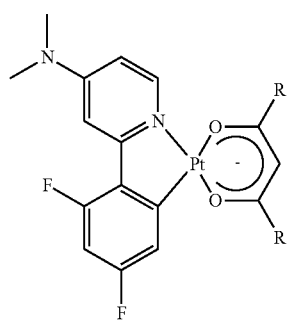
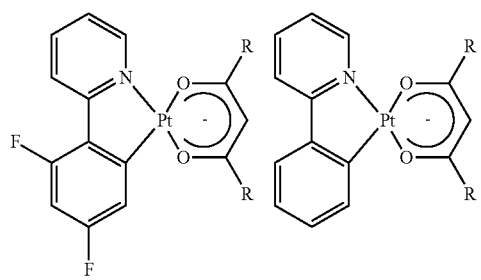
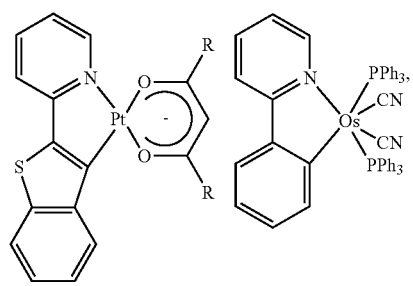
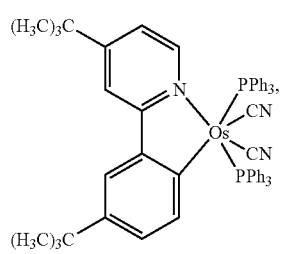
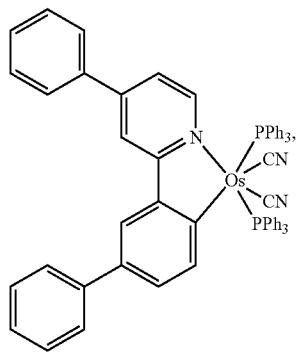
50
-continued
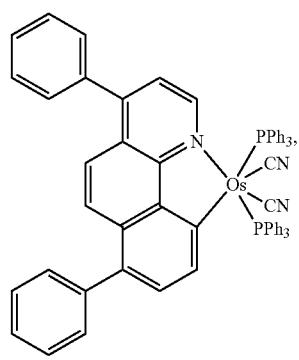
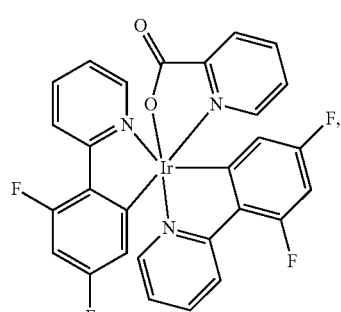
Flrpic
fac Ir(ppy)3
Ir(MDQ)₂acac -continued

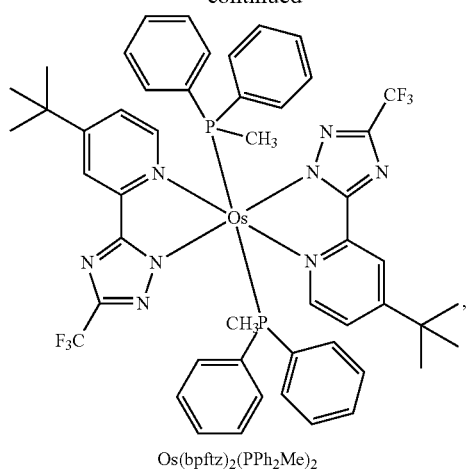

Os(bpftz)₂(PPh₂Me)₂

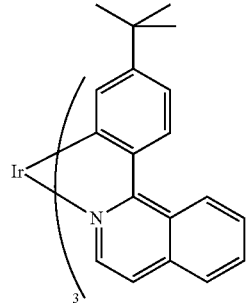

Os(fpftz)₂(PPhMe₂)₂

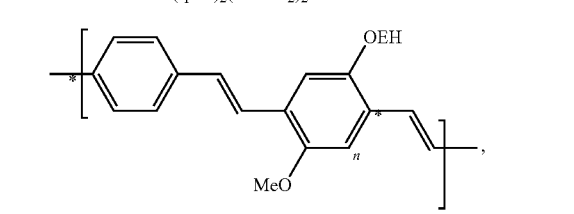

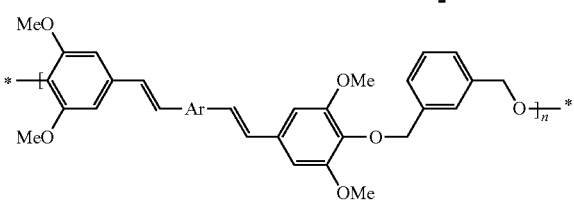

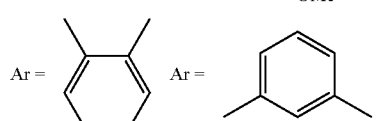

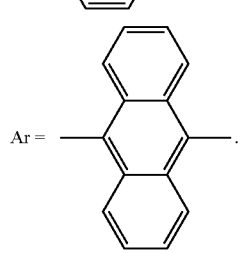

Other examples include dendrimers such as

PRID1

PRID2

PRID3

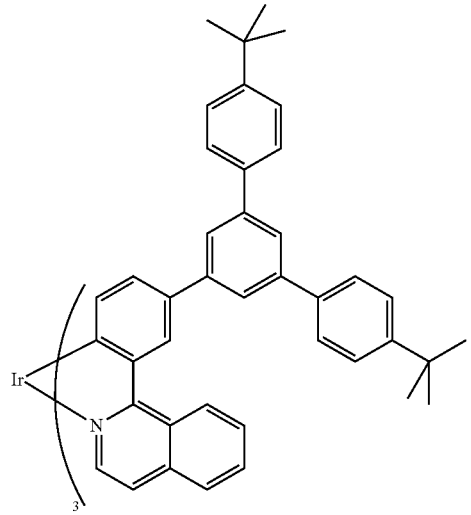

As further dopants, fluorescent laser dyes are recognized to be particularly useful fluorescent materials for use in the organic EL devices of this invention. Dopants which can be used include diphenylacridine, coumarins, perylene and their derivatives. Useful fluorescent dopants are disclosed in U.S. Pat. No. 4,769,292. One class of preferred dopants is coumarins. The following are illustrative fluorescent coumarin dyes known to be useful as laser dyes:
FD-1 7-Diethylamino-4-methylcoumarin,
FD-2 4,6-Dimethyl-7-ethylaminocoumarin,
FD-3 4-Methylumbelliferone,
FD-4 3-(2'-Benzothiazolyl)-7-diethylaminocoumarin,
FD-5 3-(2'-Benzimidazolyl)-7-N,N-diethylaminocoumarin,
FD-6 7-Amino-3-phenylcoumarin,
FD-7 3-(2'-N-Methylbenzimidazolyl)-7-N,Ndiethylaminocoumarin,
FD-8 7-Diethylamino-4-trifluoromethylcoumarin,
FD-9 2,3,5,6-1H,4H-Tetrahydro-8-methylquinolazino[9,9a,1-gh]coumarin,
FD-10 Cyclopenta[c]julolindino[9,10-3]-11H-pyran-11-one,
FD-11 7-Amino-4-methylcoumarin,
FD-12 7-Dimethylaminocyclopenta[c]coumarin,
FD-13 7-Amino-4-trifluoromethylcoumarin,
FD-14 7-Dimethylamino-4-trifluoromethylcoumarin,
FD-15 1,2,4,5,3H,6H,10H-Tetrahydro-8-trifluoromethyl[1]benzopyrano[9,9a,1-gh]quinolizin-10-one,
FD-16 4-Methyl-7-(sulfomethylamino)coumarin sodium salt,
FD-17 7-Ethylamino-6-methyl-4-trifluoromethylcoumarin,
FD-18 7-Dimethylamino-4-methylcoumarin,
FD-19 1,2,4,5,3H,6H,10H-Tetrahydro-carbethoxy[1]benzopyrano[9,9a,1-gh]quinolizino-10-one,
FD-20 9-Acetyl-1,2,4,5,3H,6H,10H-tetrahydro[1]benzopyrano[9,9a,1-gh]quinolizino-10-one,
FD-21 9-Cyano-1,2,4,5,3H,6H,10H-tetrahydro[1]benzopyrano[9,9a,1-gh]quinolizino-10-one,
FD22 9-(t-Butoxycarbonyl)-1,2,4,5,3H,6H,10H-tetrahyro[1]-benzopyrano-[9,9a,1-gh]quinolizino-10-one,
FD-23 4-Methylpiperidino[3,2-g]coumarin,
FD-24 4-Trifluoromethylpiperidino[3,2-g]coumarin,
FD-25 9-Carboxy-1,2,4,5,3H,6H,10H-tetrahydro[1]benzopyrano[9,9a,1-gh]quinolizino-10-one,
FD-26 N-Ethyl-4-trifluoromethylpiperidino[3,2-g].

Other dopants include salts of bis benzene sulphonic acid (require deposition by spin-coating rather than sublimation) such as

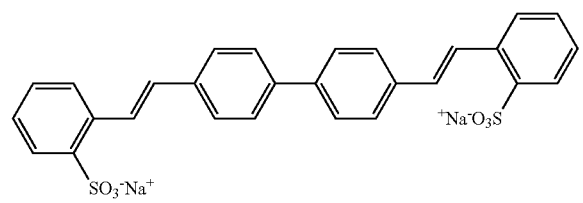

and perylene and perylene derivatives and dopants. Other dopants are dyes such as the fluorescent 4-dicyanomethylene-4H-pyrans and 4-dicyanomethylene-4H-thiopyrans, e.g. the fluorescent dicyanomethylenepyran and thiopyran dyes. Useful fluorescent dyes can also be selected from among known polymethine dyes, which include the cyanines, complex cyanines and merocyanines (i.e. tri-, tetra- and polynuclear cyanines and merocyanines), oxonols, hemioxonols, styryls, merostyryls, and streptocyanines. The cyanine dyes include, joined by a methine linkage, two basic heterocyclic nuclei, such as azolium or azinium nuclei, for example, those derived from pyridinium, quinolinium, isoquinolinium, oxazolium, thiazolium, selenazolium, indazolium, pyrazolium, pyrrolium, indolium, 3H-indolium, imidazolium, oxadiazolium, thiadioxazolium, benzoxazolium, benzothiazolium, benzoselenazolium, benzotellurazolium, benzimidazolium, 3H- or 1H-benzoindolium, naphthoxazolium, naphthothiazolium, naphthoselenazolium, naphthotellurazolium, carbazolium, pyrrolopyridinium, phenanthrothiazolium, and acenaphthothiazolium quaternary salts. Other useful classes of fluorescent dyes are 4-oxo-4H-benz-[d,e]anthracenes and pyrylium, thiapyrylium, selenapyrylium, and telluropyrylium dyes.

Further blue-emitting materials are disclosed in the following patents, applications and publications, the contents of which are incorporated herein by reference:

U.S. Pat. No. 5,141,671 (Bryan, Kodak)—Aluminium chelates containing a phenolato ligand and two 8-quinolinolato ligands.

WO 00/32717 (Kathirgamanathan)—Lithium quinolate which is vacuum depositable, and other substituted quinolates of lithium where the substituents may be the same or different in the 2, 3, 4, 5, 6 and 7 positions and are selected from alky, alkoxy, aryl, aryloxy, sulphonic acids, esters, carboxylic acids, amino and amido groups or are aromatic, polycyclic or heterocyclic groups.

US 2006/0003089 (Kathirgamanathan)—Lithium quinolate made by reacting a lithium alkyl or alkoxide with 8-hydroxyquinoline in acetonitrile.

Misra, http://www.ursi.org/Proceedings/ProcGA05/pdf/DO4.5(01720).pdf Blue organic electroluminescent material bis-(2-methyl 8-quinolinolato) (triphenyl siloxy)aluminium (III) vacuum depositable at $1 \times 10^{-5}$ Torr.

WO 03/006573 (Kathirgamanathan et al)—Metal pyrazolones.

WO 2004/084325 (Kathirgamanathan et al)—Boron complexes.

WO 2005/080526 (Kathitgamanathan et al)—Blue phosphorescent iridium-based complexes.

Ma et al., Chem. Comm. 1998, 2491-2492. Preparation and crystal structure of a tetranuclear zinc(II) compound $[Zn_4O(AID)_6]$ with 7-azaindolate as a bridging ligand. Fabrication of inter alia a single-layer LED by vacuum deposition of this compound (<200° C., $2 \times 10^{-6}$ Torr) onto a glass substrate coated with indium-tin oxide to form a thin homogeneous film was reported.

Further electroluminescent materials which can be used include metal quinolates such as aluminium quinolate, lithium quinolate, titanium quinolate, zirconium quinolate, hafnium quinolate etc.

Many further electroluminescent materials that may be used are disclosed in WO 2004/050793 (pyrazolones), WO 2004/058783 (diiridium metal complexes), WO 2006/016193 (dibenzothiophenyl metal complexes) and WO 2006/024878 (thianthrene metal complexes), see also WO 2006/040593 the contents of which are incorporated herein by reference. Rare earth chelates, in particular may be employed as green and red emitters. Furthermore, there may be used as electroluminescent materials, conducting polymers and conjugated polymers e.g. polyaniline, phenylene vinylene polymers, fluorene homopolymers and copolymers, phenylene polymers, as indicated below:

Further examples of dopants from the class of compounds based on rare earth chelates are:

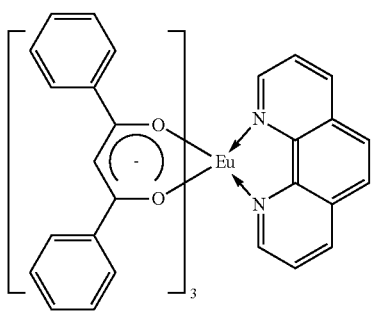

Eu(DBM)₃•Phen

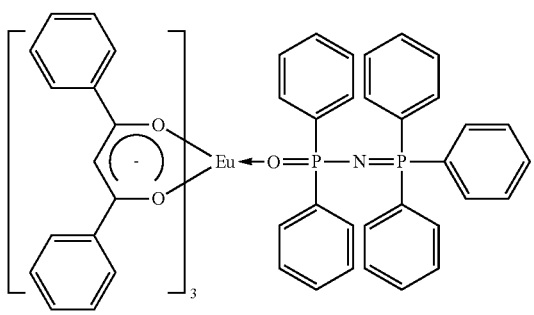

Eu(DBM)₃•OPNP

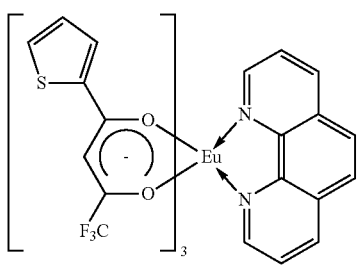

Eu(TTA)₃•Phen

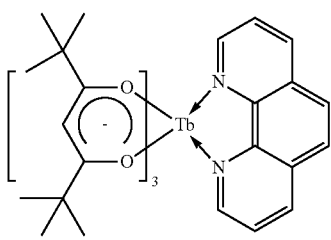

Tb(TMHD)₃•Phen

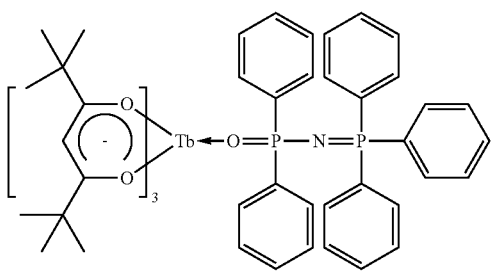

Tb(TMHD)₃•OPNP

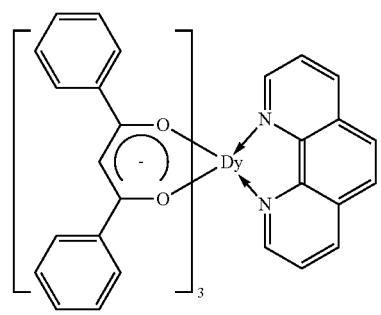

Dy(DBM)₃•Phen

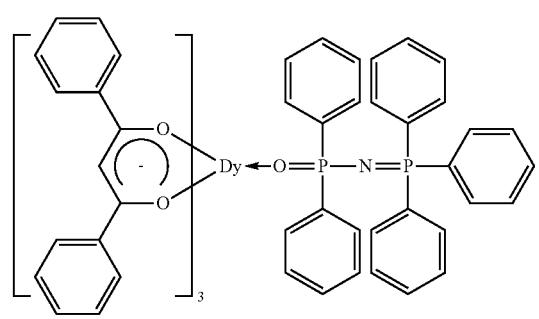

Dy(DBM)₃•OPNP

Furthermore, there may be used as electroluminescent materials conducting polymers e.g phenylene vinylene polymers, fluorene homopolymers and copolymers, phenylene polymers.

Thermally Activated Delayed Fluorescent Material Based Devices

The present invention includes the use of the materials claimed in this invention in OLED devices where the emitter is a thermally activated delayed fluorescent (TDAF) material (For example see Scientific Reports: Hajime Nakantonai et al., *Scientific Reports*, 3:2127, DOI:10.1038/srep02127) the contents of which are incorporated herein by reference.

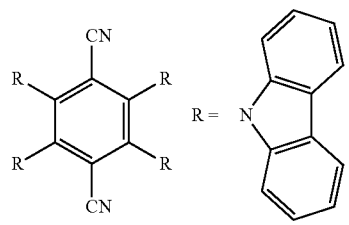

4CzIPN

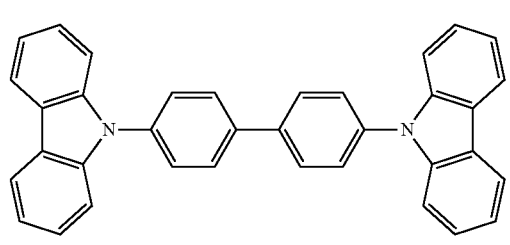

CBP

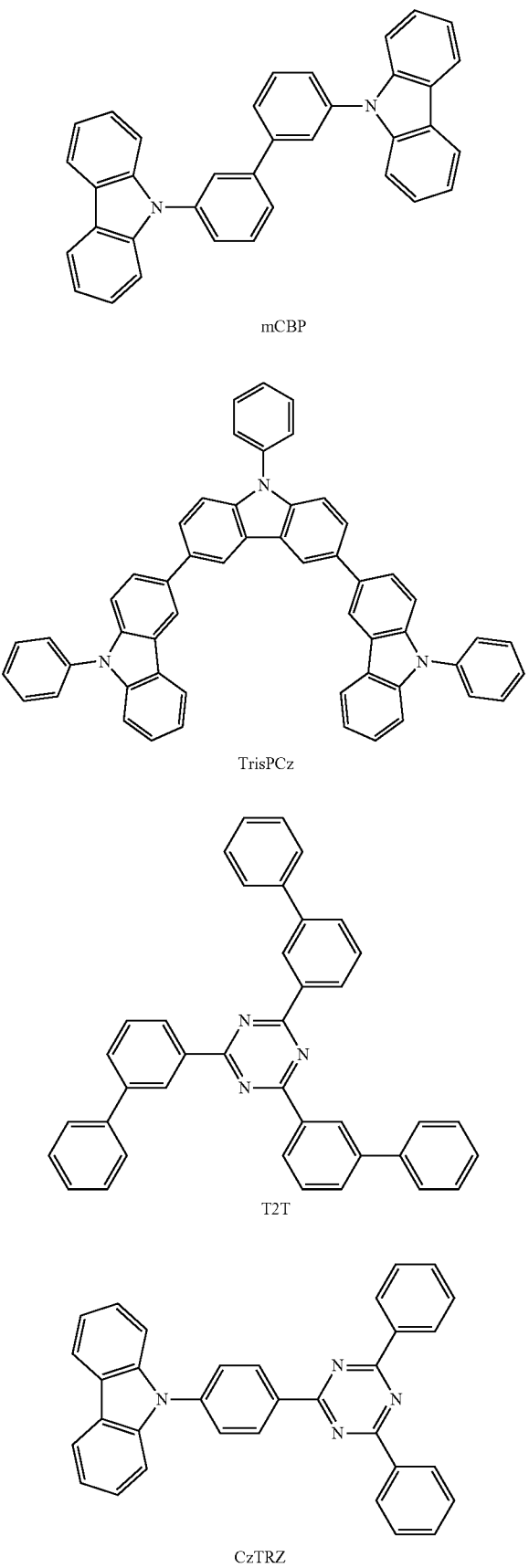

mCBP

TrisPCz

T2T

CzTRZ

Conducting Polymers

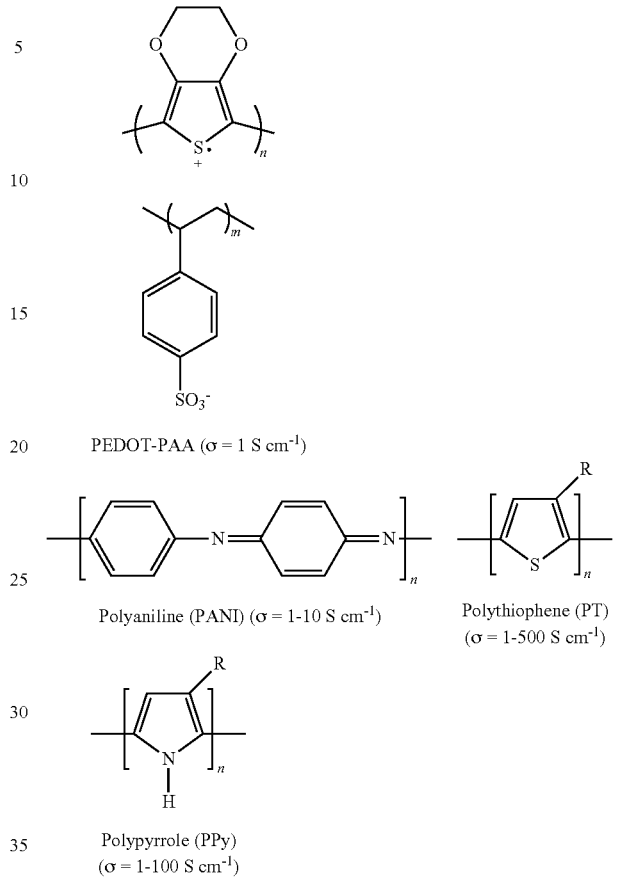

PEDOT-PAA ($\sigma = 1$ S cm$^{-1}$)

Polyaniline (PANI) ($\sigma = 1\text{-}10$ S cm$^{-1}$)

Polythiophene (PT) ($\sigma = 1\text{-}500$ S cm$^{-1}$)

Polypyrrole (PPy) ($\sigma = 1\text{-}100$ S cm$^{-1}$)

Mixed host materials have also been disclosed in the literature and may be used in OLED devices according to the invention. Various references disclose additives and mixed hosts for OLEDs in an attempt to further improve properties. Jarikov et al., *J. Appl. Phys.*, 100, 014901 (2006) discloses flat and rigid polycyclic aromatic hydrocarbons (PAHs) as LEL additives e.g. perylene.

Jarikov et al. further report J. Appl. Phys., 100, pp. 094907-094907-7 (2006) perylene derivatives as light-emitting-layer (LEL) additives in organic light-emitting diodes (OLEDs). These molecules readily form emissive aggregates when added to the LEL. Addition of these polycyclic aromatic hydrocarbons increases the half-life ($t_{50}$) of undoped and doped OLEDs by 30-150 times e.g. in an Alq$_3$+dibenzo[b,k]perylene mixed host. The authors yet further report in *J. Appl. Phys.*, 102, 104908 (2007) a synergistic effect of a lifetime-extending light-emitting-layer (LEL) additive and improved electron injection and transport in organic light-emitting diodes (OLEDs). Di-(2-naphthyl)perylene (DNP) serves as a LEL additive said to extend the operating lifetime of OLEDs by over two orders of magnitude. Using 2-phenyl-9,10-di(2-naphthyl)anthracene (PADN) as an electron-transport layer (ETL) and a separate layer of 4,7-diphenyl-1,10-phenanthroline (BPhen) as an electron-injection layer (EIL) the authors claimed to have significantly improved electron delivery into the charge recombination zone relative to traditional ETL made of tris(8-quinolinolate)aluminium (Alq). See also U.S. Pat. No. 7,175,922 (Jarikov et al) the disclosure of which is incorporated herein by reference.

J. C. Deaton et al (supra) disclose an α-NPB host with a "blue" aluminium quinolate as co-host and an iridium dopant. Very good yields were obtained with low concentrations of dopant for phosphorescent devices and it was found that the mixed host device provided increased power efficiency. It was hypothesized that the explanation was a reduction in the energy barrier to inject holes into the emissive layer by mixing the hole-transporting NPB having an ionization potential of 5.40 eV into the dominantly electron-transporting "blue" aluminium quinolate, having a higher ionization potential of 6.02 eV.

U.S. Pat. No. 6,392,250 (Aziz et al, the disclosure of which is incorporated herein by reference.) discloses organic light emitting devices comprising a mixed region comprising a mixture of a hole transport material e.g. an aromatic tertiary amine, an electron transport material e.g. a quinolate and a dopant material. For example N,N'-di-1-naphthyl-N,N'-diphenyl-1,1'-biphenyl-1,1'-biphenyl-4,4'-diamine (NPB), and tris (8-hydroxyquinoline) aluminium ($Alq_3$) may be used as the hole transport material and the electron transport material, respectively and N,N'-dimethylquinacridone (DMQ), 5,6,11,12-tetraphenylnapthacene (Rubrene), and Nile-red dye (available from Aldrich Chemicals of Milwaukee, Wis.) may be used as dopants.

US 2002/0074935 (Kwong et al) also discloses devices with an emissive layer containing PtOEP or bis(benzothienyl-pyridinato-NΛC)Iridium(III) (acetylacetonate) as a dopant and equal proportions of NPB and Alq as host materials. It is explained that the mixed host electroluminescent mixed layer serves to substantially reduce the accumulation of charge that is normally present at the heterojunction interface of heterostructure devices, thereby reducing organic material decomposition and enhancing device stability and efficiency.

In US 2004/0155238 (Thompson et al.) a light emitting layer of the OLED device contains a wide band gap inert host matrix in combination with a charge carrying material and a phosphorescent emitter. The charge carrying compound can transport holes or electrons, and it is selected so that charge carrying material and phosphorescent emitter transport charges of opposite polarity.

M. Furugori et al. in US 2003/0141809 disclose phosphorescent devices where a host material is mixed with another hole- or electron transporting material in the light emitting layer. The document discloses that devices utilizing plural host compounds show higher current and higher efficiencies at a given voltage.

T. Igarashi et al. in WO 2004/062324 disclose phosphorescent devices with the light emitting layer containing at least one electron transporting compound, at least one hole transporting compound and a phosphorescent dopant.

WO 2006/076092 (Kondakova et al., the contents of which are also incorporated herein by reference) discloses OLED device comprising a cathode, an anode, and located therebetween a light emitting layer (LEL) comprising at least one hole transporting co-host e.g. an aromatic tertiary amine such as 4,4'-Bis[N-(1-naphthyl)-N-phenylamino]biphenyl (NPB), 4,4'-Bis[N-(1-naphthyl)-N-(2-naphthyl) amino]biphenyl (TNB), 4,4'-Bis[N-(3-methylphenyl)-N-phenylamino-]biphenyl (TPD), 4,4'-Bis-diphenylaminoterphenyl or 2,6,2',6'-tetramethyl-N,N,N',N'-tetraphenylbenzidine. and at least one electron transporting co-host e.g. a substituted 1,2,4-triazole such as 3-phenyl-4-(1-naphtyl)-5-phenyl-1,2,4-triazole or a substituted 1,3,5-triazine such as 2,4,6-tris(diphenylamino)-1,3,5-triazine, 2,4,6-tricarbazolo-1,3,5-triazine, 2,4,6-tris(N-phenyl-2-naphthylamino)-1,3,5-triazine, 2,4,6-tris(N-phenyl-1-naphthylamino)-1,3,5-triazine and 4,4',6,6'-tetraphenyl-2,2'-bi-1,3,5-triazine together with a phosphorescent emitter, wherein the triplet energy of each of the co-host materials is greater than the triplet energy of the phosphorescent emitter, and further containing an exciton blocking layer comprising a hole transporting material with triplet energy greater or equal to 2.5 eV adjacent the emitting layer on the anode side, which may be a substituted triarylamine e.g. 4,4',4"-tris[(3-methylphenyl)phenylamino]triphenylamine (MTDATA), 4,4',4"-tris(N,N-diphenyl-amino)triphenylamine (TDATA), N,N-bis[2,5-dimethyl-4-[(3-methylphenyl)-phenylamino] phenyl]-2,5-dimethyl-N'-(3-methylphenyl)-N'-phenyl-1,4-benzenediamine. The devices are said to exhibit improved efficiency and reduced drive voltage.

U.S. Pat. No. 7,045,952 (Lu, Universal Display Corporation) discloses an organic light emissive device comprising an emissive region disposed between and electrically connected to an anode and a cathode, wherein the emissive region comprises (i) a first single-host emissive layer, comprising a first host material, and (ii) a mixed-host emissive layer in direct contact with the first single-host emissive layer, wherein the mixed-host emissive layer comprises the first host material, and a second host material, and wherein the first single-host emissive layer and the mixed-host emissive layer each further comprise a phosphorescent emissive material.

It is believed that cells of the present kind will also operate where the light-emitting layer is based on electroluminescent quantum dots (Nanoco Group PLC) of diameter 1-20 nm, e.g based on CdSe quantum dot cores (emission 480-640 nm) or CdS quantum dot cores (emission 380-480 nm) and cadmium-free electroluminescent quantum dots (see U.S. Pat. No. 7,867,557 Pickett; U.S. Pat. No. 7,588,828 Mushtaq and 2011/0070443 O'Brien, the disclosures of which are incorporated herein by reference). WO 2011/0601180 (Kalzas, QD Vision, Inc) discloses the use of CdSe/CdZnS core-shell particles in a cell having inter alia a zinc oxide electron transport layer and an organic (NPB) hole transport layer. Displays based on quantum dots are expected to exhibit brighter images, lower power consumption, improved colour purity and longer life. Significantly, only a single material is needed to generate a full colour display the emission being tuneable by particle size. Because of the narrow emission bands, a display based on quantum dots are expected to have a wider colour gamut and better colour saturation than current display technologies. Quantum dot LEDs are also expected to be useful in solid state lighting. The present techniques of hole injection, hole transport, electron injection and electron transport are believed to be applicable to a quantum dot electroluminescent layer in the same way as for a current fluorescent or phosphorescent electroluminescent layer.

Electron Transport Material

Known electron transport materials may be used, including, for example, quinolates.

Aluminium quinolate is thermally and morphologically stable to be evaporated into thin films, easily synthesized and purified and is widely used despite its problems of relatively low mobility, bandgap and tendency to ashing during sublimation. As disclosed in patent application WO 2008/078114, improved electron transport materials consist of or comprise zirconium or hafnium quinolate, zirconium quinolate being preferred for many embodiments.

Zirconium quinolate has a particularly advantageous combination of properties for use as an electron transport material and which identify it as being a significant improvement on aluminium quinolate for use as an electron transport material. It has high electron mobility. Its melting point (388° C.) is lower than that of aluminium quinolate (414° C.). It can be purified by sublimation and unlike aluminium quinolate it resublimes without residue, so that it is even easier to use than aluminium quinolate. Its lowest unoccupied molecular orbital (LUMO) is at −2.9 eV and its highest occupied molecular orbital (HOMO) is at −5.6 eV, similar to the values of aluminium quinolate. Furthermore, unexpectedly, it has been found that when incorporated into a charge transport layer it slows loss of luminance of an OLED device at a given current with increase of the time for which the device has been operative (i.e. increases device lifetime), or increases the light output for a given applied voltage, the current efficiency for a given luminance and/or the power efficiency for a given luminance. Embodiments of cells in which the electron transport material is zirconium quinolate can exhibit reduced turn-on voltage and up to four times the lifetime of similar cells in which the electron transport material is zirconium quinolate. It is compatible with aluminium quinolate when aluminium quinolate is used as host in the electroluminescent layer of an OLED, and can therefore be employed by many OLED manufacturers with only small changes to their technology and equipment. It also forms a good electrical and mechanical interface with inorganic electron injection layers e.g. a LiF layer where there is a low likelihood of failure by delamination. Of course zirconium quinolate can be used both as host in the electroluminescent layer and as electron transfer layer. The properties of hafnium quinolate are generally similar to those of zirconium quinolate.

Zirconium or hafnium quinolate may be the totality, or substantially the totality of the electron transport layer. It may be a mixture of co-deposited materials which is predominantly zirconium quinolate. The zirconium or hafnium may be doped as described in GB 06 14847.2 filed 26 Jul. 2006, the contents of which are incorporated herein by reference. Suitable dopants include fluorescent or phosphorescent dyes or ion fluorescent materials e.g. as described above in relation to the electroluminescent layer, e.g. in amounts of 0.01-25 wt % based on the weight of the doped mixture. Other dopants include metals which can provide high brightness at low voltage. Additionally or alternatively, the zirconium or hafnium quinolate may be used in admixture with another electron transport material. Such materials may include complexes of metals in the trivalent or pentavalent state which should further increase electron mobility and hence conductivity. The zirconium and hafnium quinolate may be mixed with a quinolate of a metal of group 1, 2, 3, 13 or 14 of the periodic table, e.g. lithium quinolate or zinc quinolate. Preferably the zirconium or hafnium quinolate comprises at least 30 wt % of the electron transport layer, more preferably at least 50 wt %.

Other examples of electron transporters are shown below:

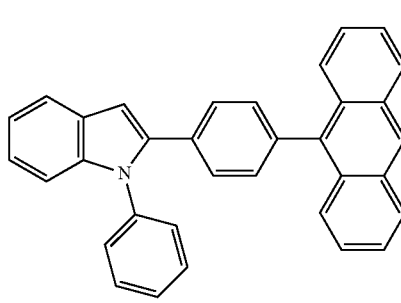

QAPPI

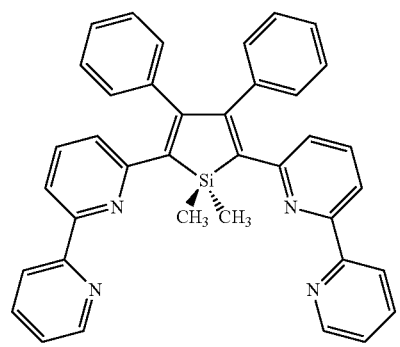

PyPySiPyPy

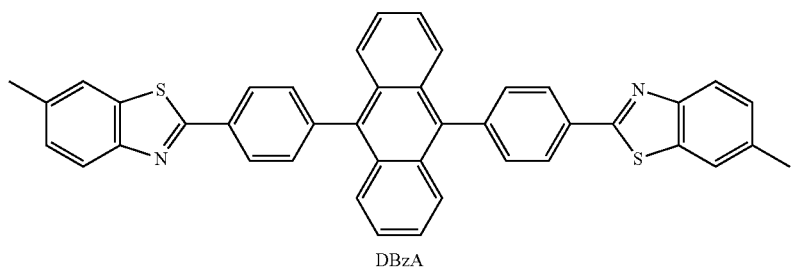

DBzA

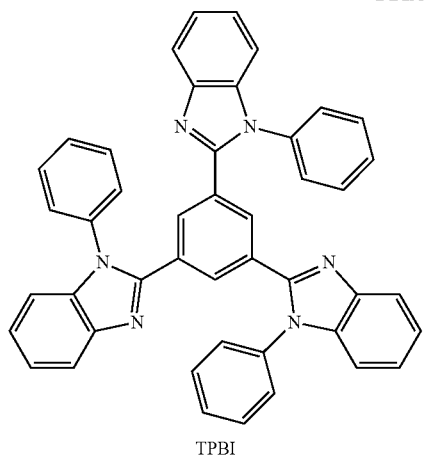

TPBI

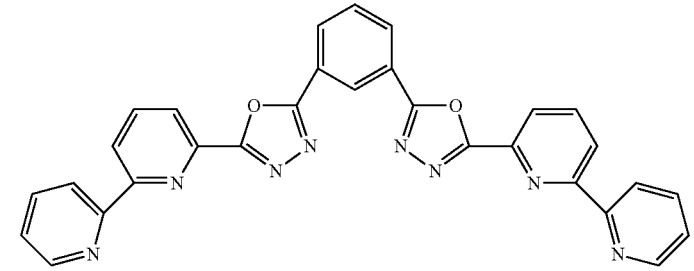

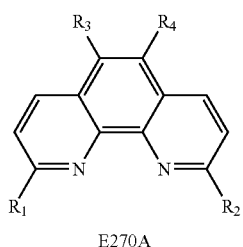

E270A

In embodiments of the invention there may be used ambipolar or electron transporting materials either alone or as a composition co-deposited with an n-type dopant e.g lithium quinolate or another lithium complex mentioned herein.

Compounds that may be used for this purpose have having one or two thianthrene moieties linked to conjugated or aromatic hydrocarbon other than alkyl-substituted fluorine.

Structures of this type (which may be ring-substituted with groups R as defined above but which do not include compounds containing fluorene alkyl-substituted at the 5-membered ring) are set out below (X and Y being S)

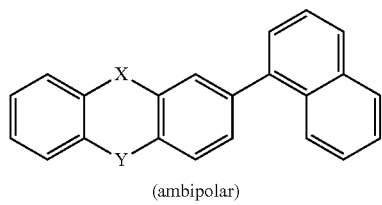

(ambipolar)

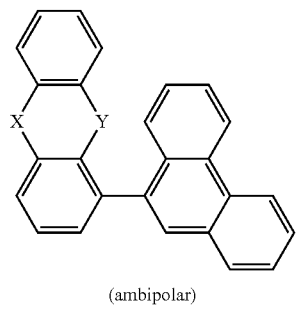

(ambipolar)

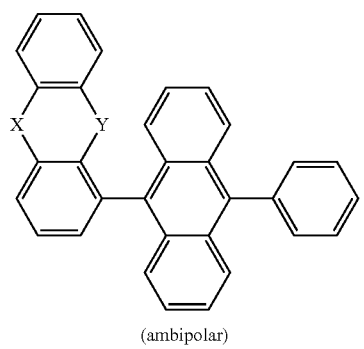

(ambipolar)

-continued

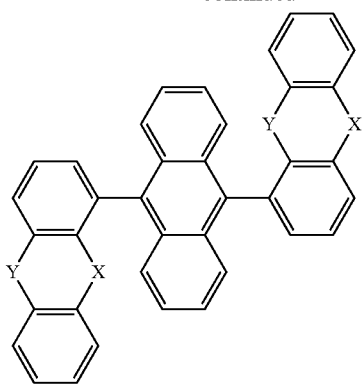

(ambipolar)

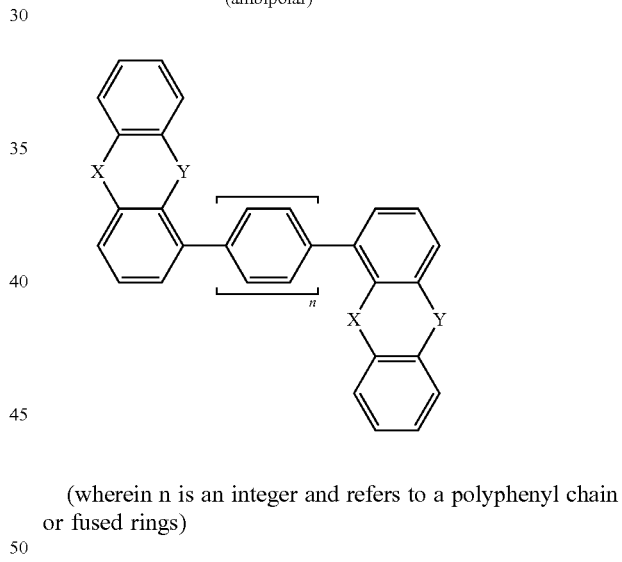

(wherein n is an integer and refers to a polyphenyl chain or fused rings)

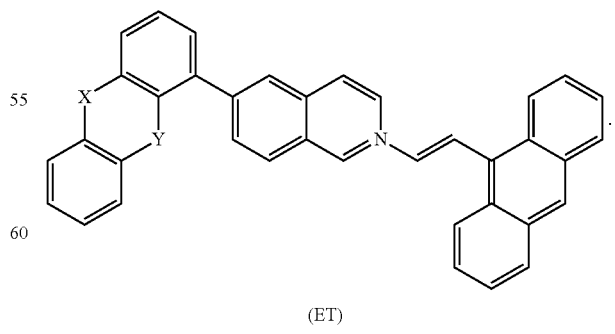

(ET)

The compound 1-phenyl-2-(4-(thianthren-9-yl)phenyl)-1H-benzo[d]imidazole may be made as follows:

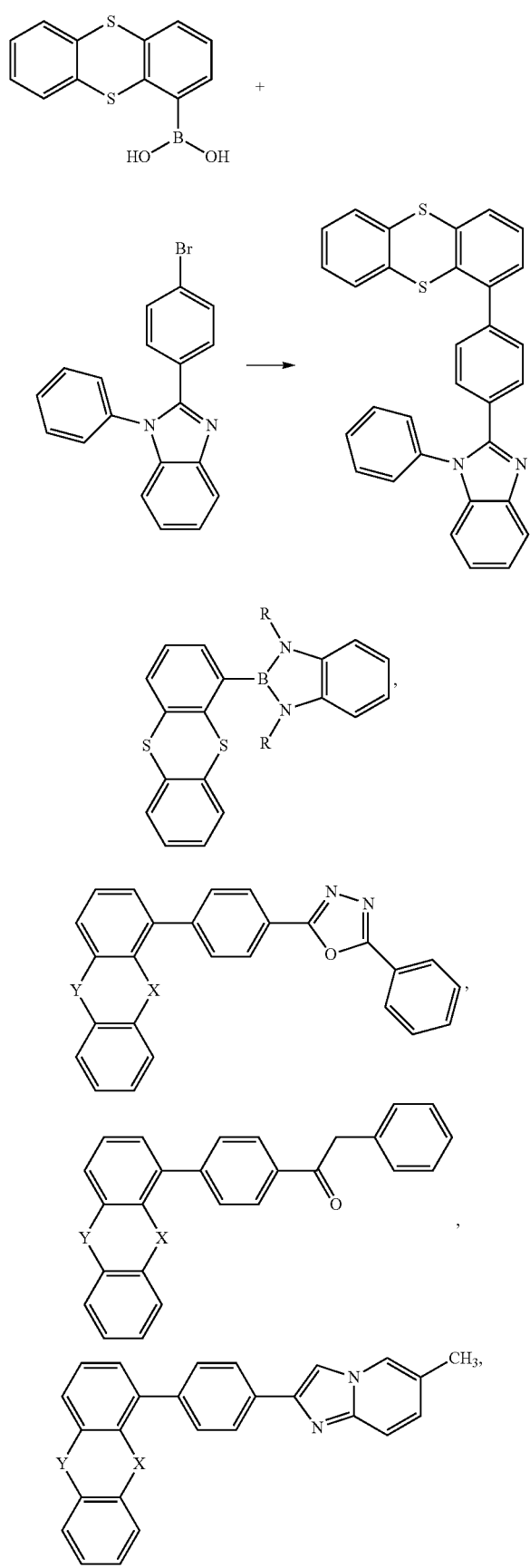

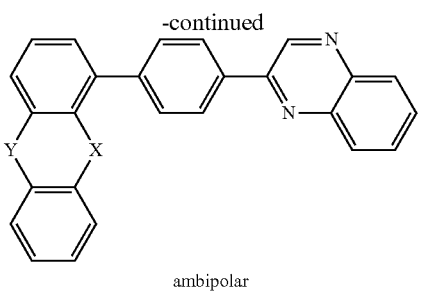

ambipolar wherein X and Y are both S.

The compound may be 1-anthracenyl-9-yl-thianthrene, 1-biphenyl-4-yl-thianthrene or 9,10-Bis (1-thianthrenyl) anthrance. or a mixture thereof. It may be mixed with a low work function metal complex or may be doped with a fluorescent dopant or may be doped with a phosphorescent dopant or may be doped with a rare earth chelate. For example, the compound may be mixed with either a lithium quinolinolate (LiQ) or a lithium Schiff base complex from 1 to 99% by mass, e.g. 10 to 90% by mass, e.g. 20-90% by mass, commonly 30-80% by mass. An aspect of the invention therefore comprises any of the compounds described above in combination with an n-type dopant which may be e.g. any of the lithium compounds described below for the electron injection layer.

Electron Injection Material

Any known electron injection material may be used, LiF being typical. Other possibilities include $BaF_2$, $CaF_2$, CsF, $MgF_2$ and KF.

The electron injection layer is deposited direct onto the cathode and may also comprise a compound of the formula

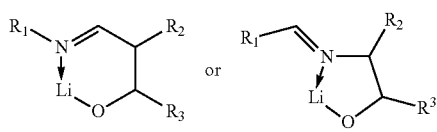

wherein $R_1$ is a 1-5 ring aryl (including polycyclic aryl or aryl-substituted polycyclic aryl), aralkyl or heteroaryl group which may be substituted with one or more $C_1$-$C_4$ alkyl or alkoxy substituents; and $R_2$ and $R_3$ together form a 1-5 ring aryl (including polycyclic or aryl-substituted polycyclic aryl), aralkyl or heteroaryl group which may be substituted with one or more $C_1$-$C_4$ alkyl or alkoxy substituents. A compound of the above formula may be used alone or in combination with another electron injection material e.g. a quinolate such as lithium or zirconium quinolate. The Schiff base preferably comprises at least 30 wt % of the electron injection layer, more preferably at least 50 wt %.

In the formula set out above, $R_1$ may be polycyclic aryl e.g. naphthyl, anthracenyl, tetracenyl, pentacenyl or a perylene or pyrene compound or may have up to 5 aromatic rings arranged in a chain e.g. biphenyl. It is preferably phenyl or substituted phenyl. $R_2$ and $R_3$ together may form the same groups as $R_1$ and are preferably phenyl or substituted phenyl. Where substituents are present they may be methyl, ethyl, propyl or butyl, including t-butyl substituted, or may be methoxy, ethoxy, propoxy or butoxy including t-butoxy substituted. Particular compounds include

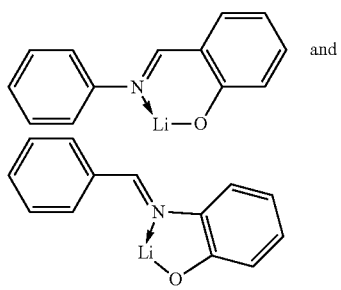

and

Cathode

In many embodiments, aluminium is used as the cathode either on its own or alloyed with elements such as magnesium or silver, although in some embodiments other cathode materials e.g. calcium may be employed. In an embodiment the cathode may comprise a first layer of alloy e.g. Li—Ag, Mg—Ag or Al—Mg closer to the electron injection or electron transport layer and a second layer of pure aluminium further from the electron injection or electron transport layer. Cells in which grapheme serves as cathode are also within the invention.

How the invention may be put into effect will now be described with reference to the following examples.

Example 1

4-(Thianthren-1-yl)triphenylamine (also dDiphenyl-(4-thianthren-1-yl-phenyl)-amine; (HTS-1)

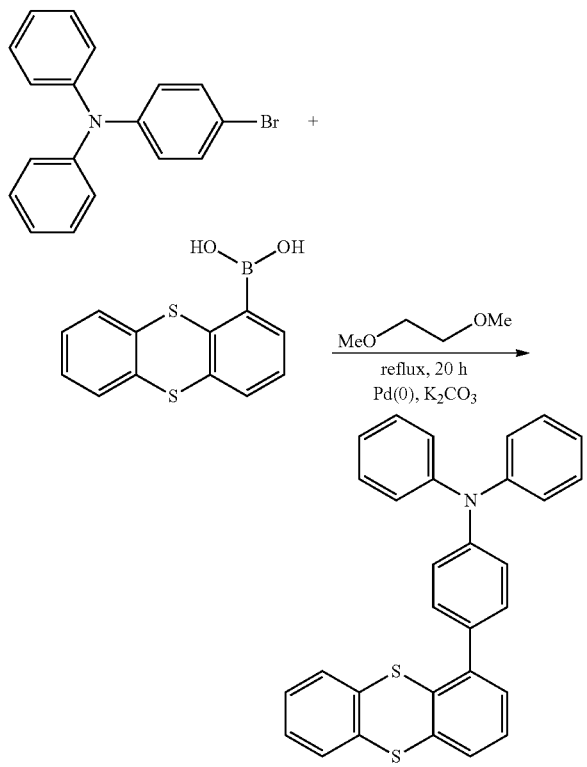

To a mixture of 4-Bromotriphenyl amine (2.0 g; 0.0062 mole), 1-thianthrenylboronic acid (1.9 g; 0.0074 mole), tetrakis(triphenyl phosphine) palladium (0.36 g; 0.00030 mole) in ethyleneglycoldimethyl ether (30 ml) was added potassium carbonate (4.3 g; 0.060 mole) in water (20 ml). The reaction mixture was magnetically stirred, refluxed under nitrogen atmosphere for 20 hours, allowed to cool and then filtered through a short suction column of silica gel and a pad of Hyflosuper gel. The solvent removed from the filtrate, the residue dissolved in dichloromethane and extracted with water. The organic phase was dried over anhydrous magnesium sulphate and solvent removed to give a light green residue. This was again dissolved in dichloromethane adsorbed onto silica gel and then subjected to flash column chromatography over silica gel eluting with dichloromethane. The fractions containing the product were collected together and solvent removed using a rotary evaporator to give a residue which was dissolved in diethyl ether. Addition of small amounts of petroleum ether and cooling in ice water bath gave a clear solid which was dried under vacuum at 80° C., yield 1.95 g (69%). The clear solid was further purified by sublimation to give a colourless glassy solid, 1.3 g (67%), showing light bluish-purple fluorescence under UV.

Found: C, 77.95, H, 4.69, N, 2.88, S, 14.44%.

$C_{30}H_{21}NS_2$, requires C, 78.40, H, 4.61, N, 3.05 and 13.94%.

UV: $\lambda_{max}$ ($CH_2Cl_2$)/nm (S/dm$^3$ mol$^{-1}$ cm$^{-1}$) 313 (22,964) and 261 (30,886).

$\lambda_{max}$ (Thinfilm)/nm: 317, 266 and 203 nm.

Optical band gap: 3.3 eV.

FL: $\lambda_{max}$/nm ($CH_2Cl_2$) em: 417; ex/nm: 350; $\lambda_{max}$/nm (Powder) em: 409, ex/nm: 350; $\lambda_{max}$/nm (Thinfilm) em: 400, ex/nm: 330.

TGA/° C. (% weight loss): 314 (1) and 345 (5).

Example 2

4,4',4"-tri-(thianthren-1-yl)triphenylamine (also tris-(4-thianthren-1-yl-phenyl)-amine; HTS-2)

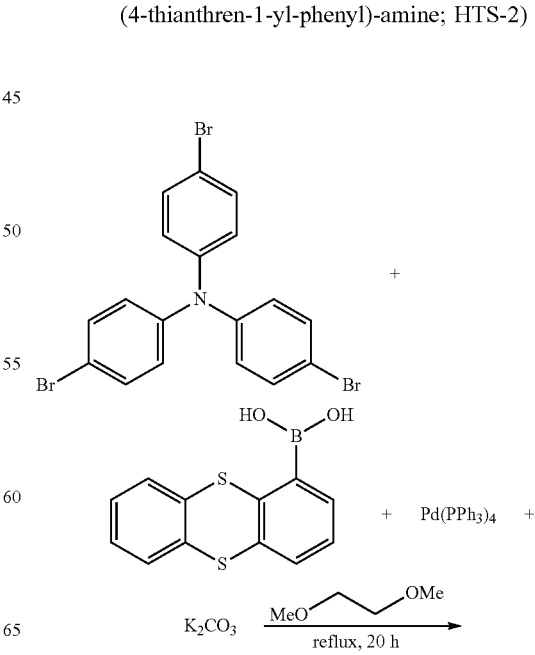

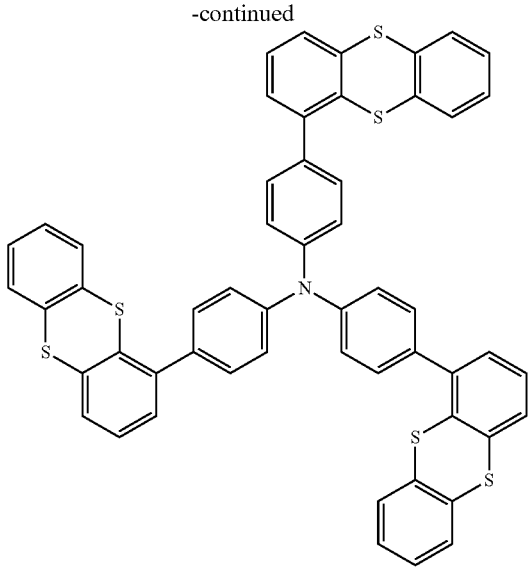

To a mixture of tris(4-bromotriphenylamine) (2.0 g; 0.00415 mole), 1-thianthrenylboronic acid (3.6 g; 0.037 mole), tetrakis(triphenyl phosphine) palladium (0.72 g; 0.00062 mole) in ethyleneglycoldimethyl ether (70 ml) was added potassium carbonate (3.0 g; 0.022 mole) in water (50 ml). The reaction mixture was magnetically stirred and refluxed under nitrogen atmosphere for 20 hours, allowed to cool and the solvent removed under reduced pressure. The residue was dissolved in dichloromethane and extracted with brine (The product was not completely soluble in dichloromethane). The organic phase was washed with water, dried over anhydrous magnesium sulphate and solvent removed to give a green solid. To the solid methanol was added, stirred for 6 h and filtered off under suction. The product was washed with diethyl ether and dried under vacuum at 70° C. Crude yield 3.15 g.

Example 3

9-(4-Bromo-phenyl)-9H-carbazole

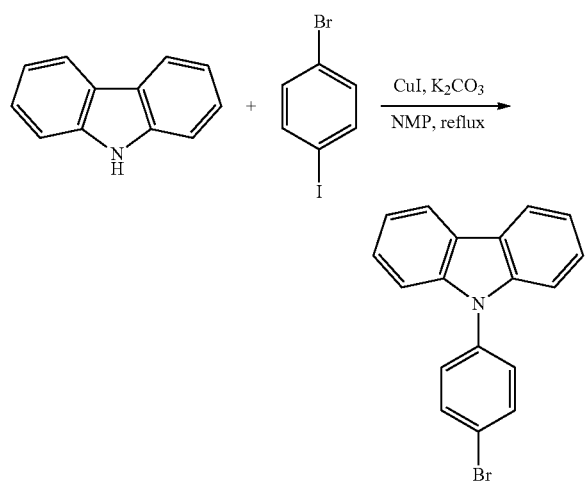

A mixture of carbazole, 95% (5 g; 0.03 mole), 4-iodobromobenzene, 98% (16.9 g; 0.06 mole), copper(I) iodide, 98% (2.8 g; 0.015 mole) and potassium carbonate (8.3 g; 0.06 mole) in 1-methyl-2-pyrrolidinone, 99+% (60 ml) was refluxed under a nitrogen atmosphere for 20 h. After 10 minutes the reaction mixture turned blue-green in colour. The solvent was removed under reduced pressure and the residue was dissolved in 1M HCl and extracted with dichloromethane. The red dichloromethane solution was washed thoroughly with brine, water dried over anhydrous magnesium sulphate and solvent removed to give a red crystalline solid which was purified by column chromatography over silica gel (eluent $CH_2Cl_2$). The fractions containing the product were collected together and solvent removed to give a red solid. Trituration with petroleum ether gave an off-white solid which was suction filtered, washed with diethyl ether and dried under vacuum at 75° C. The filtrate was evaporated and triturated with methanol-diethyl ether to give small amounts of further product. Yield 7.2 g (75%). M.p 132° C. (DSC, onset).

9-(4-Thianthren-1-yl-phenyl)-9H-carbazole (HTS-003)

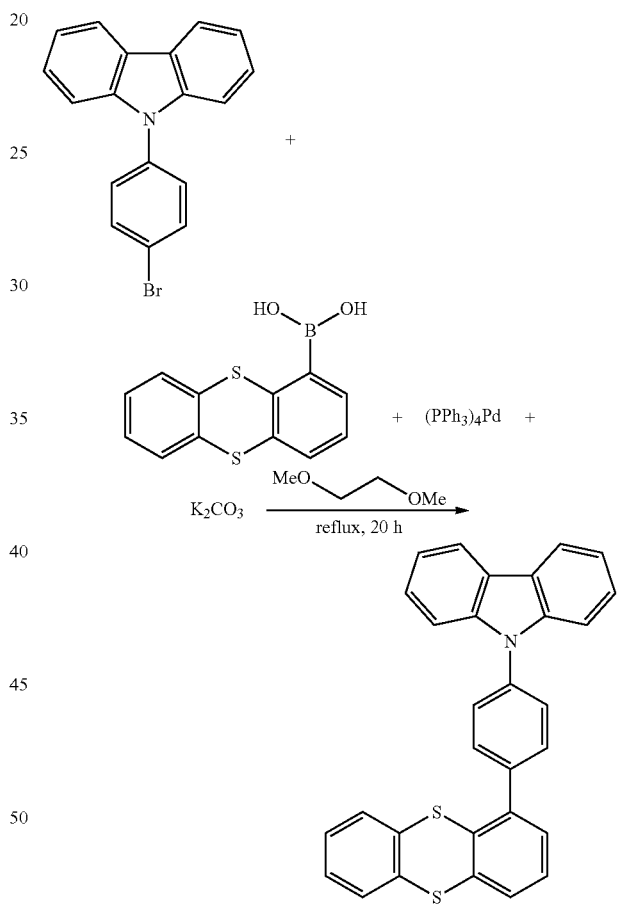

To mixture of 9-(4-Bromophenyl)-9H-carbazole 95.0 g; 0.0155 mole) and tetrakis(triphenylphosphine) palladium (0.9 g; 0.00078 mole) in dimethoxyethane (70 ml) was added thianthrene-1-boronic acid (4.4 g; 0.017 mole), followed by potassium carbonate (10.7 g; 0.078 mole) in water (50 ml). The reaction mixture was magnetically stirred and refluxed under nitrogen for 20 h during which it became green in colour. The solvent was removed and the residue was dissolved in dichloromethane (250 ml) and extracted with water. The organic phase was dried over anhydrous magnesium sulphate and solvent removed to give a dark green solid. Methanol and petroleum ether was added to the solid and the solution was magnetically stirred for 15 minutes, suction filtered and washed with diethyl ether to give an off-white solid, 5.25 g. The product was purified by sublimation at 240° C. (2.5×10-6 torr) to give a white crystalline solid, 4.1 g (78%).

M.p 233° C., Tg 92° C.

Elemental Analysis:

Found, C, 78.70, H, 4.12, N, 3.07, S, 14.27.

$C_{30}H_{19}NS_2$ requires C, 78.74, H, 4.18, N, 3.06 and S, 14.02%.

Example 4

4,4'-di-(thianthren-2-yl)triphenylamine (phenyl-bis (4-thianthren-1-yl-phenyl)-amine; HTS-004)

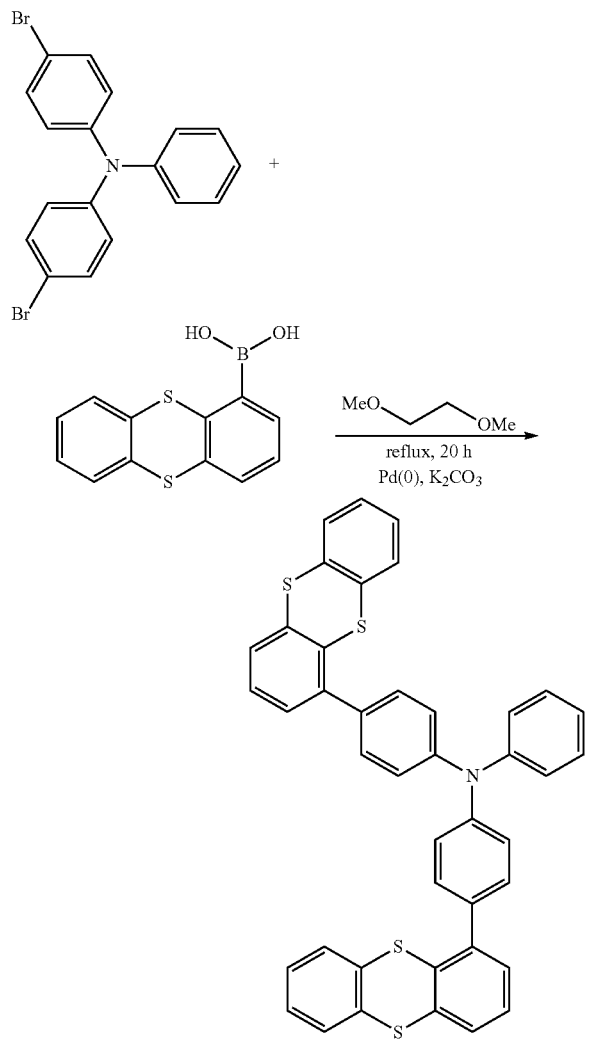

To a mixture of 4,4'-dibromotriphenylamine (5.0 g; 0.0124 mole), 1-thianthrenylboronic acid (7.1 g; 0.0273 mole), tetrakis(triphenyl phosphine) palladium (1.4 g; 0.0012 mole) in ethyleneglycoldimethyl ether (60 ml) was added potassium carbonate (17.2 g; 0.124 mole) in water (40 ml). The reaction mixture was magnetically stirred and refluxed under a nitrogen atmosphere for 20 hours, allowed to cool and the solvent was removed under reduced pressure. The residue was dissolved in dichloromethane and extracted with water. The organic phase was dried over anhydrous magnesium sulphate and solvent removed to give a light green residue which was again dissolved in dichloromethane, adsorbed onto silica gel and then subjected to flash column chromatography over silica gel eluting with dichloromethane. The fractions containing the product were collected together and solvent removed using a rotary evaporator to give a residue which was triturated with methanol and addition of small amounts of petroleum ether. Cooling in an ice water bath gave a pale yellow solid which was dried under vacuum at 80° C., yield 7.4 g (88%). It was further purified twice by sublimation to give a light yellow glassy solid, 2.4 g (33%), showing light bluish fluorescence under UV. DSC did not show any melting peak, but it showed a $T_g$ at 122° C.

Found: C, 74.76, H, 4.12, N, 2.03, S, 19.04%.

$C_{42}H_{27}NS_4$, requires C, 74.85, H, 4.04, N, 2.08, S, 19.03%.

UV: $\lambda_{max}$ ($CH_2Cl_2$)/nm (c/dm$^3$ mol$^{-1}$ cm$^{-1}$) 328 (37,515) 261 (68,620) and 232 (sh)(40,368). $\lambda_{max}$ (Thin film)/nm: 336, 266 and 199 nm.

Optical band gap: 3.24 eV.

FL: $\lambda_{max}$/nm ($CH_2Cl_2$) em: 418; ex/nm: 330; $\lambda_{max}$/nm (Powder) em: 419, ex/nm: 330; $\lambda_{max}$/nm (Thin film) em: 409, ex/nm: 330.

TGA/° C. (% weight loss): 420 (1) and 466 (5).

Example 5

Device Structure

A pre-etched ITO coated glass piece (10×10 cm$^2$) is used. The device is fabricated by sequentially forming layers on the ITO, by vacuum evaporation using a Solciet Machine, ULVAC Ltd. Chigasaki, Japan. The active area of each pixel is 3 mm by 3 mm. The coated electrodes are encapsulated in an inert atmosphere (nitrogen) with UV-curable adhesive using a glass back plate. Electroluminescence studies are performed with the ITO electrode always connected to the positive terminal. The current vs. voltage studies are carried out on a computer controlled Keithly 2400 source meter.

Devices with green emitters are formed by the method described above consisting of an anode layer, buffer layer, hole transport layer, electroluminescent layer (DPQA doped metal complex), electron transport layer, electron injection layer and cathode layer, film thicknesses being in nm:

ITO (100 Ohms per square)/ZnTp TP (E9363, 20 nm)/Compound (HTS-1)(100 nm)/Alq$_3$:DPQA (40:0.1 nm)/Alq$_3$ (20 nm)/Liq (6 nm)/Al        Device A wherein DPQA is diphenyl quinacridone of formula:

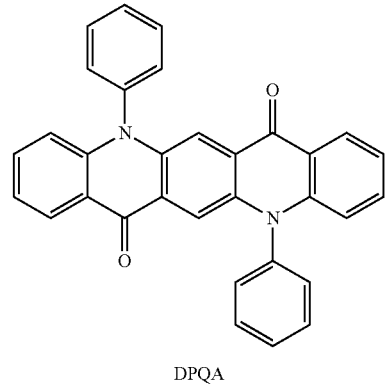

DPQA

ITO (100 Ohms per square)/ZnTp TP (E9363, 20 nm)/α-NPB (100 nm)/Alq$_3$:DPQA (40:0.1 nm)/ Alq$_3$ (20 nm)/Liq (6 nm)/Al        Device B wherein DPQA is diphenyl quinacridone.

Compared to where α-NPB (Device B) is used, devices according to the invention exhibit lower operating voltages and greater stability for devices (Device A) with HTS-1 as shown in FIGS. 1-6.

Similar results are obtained with the red phosphorescent device shown in FIGS. 7-10, the dopant in the electroluminescent layer being tris(1-phenyl-isoquinolinato-$C_2$,N) iridium of formula:

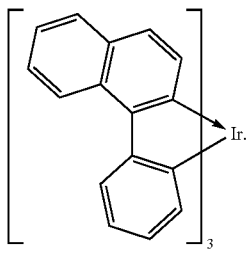

Example 6 (Reference)

4-(10H-phenothiazin-10-yl)triphenylamine (N-(4-(10H-phenothiazin-10-yl)phenyl)-N-phenylbenzenamine; HTS-5)

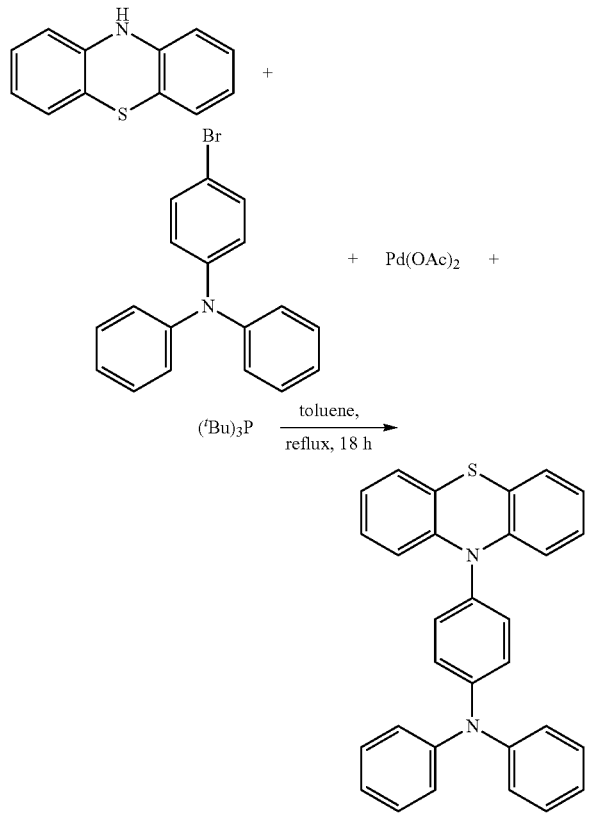

To a solution of 4-bromotriphenylamine (5.0 g; 0.0154 mole) in toluene (40 ml) was added palladium acetate (0.35 g; 0.00156 mole). After magnetically stirring for 5 min, phenothiazine (3.4 g; 0.017 mole) in toluene (20 ml) was added followed by tert-butyl phosphine (6.3 ml: 0.0031 mole). Finally sodium tert-butoxide (4.45 g; 0.046 mole) and toluene (20 ml) were added. The reaction mixture was magnetically stirred and refluxed under nitrogen. After, one hour reflux the reaction mixture became dark and viscous and therefore further toluene (50 ml) was added to the reaction mixture which was then refluxed for a further sixteen hours. Solvent was removed under reduced pressure and the residual oil was cooled to give a crystalline solid which was filtered off, washed with methanol, diethyl ether and petroleum ether, and dried under vacuum at 75° C. The solid (yield 4.1 g) exhibited a bluish fluorescence. The filtrate was evaporated; residue dissolved in small amounts of dichloromethane and passed through a column of silica gel, after which the column was eluted in dichloromethane. Fractions containing the product were evaporated and to the residue petroleum ether (40-60° C.) was added to give an off-white solid. It was separately dried under vacuum. Yield 1.23 g. Tlc examination showed the presence of some phenothiazine. The crystalline solid was sublimed to give colourless to light pink solid.

The compound melts into a liquid and then sublimes. M.p 187° C.; Tg 67° C.

Found: C, 81.29; H, 4.97; N, 6.41, and S, 71.12.

$C_{30}H_{22}N_2S$ requires C, 81.42; H, 5.01; N, 6.33 and S, 7.24%.

UV: λmax/nm (λ) ($CH_2Cl_2$); 307 (28,712), and 259 (46,691);

UV: λmax/nm (thin film); 310 and 262; Band gap: 3.49 eV

FL: λmax/nm (ε) ($CH_2Cl_2$); 448 (excitation wavelength: 330 nm),

λmax/nm (ε) (powder) 443 (excitation wavelength: 330 nm);

λmax/nm (ε) (thin film), 449, (excitation wavelength: 330 nm).

CV: electrolyte (100 mM-Tetrabutylammonium tetrafluoroborate), analyte (1 mM), solvent-dichloromethane: HOMO: −5.5 eV and LUMO: −2.0 eV calculated from optical absorption edge of the thin film.

In this compound the HOMO level is similar to that of α-NBP but the LUMO level of 2.0 eV is low compared to that of other compounds, the LUMO level of α-NBP, for example, being 2.4 eV. For that reason in addition to potential use as a hole transport layer, the above compound may also find use as part or all of a host material in an electroluminescent layer or as part or all of an electron transport layer.

Example 7

HTS-7

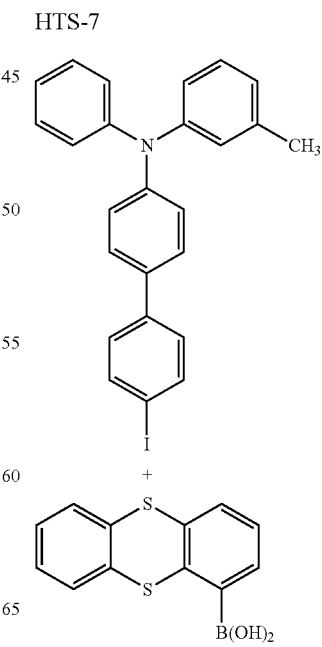

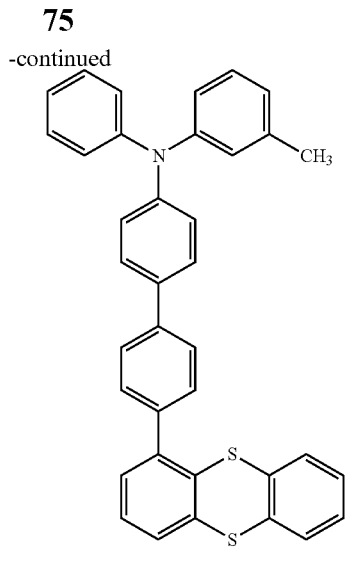

To a mixture of 1-thianthrenylboronic acid (0.62 g; 0.0024 mole), N-(4'-iodophenyl-4-yl)-N-(m-tolyl)aniline (1.0 g; 0.0022 mole) and tetrakis(triphenylphosphine) palladium (0.125 g; 108 mmol) in 1,2-dimethoxy ethanol (30 ml) was added potassium carbonate (1.5 g; 0.011 mole) in water (15 ml). The reaction mixture was magnetically stirred and refluxed under nitrogen for 18 hours. Solvent was removed from the reaction mixture and the residue was extracted with dichloromethane and water. The organic phase was washed with water, dried over anhydrous magnesium sulphate and solvent removed to give an oil which was purified by column chromatography using dichloromethane-petroleum ether (40-60° C.) (85:15) to give light orange fractions. Eluents containing the product were evaporated to give a viscous solid which was recrystallised from methanol-petroleum ether (40-60° C.) to give a yellow solid which was filtered off and dried under vacuum at 75° C., to give 1.0 g (83%) of the required product which was further purified by sublimation at 300° C. ($1.6 \times 10^{-6}$ torr) to give a light yellow glassy solid. No melting peak was observed on DSC, but Tg was at 84° C. It exhibited intense bluish violet fluorescence under a UV lamp.

Found: C, 81.24; H, 4.53; N, 2.71.

$C_{37}H_{27}NS_2$ requires C, 80.84; H, 4.95; N, 2.55%.

UV: λmax/nm (λ) (CH$_2$Cl$_2$); 344 (29,362), 262 (38,576) and 212 (20,834);

UV: λmax/nm (thin film); 349 and 266; Band gap: 3.15 eV

FL: λmax/nm (ε) (CH$_2$Cl$_2$); 441 (excitation wavelength: 350 nm),

λmax/nm (ε) (powder) 423 (excitation wavelength: 350 nm);

λmax/nm (ε) (thin film), 428, (excitation wavelength: 350 nm).

CV: electrolyte (100 mM-Tetrabutylammonium tetrafluoroborate), analyte (1 mM), solvent-dichloromethane: HOMO: −5.7 eV and LUMO: −2.54 eV Calculated from optical absorption edge of the thin film;

TGA/° C. (% weight loss): 382 (1) and 430 (5).

Example 8

2,8-Bis(1-thianthrenyl)dibenzothiophene [HTS-8]

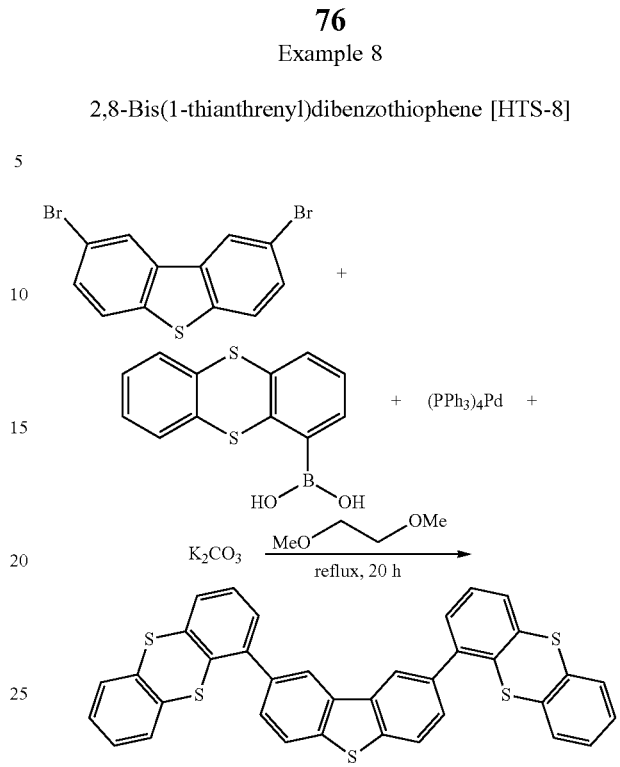

To a solution of 2,8-Dibromodibenzothiophene (1.0 g; 2.9 mmol) in ethyleneglycol dimethyl ether (50 ml) at 60° C. was added 1-thianthreneboronic acid (1.6 g; 6.1 mmol) and tetrkis(triphenylphosphine)palladium (0.34 g; 0.29 mmol) followed by a solution of potassium carbonate (3.2 g; 23 mmol) in water (20 ml). The reaction mixture slowly darkened and became greenish in colour. It mixture was magnetically stirred and refluxed under nitrogen for 20 hours, after which solvent was removed from the cooled reaction mixture under reduced pressure. The residue was dissolved in dichloromethane (150 ml), extracted with water and then brine, after which the organic phase was dried over anhydrous magnesium sulphate. Removal of the solvent gave a greenish residue which was purified by column chromatography over silica gel using dichloromethane-petroleum ether (40-60° C.) (4:1) as eluent. A crude product was obtained by trituration with diethyl ether-petoleum ether (40-60° C.) to give an off white solid, (1.3 g; 73%) and further purified by sublimation at 300° C. ($1.6 \times 10^{-6}$ barr) to give a glassy solid, 0.48 g which did not show any melting peak on the DSC. Tg 133° C.

Found: C, 70.10; H, 3.41; S, 26.53.

$C_{36}H_{20}S_5$ requires C, 70.55; H, 3.29; S, 26.16%.

UV: λmax/nm (ε) (CH$_2$Cl$_2$); 294 (sh)(30,989), 263 (97,473) and 230 (35,934);

UV: λmax/nm (thin film); 303 and 268; Band gap: 3.85 eV

FL: λmax/nm (ε) (CH$_2$Cl$_2$); 441 (excitation wavelength: 350 nm),

λmax/nm (ε) (powder) 439 (excitation wavelength: 350 nm);

λmax/nm (ε) (thin film), 434, (excitation wavelength: 350 nm).

CV: electrolyte (100 mM-Tetrabutylammonium tetrafluoroborate), analyte (1 mM), Solvent-dichloromethane: HOMO: −6.06 eV and LUMO: −2.2 eV Calculated from optical absorption edge of the thin film;

TGA/° C. (% weight loss): 486 (5) and 510 (10).

Example 9

1-(3-Carboxaldehde phenyl)-thianthrene

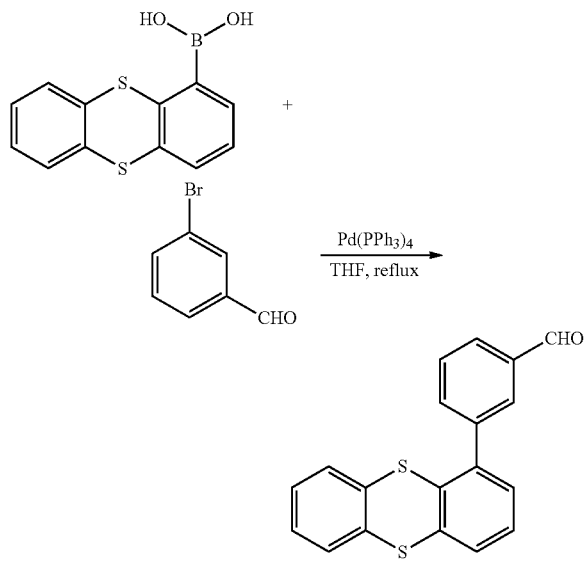

To a mixture of 3-bromobenzaldehyde (1.4 g; 7.57 mmole) and tetrakis(triphenylphosphine) palladium (0.5 g; 0.43 mmole) in tetrahydrofuran (100 ml) was added thianthrene-1-boronic acid (2.0 g; 7.69 mmole), followed by sodium hydrogencarbonate (3.0 g; 35.7 mmole) in water (50 ml). The reaction mixture was magnetically stirred and refluxed under nitrogen for 20 h. The cooled reaction mixture was poured into water and extracted with ethyl acetate. The organic phase was dried over anhydrous magnesium sulphate and solvent removed to give a crude product, which was purified by column chromatography (toluene) to give the pure product, 1.6 g (66%).

Bis [3-(phenylvinyl-1-thianthrenyl)]-4,4'-biphenyl (HTS-9)

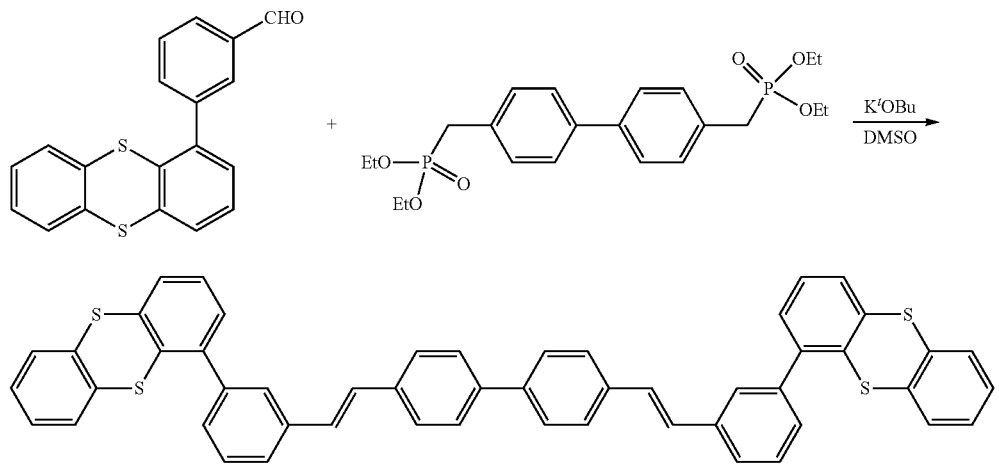

To a solution of biphenyl-bis(methyldiethyl phosphinate) ester (0.43 g; 1.04 mmol) in dimethyl sulphoxide (20 ml) was added potassium tert-butoxide (0.34 g; 3 mmol) followed by 1-(3-carboxaldehde phenyl)-thianthrene (0.7 g; 2.19 mmol). The reaction mixture was stirred at room temperature under argon atmosphere for eighteen hours and the product suction filtered and washed with methanol and petroleum ether to give a solid 0.62 g. The product was purified by sublimation to give a yellow solid, 0.3 g, M.p 259° C. (DSC), Tg 104° C.

Elemental Analysis:
Found, C, 79.69, H, 4.24.
$C_{52}H_{34}S_4$ requires, C, 79.35, H, 4.3%.
Fluorescence (powder): λmax (emission): 474 nm; excitation wavelength, 340 nm.
Fluorescence (dichloromethane): λmax (emission): 428 and 407 nm; excitation wavelength, 340 nm.

Example 10

Cells were made having the structures shown in FIGS. 11-14 and gave the electro-optic properties shown in those figures. The compound HTS-8 exhibited a favourable combination of properties with performance similar to or better than α-NPB and with a relatively high glass transition temperature.

Example 11

1-Anthracen-9-yl-thianthrene (ETS-1)

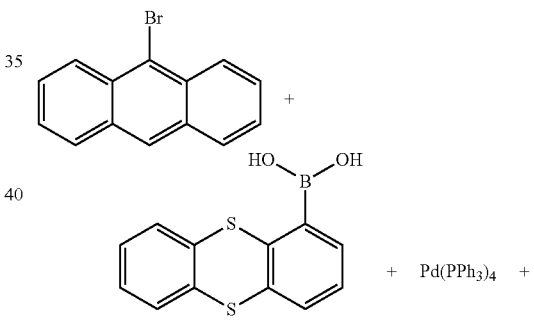

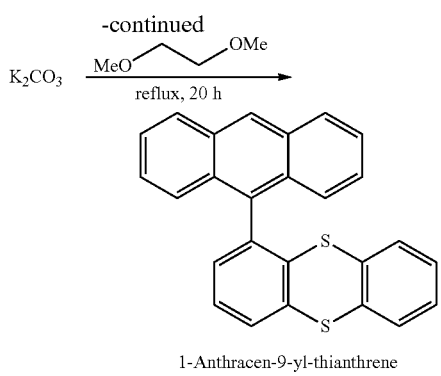

1-Anthracen-9-yl-thianthrene

To a mixture of 9-Bromoanthracene, (Aldrich, 94%) (2.0 g; 0.0078 mole), tetrakis(triphenyl phosphine) palladium (0.45 g; 0.00039 mole) in ethylene glycol dimethyl ether (50 ml) was added 1-thianthrenylboronic acid (2.4 g; 0.0092 mole) and ethyleneglycol dimethyl ether (10 ml), followed by potassium carbonate (5.4 g; 0.039 mole) in water (25 ml). The reaction mixture was magnetically stirred and refluxed under nitrogen atmosphere for 20 hours. It was allowed to cool and the solvent removed under reduced pressure. The residue was dissolved in dichloromethane and extracted with brine. The organic phase was washed with water, dried over anhydrous magnesium sulphate and solvent removed to give a residue to which methanol was added, cooled and magnetically stirred to give a light yellow solid. The product was filtered off under suction washed with methanol, petroleum ether and dried under vacuum at 70° C. Yield 1.65 g. TLC examination (CH$_2$Cl$_2$) showed a single spot. The product was sublimed to give a light yellow solid, M.p 220° C.

Elemental Analysis:
Found, C, 79.38, H, 4.10, S, 16.44.
C$_{26}$H$_{26}$S$_2$ requires, C, 79.56, H, 4.11 and S, 16.33%.

Example 12

1-Biphenyl-4-yl-thianthrene (ETS-2)

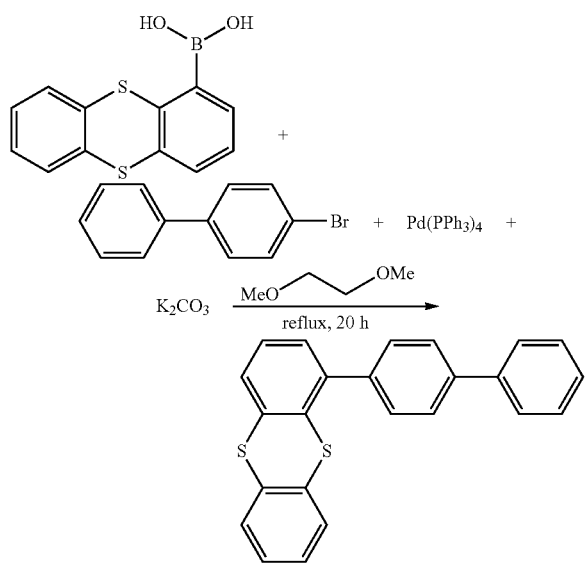

To a mixture of 4-Bromobiphenyl, (Aldrich,) (2.0 g; 0.0086 mole), tetrakis(triphenyl phosphine) palladium (0.5 g; 0.00043 mole) in ethylene glycol dimethyl ether (40 ml) was added 1-thianthrenylboronic acid (2.0 g; 0.0092 mole) {actual amount should be 2.5 g; 0.0094 mole} and ethyleneglycol dimethyl ether (10 ml), followed by potassium carbonate (5.4 g; 0.039 mole) in water (25 ml). The reaction mixture was magnetically stirred and refluxed under nitrogen atmosphere for 20 hours. It was allowed to cool and the solvent removed under reduced pressure. The residue was dissolved in dichloromethane and extracted with brine. The organic phase was washed with water, dried over anhydrous magnesium sulphate and solvent removed to give a residue to which methanol was added, cooled and magnetically stirred overnight to give a light brown solid. The product was filtered off under suction washed with methanol, diethyl ether and dried under vacuum at 70° C. to give an off-white solid, 1.69 g. The product was further purified by sublimation 200° C. (3×10$^{-6}$ torr) to give a colourless solid which exhibited bluish fluorescence under UV. M.p 184° C. (DSC, onset).

Example 13

9,10-Bis (1-thianthrenyl) anthracene

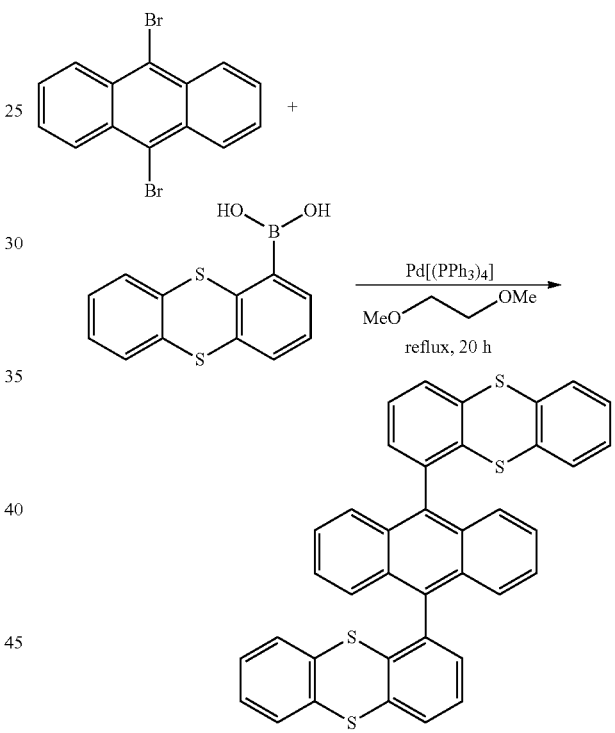

To a magnetically stirred solution of 9,10-dibromoanthracene (5.0 g; 0.015 mole) in ethylene glycol dimethyl ether (100 ml), tetrakis(triphenyl phosphine)palladium (1.9 g; 0.0016 mole) was added followed by 1-thianthrenyboronic acid (8.5 g; 0.033 mole). Potassium carbonate (12.4 g; 0.090 mole) in water (50 ml) was then added and the reaction mixture was refluxed under nitrogen atmosphere for 20 hours. After 15 minutes, the reaction mixture became yellow green in colour. The solvent was removed under reduced pressure and the residue was dissolved in dichloromethane and extracted with dilute acid. (The layers were not easily separable without the addition of acid).

The organic phase was washed with water, dried over anhydrous magnesium sulphate and the solvent filtered through a pad of silica gel. After the removal of the solvent, methanol was added to the residue and stirred at room temperature overnight to give a greenish black solid which was dried under vacuum at 80° C. Yield 6.0 g TLC examination showed a single product which was purified by sublimation to give a dark yellow solid that exhibited intense yellow fluorescence under UV. It was then further purified by double sublimation. The first sublimation gave 2.1 g of the product and the second sublimation gave 1.45 g of the product. M. p 381° C. (DSC, onset), Tg 149° C.

Elemental Analysis:

Found: C, 75.34; H, 3.88, and S, 21.44.

$C_{38}H_{22}S_4$, requires: C, 75.21; H, 3.65, and S, 21.14%.

UV ($CH_2Cl_2$): $\lambda_{max}$ ($\epsilon/M^{-1}$ $cm^{-1}$), 259 (133,155), 342 (4107), 359 (8929), 379 (15,119) and 400 (14,940). UV (Thin film): $\lambda_{max}$ (Abs): 196 (1.47), 266 (1.45), 364 (0.16), 384 (0.245) and 406 (0.25), Film thickness: ~60 nm.

FL ($CH_2Cl_2$) $\lambda_{max}$ (em): 431, excitation wavelength: 350 nm.

FL (Powder)) $\lambda_{max}$ (em): 442, 465 (sh), 508 and 540 (sh).

FL (Thin film) $\lambda_{max}$ (em): 422 (sh), 439 and 500 (sh).

CV ($CH_2Cl_2$): electrolyte: Tetrabutylammonium tetrafluoroborate (100 mM), analyte (1 mM).

Optical band gap: 2.9 ev; HOMO: −6.0 eV and LUMO: −3.1 eV.

TGA/° C. (% weight loss): 400 (1) and 433 (5).

Physical Properties and Fluorescence characteristics of the compounds in Examples 11-13 are summarised in the following Table.

| Code | Compound | Melting point/° C. DSC (onset) | Tg/° C. |
|---|---|---|---|
| ETS-1 | | 220 | 76 |
| ETS-2 | | 184 | — |
| ETS-3 | | 381 | 149 |

| Code | Compound | HOMO/eV | LUMO/eV | Band Gap/eV |
|---|---|---|---|---|
| ETS-1 | | −5.95 | −2.95 | 3 |
| ETS-2 | | −6.05 | −2.25 | 3.80 |

-continued

| Code | Compound | HOMO/eV | LUMO/eV | Band Gap/eV |
|---|---|---|---|---|
| ETS-3 | [structure: anthracene with two thianthrene substituents] | −6.00 | −3.10 | 2.90 |

TABLE 3

Photoluminescence Data

| Code | Compound | PL, ($\lambda_{max}$, Thin film)/nm | PL ($\lambda_{max}$, Powder)/nm | PL ($\lambda_{max}$, in $CH_2Cl_2$)/nm |
|---|---|---|---|---|
| ETS-1 | [structure: thianthrene-anthracene] | 452 | 447 | 417 |
| ETS-2 | [structure: thianthrene-biphenyl] | 412 and 459 | 387, 409, 435 | 356 and 370 |
| ETS-3 | [structure: anthracene with two thianthrene substituents] | 440 and 500 (shoulder) | 441, 508 | 430 |

Example 14

Device Structure

A pre-etched ITO coated glass piece (10×10 cm$^2$) is used. The device is fabricated by sequentially forming layers on the ITO by vacuum evaporation using a Solciet Machine, ULVAC Ltd. Chigasaki, Japan. The active area of each pixel is 3 mm by 3 mm. The coated electrodes are encapsulated in an inert atmosphere (nitrogen) with UV-curable adhesive using a glass backplate. Electroluminescence studies are performed with the ITO electrode always connected to the positive terminal. The current vs. voltage studies are carried out on a computer controlled Keithly 2400 source meter.

Devices with green emitters are formed by the method described above consisting of an anode layer, buffer layer, hole transport layer, electroluminescent layer (doped metal complex), electron transport layer, electron injection layer and cathode layer, film thicknesses being in nm:

ITO/ZnTp TP (20 nm/a-NPB (100 nm)/Alq$_3$:DPQA  
(40 nm:0.1 nm)/Alq$_3$ (20 nm))/Liq(3 nm))/Al    Device 1.

wherein DPQA is diphenylquinacridone.

ITO/ZnTp TP (20 nm/a-NPB (100 nm)/Alq$_3$:DPQA  
(40 nm:0.1 nm)/Alq$_3$:Liq (10 nm:10 nm))/Liq(3 nm))/Al    Device 2.

ITO/ZnTp TP (20 nm/a-NPB (100 nm)/Alq$_3$:DPQA  
(40 nm:0.1 nm)/ETS-001: Liq (15 nm:5 nm))/  
Liq(3 nm))/Al    Device 3.

Figure 15:
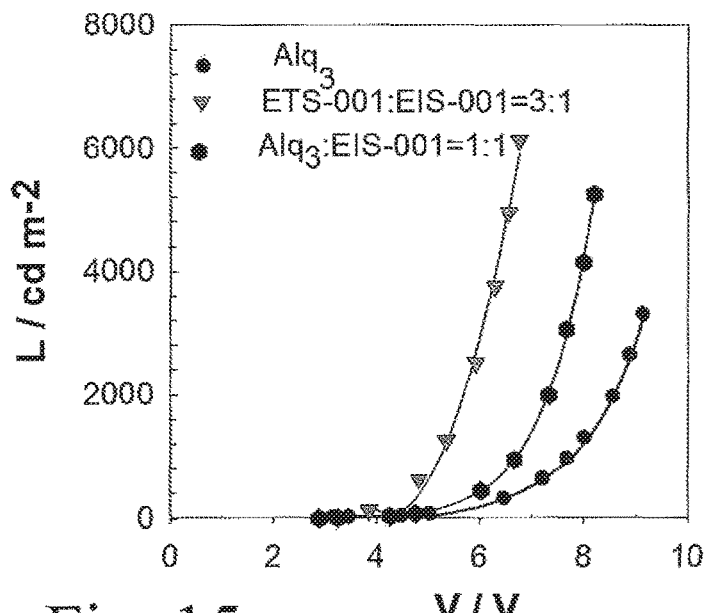
Figure 16:
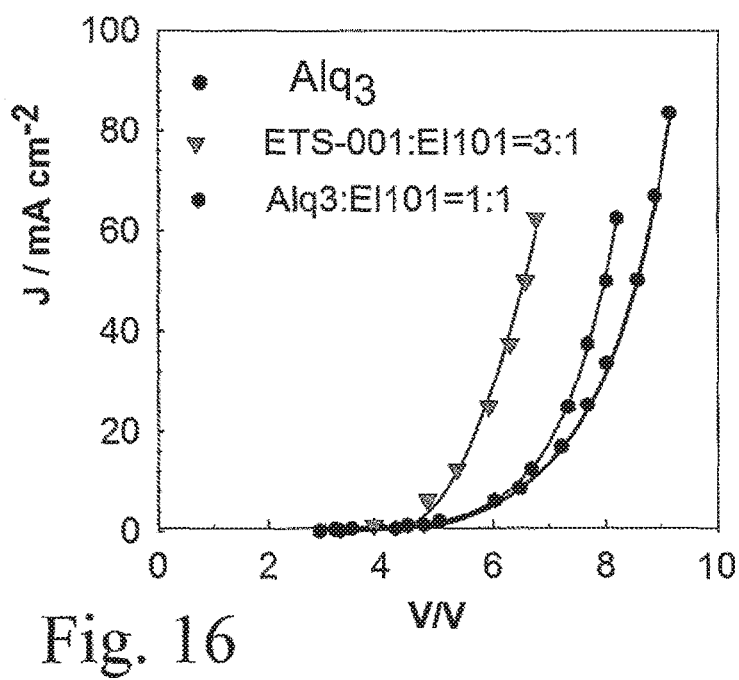
Figure 17:
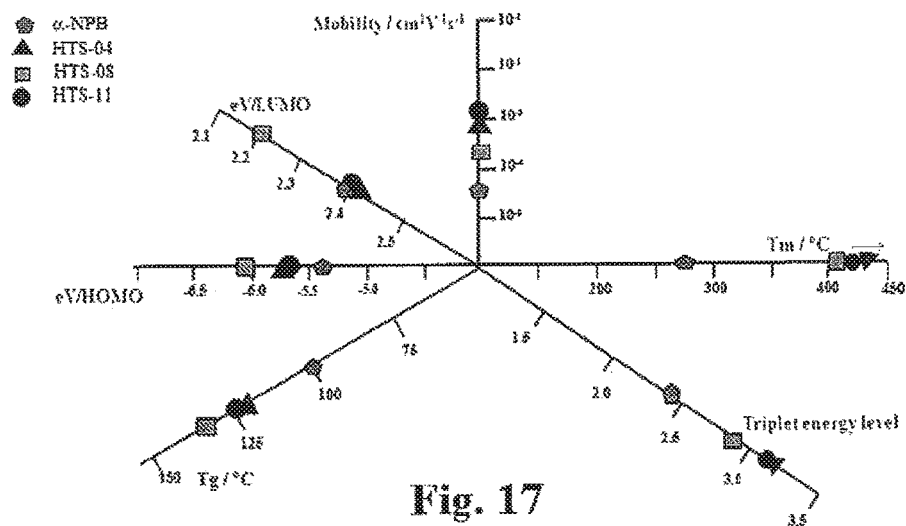
FIG. 17 is a diagram showing plots along variously directed lines of hole mobility, melting point, glass transition temperature, HOMO level and LUMO level for the compounds α-NPB, HTS-4, HTS-8 and HTS-11.
Figure 18:
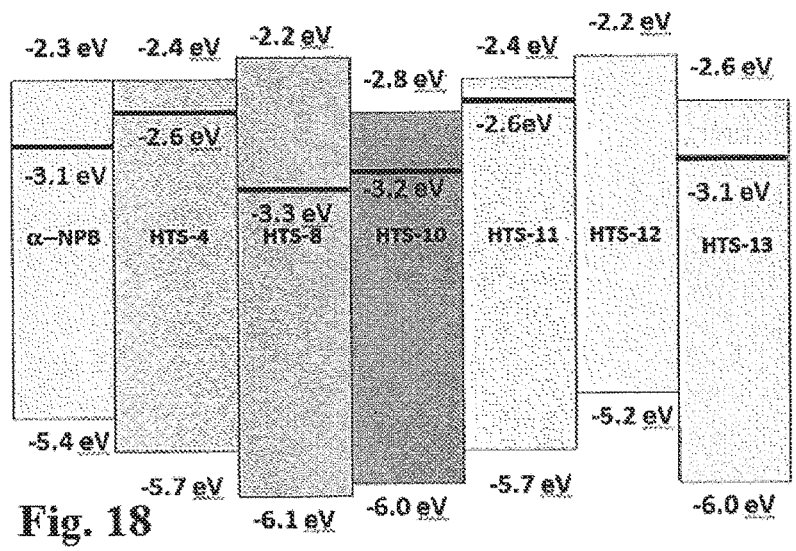
FIG. 18 is a bar chart showing HOMO and LUMO levels for various hole transport compounds.

FIGS. 15 and 16 compare the performance of the devices as far as the current injection characteristics of the different electron transporting layer. Device 2 has Alq$_3$:Liq (1:1) as this is the optimum concentration. The compounds ETS-002 and ETS-003 are expected to give similar performance to ETS-001 although the ratio of ETS-002 or 3 to LiQ dopant may vary from that for ETS-001 and may have to be determined by routine trial and error.

Example 15

2-(4'-diphenylamino)phenyl-8-(1'-Thianthrenyl)-dibenzothiophene (HTS-11)

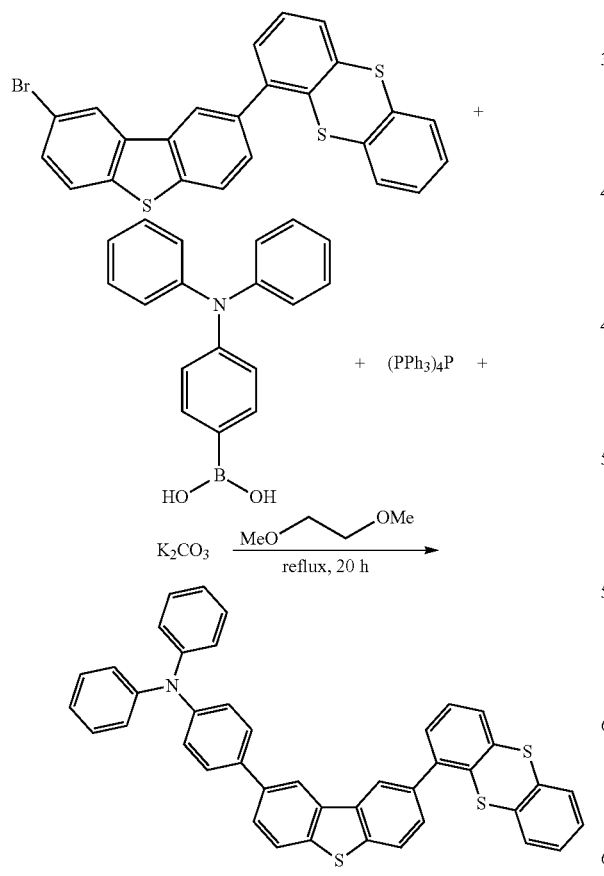

A mixture of 2-bromo-8-(1-thianthrenyl) dibenzothiophene (4.0 g, 8.38 mmole) and tetrakistriphenylphosphinepalladium (0.485 g; 0.420 mmol) was heated in 1,2-dimethoxyethane (50 ml) at about 50° C. for 10 minutes. Then, 4-(diphenylamino)phenylboronic acid (2.2 g; 7.54 mmol) in 1,2-dimethoxyethane (10 ml) was added followed by potassium carbonate (5.8 g; 41.97 mmol) in water (10 ml). The resulting mixture was refluxed under nitrogen for 20 hours. The solvent removed from the cooled reaction mixture and the residue dissolved in dichloromethane and washed with water. The organic phase again washed with brine and dried over anhydrous magnesium sulphate and solvent removed to give the crude product. This was subjected to column chromatography over silica gel using CH$_2$Cl$_2$-Petroleum ether (40-60° C.). The eluent containing the product was evaporated using rotary evaporator and the residue was magnetically stirred with methanol overnight to give a fluorescent white solid, 3.3 g (61%). The product was further purified by sublimation at 355° C. and 2.0×10$^{-6}$ Torr to give colourless glassy solid, 1.3 g, sublimation yield of around 40%. The product did not show any melting peak in the DSC, but showed a Tg at 124° C.

Found: C, 79.37, H, 3.67, N, 2.45, S, 16.04%, also obtained C, 77.52, H, 4.13, N, 1.89 and S, 16.04%.

C$_{42}$H$_{27}$NS$_3$, requires C, 78.59, H, 4.24, N, 2.18 and S, 14.99%.

UV: $\lambda_{max}$ (CH$_2$Cl$_2$)/nm (s/dm$^3$ mol$^{-1}$ cm$^{-1}$) 338 (25,536) 291 sh (30,643) and 261 (72,321).

$\lambda_{max}$ (Thin film)/nm: 336 sh, 291 (sh) and 261 nm.

Optical band gap: 3.26 eV.

FL: $\lambda_{max}$/nm (CH$_2$Cl$_2$) em: 413; ex/nm: 300; $\lambda_{max}$/nm (Powder) em: 419, ex/nm: 300; $\lambda_{max}$/nm (Thin film) em: 414, ex/nm: 300.

TGA/° C. (% weight loss): 461 (1%) and 509 (5).

HOMO −5.67 eV, LUMO −2.4 eV.

Example 16

4-(1-thianthrenyl)-bis(triphenyl amine) [HTS-13]

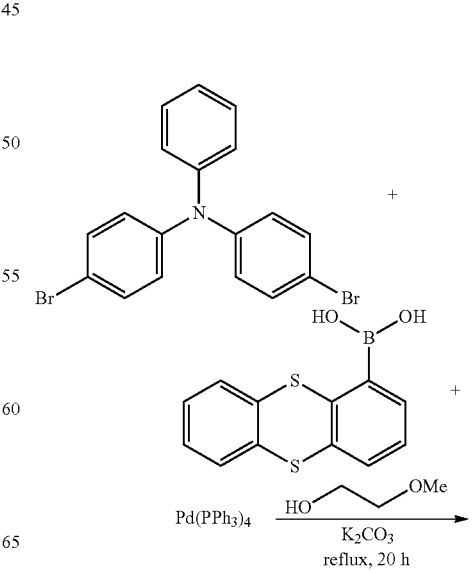

-continued

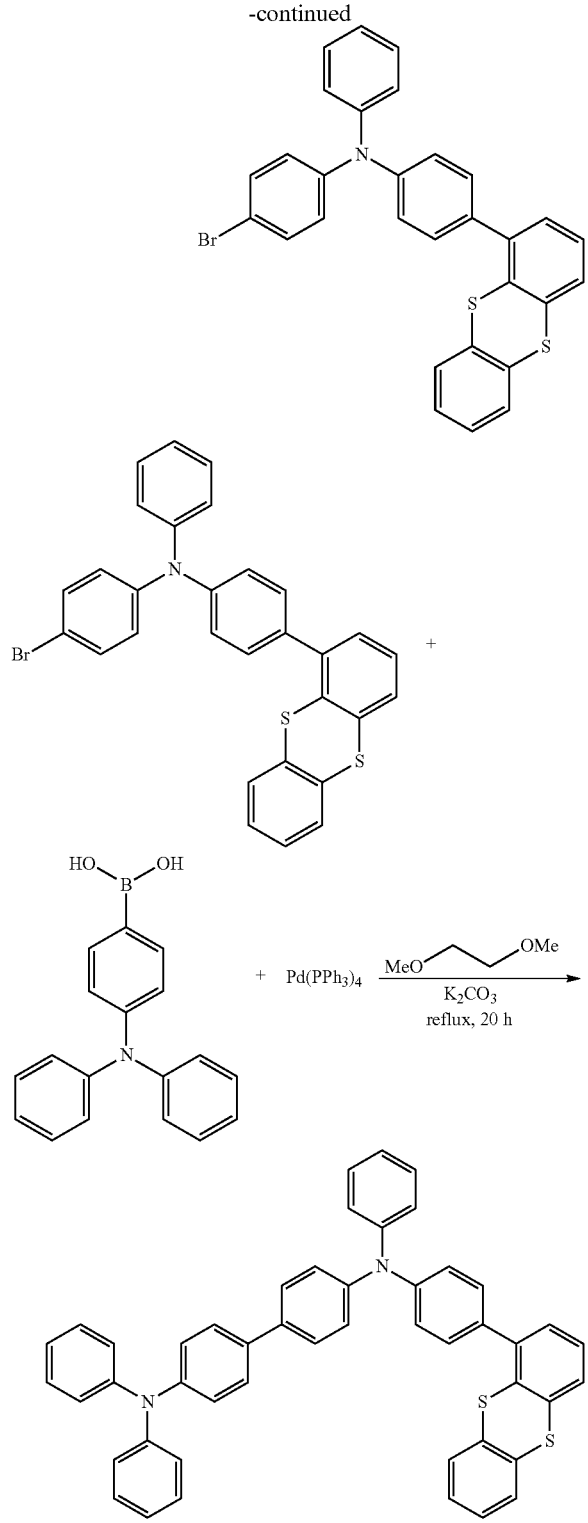

(a) To a slurry of 4,4'-dibromotriphenylamine (5.3 g; 0.013 mole) in 2-methoxyethanol (50 ml) was added tetrakis (triphenylphosphine) palladium (0.76 g; 0.00066 mole) followed by 1-thianthrenylboronic acid (3.42 g; 0.013 mole) in 2-methoxy ethanol (30 ml). Then sodium tert-butoxide (2.4 g; 0.025 mole) was added followed by 2-methoxy ethanol (20 ml). The reaction mixture was refluxed under nitrogen for 20 hrs. The solution at the beginning became homogeneous then cloudy finally dark green in colour. The solvent removed under reduced pressure using the rotary evaporator and the residue extracted with dichloromethane. The dichloromethane solution was washed with brine and water then dried over anhydrous magnesium sulphate. The solvent after filtration of magnesium sulphate was evaporated in a rotary evaporator to give dark green solid. The solid was purified by column chromatography using petroleum ether-dichloromethane (3:2) to give a colourless solid, 3.4 g (48%).

(b) 4-Bromo-4'-(1-thianthrenyl)triphenyl amine (3.3 g; 0.0061 mole) was taken-up in dimethoxy ethane (40 ml) and warmed at about 50° C. for 10 min, then $(PPh_3)_4Pd$ (0.75 g; 0.00065 mole) was added followed by toluene (20 ml). A clear solution was obtained but within 10 min it became dark in colour. 4-(diphenylamino)phenylboronic acid (1.60 g; 0.0055 mole) in toluene (20 ml) was added followed by potassium carbonate 92.6 g; 0.018 mole) in water (10 ml). The reaction mixture magnetically stirred and refluxed for 20 hrs. The solvent removed from the reaction mixture using rotary evaporator and the residue was dissolved in dichloromethane, washed with water twice and dried over anhydrous magnesium sulphate. The solvent filtered from magnesium sulphate and removed using rotary evaporator to give the crude product. The product was subjected to flash chromatography using $CH_2Cl_2$-Petroleum ether (40-60° C.) [1:1] to give the product as viscous liquid. This was cooled and magnetically stirred with methanol and small amounts of petroleum ether (40-60° C.) to give an amorphous white solid. The solid was filtered off and dried under vacuum at 80° C. to give 3.1 g of product (72%). The product was further purified by sublimation at 280° C. (4.8×10-7 Torr) to give a glassy solid 1.3 g (42%). The compound did not show any melting peak in DSC, but showed a glass transition temperature (Tg) at 107° C.

Found: C, 81.20, H, 4.80, N, 3.93, S, 10.16%.

$C_{48}H_{34}N_2S_2$ requires, C, 82.02, H, 4.88, N, 3.98 and S, 9.12%.

UV: $\lambda_{max}$ (Toluene)/nm (s/dm$^3$ mol$^{-1}$ cm$^{-1}$) 324.50 (36, 506).

$\lambda_{max}$ (Thin film)/nm: 324.50 and 265.50 nm.

Optical band gap: 3.1 eV.

FL: $\lambda_{max}$/nm (toluene) em: 394 and 410 (sh); ex/nm: 320; $\lambda_{max}$/nm (Powder) em: 427, ex/nm: 320; λmax/nm (Thin film) em: 428 and 410 (sh), ex/nm: 320.

TGA/° C. (% weight loss): 382 (5) and Td at 498° C.

Example 17

Efficiency of OLED Devices

OLEDS were fabricated using as hole transport layers α-NPB, HTS-8 and HTS-11. The layers were as follows (HIL means hole injection layer, HTL means hole transport layer, EML means emissive layer and ETL means electron transport layer):

Anode: ITO on glass
HIL: PEDOT:PSS ~40 nm, spin coated
HTL NPB (50 nm), HTS-8 (10-22 nm) or HTS-11 (10-30 nm)
EML: TCTA:TPBi (3:7): Ir(ppy)2acac, doping 10%
ETL: TPBi (30 nm)
Cathode: LiF (0.5 nm)/Al (100 nm)

In the above listing PEDOT means poly(3,4-ethylenedioxythiophene) and PSS means poly(4-styrenesulfonate), TCTA means tris(4-carbazoyl-9-ylphenylamine) and TPBi means 1,3,5-tris(N-phenylbenzimidizol-2-yl)benzene. The PEDOT:PSS is spin coated and the HTS-8 is also spin coated in chlorobenzene. Device performance for various cells is shown below:

| HTS | | $V_T$/V (Turn-on voltage) | $V_D$/V @1000 nits | Maximum | | @1000 cd m$^{-2}$ | | @10000 cd m$^{-2}$ | |
|---|---|---|---|---|---|---|---|---|---|
| | | | | C/E (cd/A) | P/E (lm/W) | C/E (cd/A) | P/E (lm/W) | C/E (cd/a) | P/E (lm/W) |
| a-NPB (50 nm) | a | 2.69 | 4.28 | 52.68 | 51.13 | 52.23 | 38.32 | 36.80 | 16.79 |
| a-NPB (50 nm) | b | 2.48 | 4.66 | 58.93 | 68.07 | 47.02 | 31.70 | 35.89 | 18.93 |
| HTS-04 (10 nm) | a | 3.06 | 4.88 | 54.72 | 52.41 | 54.34 | 34.97 | 48.65 | 24.28 |
| HTS-04 (50 nm) | a | 3.23 | 5.35 | 58.98 | 51.46 | 56.09 | 32.96 | 45.31 | 19.02 |
| HTS-11 (10 nm) | b | 2.65 | 4.11 | 70.75 | 69.29 | 68.95 | 52.71 | 58.81 | 29.07 |
| HTS-11 (30 nm) | b | 2.96 | 4.56 | 68.27 | 62.12 | 67.00 | 46.24 | 60.37 | 32.48 |
| HTS-08* (10 nm) | b | 3.01 | 4.75 | 40.66 | 25.85 | 38.92 | 25.73 | 36.49 | 15.77 |
| HTS-08* (20 nm) | b | 3.12 | 6.45 | 48.43 | 30.91 | 45.84 | 22.31 | 36.72 | 14.44 |

*Spin coated (Chlorobenzene) film.
a) ITO/PEDOT:PSS(50 nm)/HTS-04/CBP:Ir(ppy)$_3$(12%)(20 nm)/TPBi(40 nm)/LiF(1 nm)/Al
b) ITO/PEDOT:PSS(40 nm)/HTS/TCTA:TPBi(3:7):Ir(ppy)$_2$acac(10%)(Total thickness 20 nm)/TPBI(30 nm)/LiF(0.5 nm)/Al.

Figure 19:
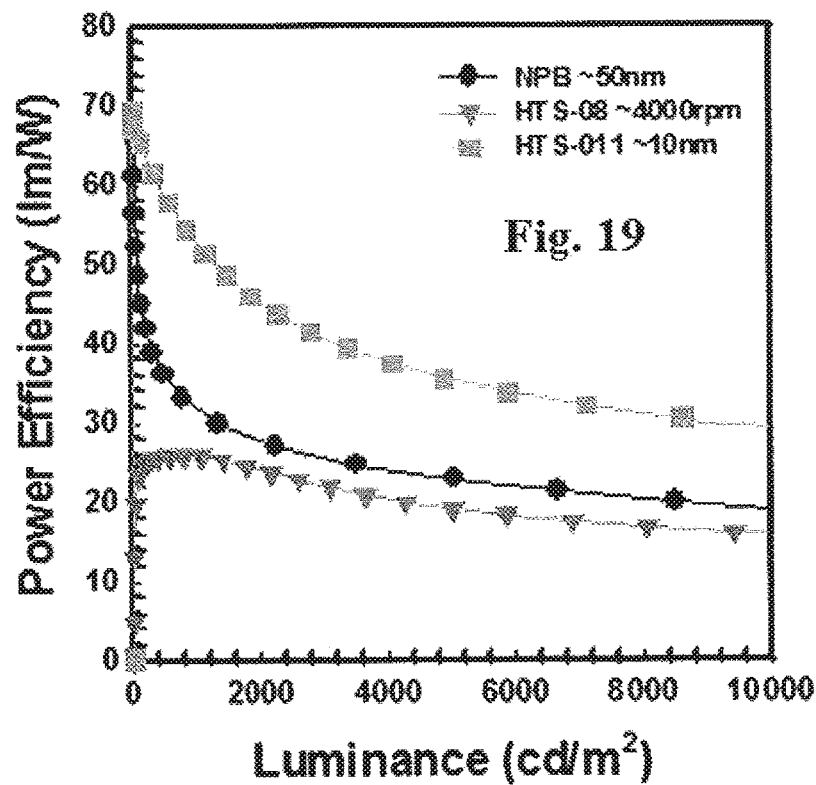
FIG. 19 shows luminous efficiency for various OLED devices.
Figure 20:
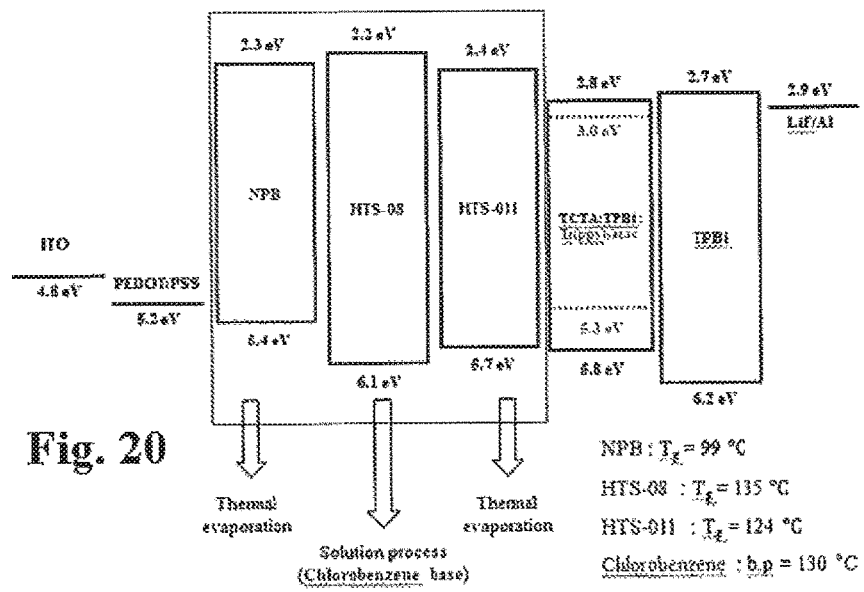
FIG. 20 is an energy band diagram for the OLED device of Example 17.
Figure 21:
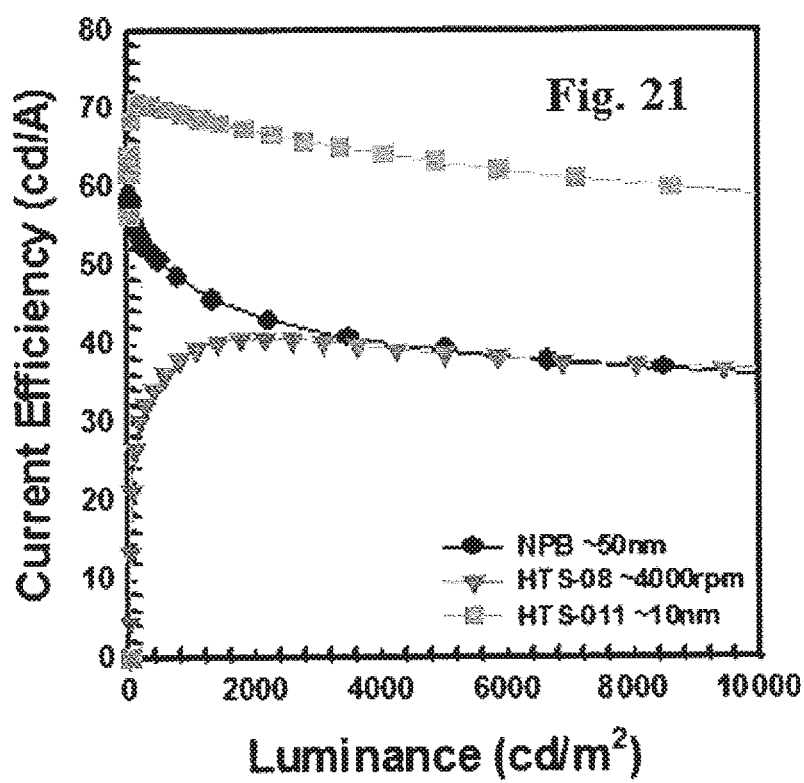
FIG. 21 shows current efficiency against luminance for various OLED devices.
Figure 22:
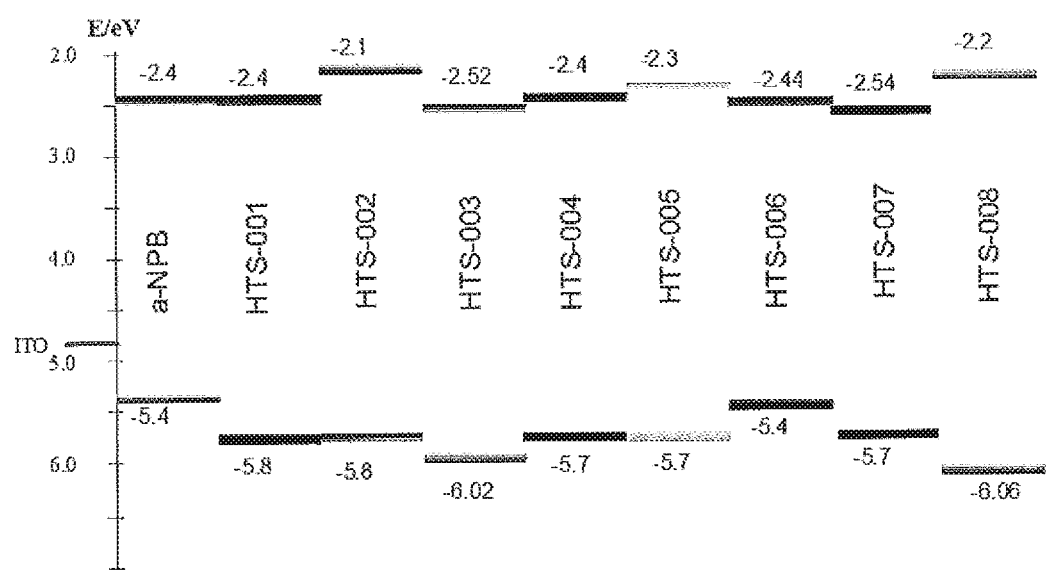
FIG. 22 is a bar chart showing HOMO and LUMO levels for α-NBP and for compounds HTS-001 to HTS-008.

The cells provide green emission. Efficiency in a representative cell is shown in FIG. 19 and is in the order HTS-11>HTS-8>α-NPB and an energy band diagram for the cell appears as FIG. 20. A plot of current efficiency against luminance appears as FIG. 21.

It will be appreciated that compounds of the invention are industrially applicable. They may find use in applications in OLED displays such as microdisplays, mobile displays and TV (2-D) and TV (3-D), in OLED lighting, in devices comprising quantum dots, in light sources for light activated printing, in OLED devices where a combination of fluorescent or phosphorescent or rare earth or quantum dot emitters are employed. Devices incorporating the present compounds may be made by vacuum thermal evaporation, solution based printing (spin coating, inkjet printing), OVPD (organic vapour phase deposition) etc. OLED devices incorporating compounds of the invention may employ a combination of fluorescent or phosphorescent or rare earth or quantum dot emitters are employed. The invention also covers a mixture of hole transporters including at least one compound according to the invention and hole transporters according to the invention doped with acceptors.

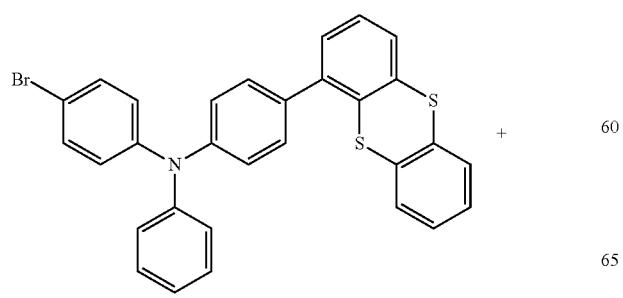

+

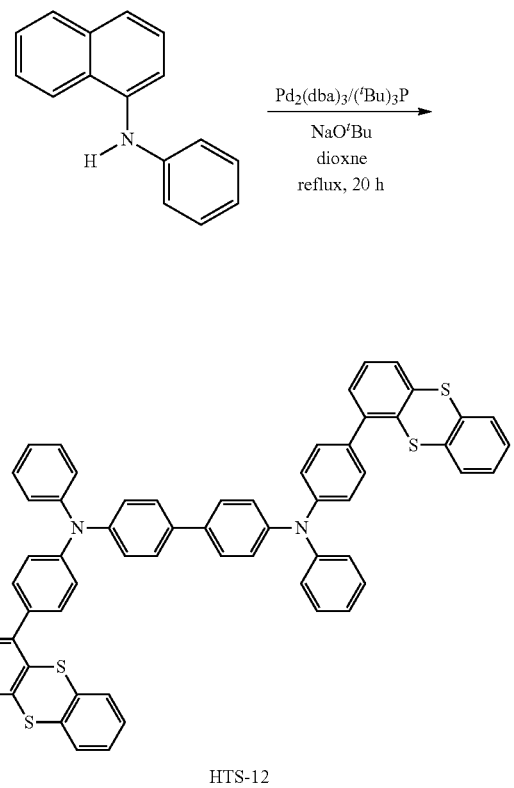

HTS-12

Synthesis of the indicated compound was attempted from the 4-Bromo-4'-(1-thianthrenyl)-triphenylamine with N-phenyl-N-(1-napthyl) amine by Hartwig-Buchwald coupling reaction as outlined in the scheme below.

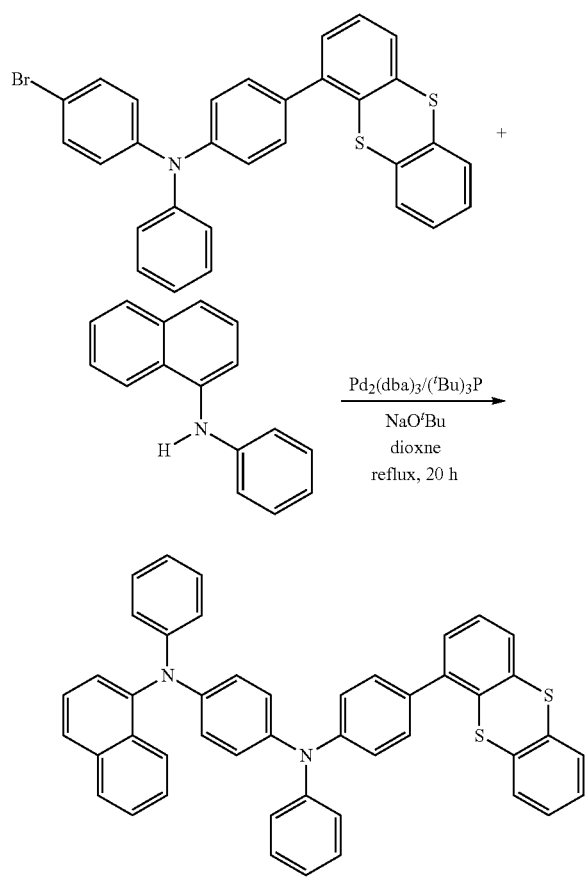

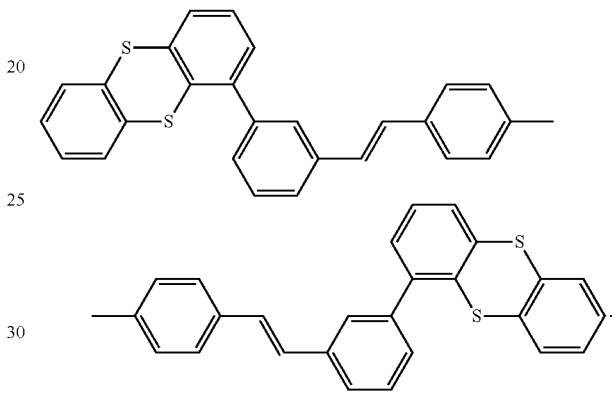

The reaction was carried out in refluxing dioxane (20 h) using tris(dibenzylideneacetone) dipalladium as catalyst, tris(tert-butylphosphine) as the ligand and sodium tert-butoxide as base. After usual work-up the product was extracted into dichloromethane. Preliminary TLC examination of the crude product showed three spots. Therefore it was subjected to flash column chromatography over silica gel under nitrogen using $CH_2Cl_2$-Petroleum ether (40-60° C.) [1:4] as eluent. The more polar fraction was isolated and obtained as a white solid by trituration with methanol. The solid was further purified by sublimation at 40° C. and $5\times10^{-7}$ Torr pressure to give a colourless solid in small amounts. The base peak (100%) of high resolution mass spectrum at 916.2074 ($C_{60}H_{40}N_2S_2$) and the elemental analysis indicates the compound is a dimer of the structure as shown above.

Found: C, 78.21, H, 4.42 and N, 2.91%.
$C_{60}H_{40}N_2S_2$ requires C, 78.40, H, 4.61 and N, 3.05%.

Thermogravimetric analysis under nitrogen of the dimeric compound HTS-12-dimer showed a 5% weight loss at 513° C. It also showed a weight increase of 3.8% at 396° C. which may be attributed to nitrogen adsorption by the compound. The UV spectrum has similar low energy absorption at wave length 343 nm, whereas fluorescent emissions have a red shift from the dichloromethane solution at 413 nm to 428 nm as thin film and at 440 nm as powder. The compound has a glass transition temperature Tg of 142° C., a decomposition temperature of 550° C., a band gap of 3.0 eV, a HOMO level of −5.2 eV and a LUMO level of −2.2 eV and a triplet level of −2.8 eV.

The invention claimed is:

1. Bis [3-(phenylvinyl-1-thianthrenyl)]-4,4'-biphenyl

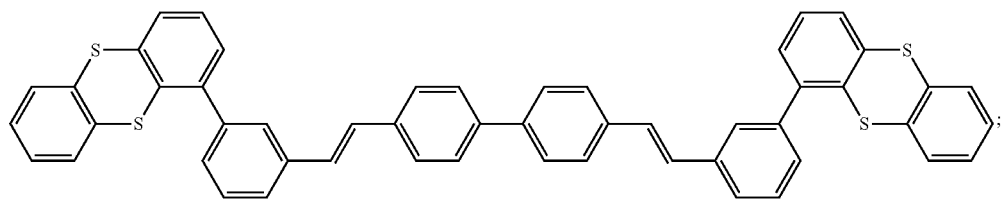 [SMILES: C(=C\c1cccc(-c2cccc3c2Sc2ccccc2S3)c1)/c1ccc(-c2ccc(/C=C/c3cccc(-c4cccc5c4Sc4ccccc4S5)c3)cc2)cc1]

2. 2-(4'-Diphenylamino)phenyl-8-(1'-thianthrenyl)-dibenzothiophene.

3. Either compound of the following structure:
   (a) bis [3-(phenylvinyl-1-thianthrenyl)]-4,4'-biphenyl
   (b) 2-(4'-Diphenylamino)phenyl-8-(1'-thianthrenyl)-dibenzothiophene.

4. A hole transport material comprising a compound according to claim 3 and a p-dopant which is an acceptor-type organic molecule.

5. The material of claim 4, wherein the dopant is present in an amount such that when the material is deposited to form a layer the dopant contributes about 10-40% to layer thickness.

6. The material of claim 5, wherein:
   (a) the dopant comprises tetracyanoquinodimethane or tetrafluorotetracyano-quinodimethane;
   (b) the dopant comprises a compound of any of the general formulae (i)-(vii) below:

93
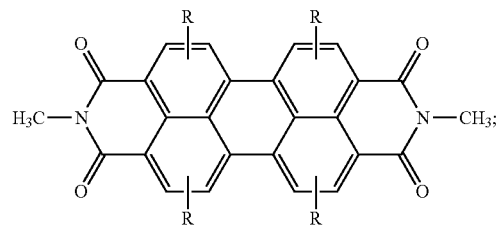
94
(i)
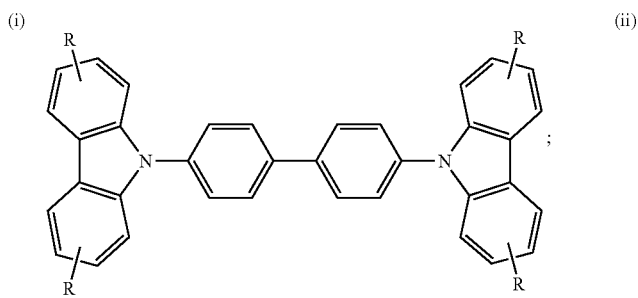
(ii)
(iii)
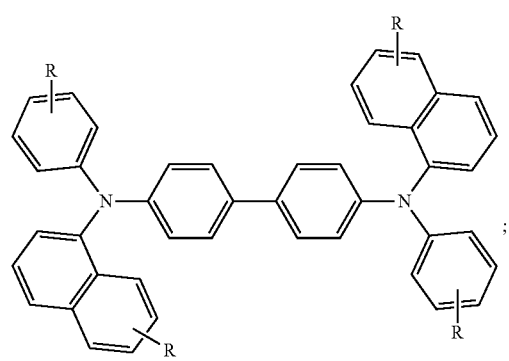
(iv)
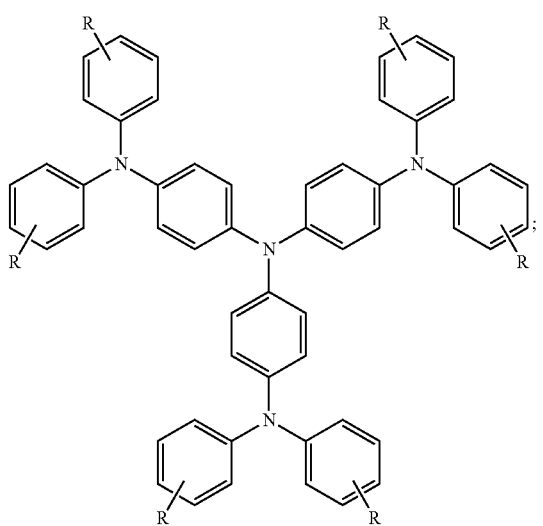
(v)
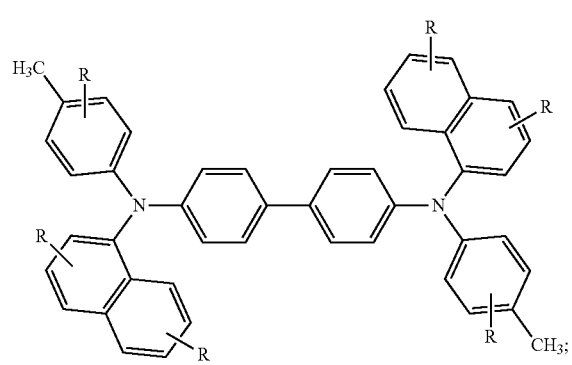
(vi)
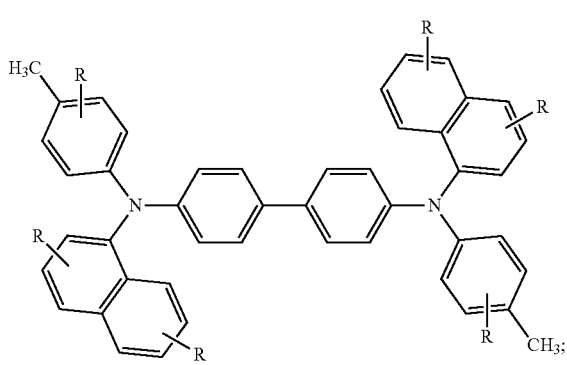
(vii)
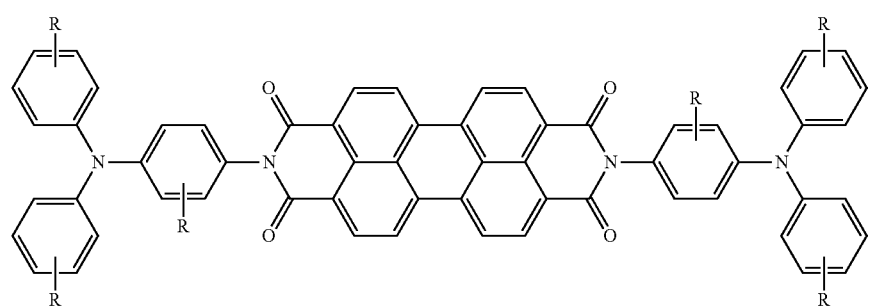

wherein the groups R in any of the formulae in (i) to (vii) can be the same or different and are selected from hydrogen; substituted and unsubstituted aliphatic groups; substituted and unsubstituted aromatic, heterocyclic and polycyclic ring structures; halogens; and thiophenyl groups; and wherein in formula (i) the methyl groups may be replaced by $C_1$-$C_4$ alkyl or monocyclic or polyclic aryl or heteroraryl which may be further substituted e.g. with alkyl, aryl or arylamino, or of the formula viii or ix

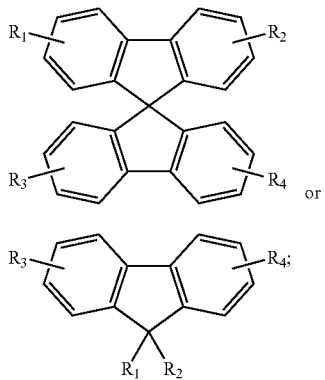

viii or ix wherein the groups $R_1$-$R_4$ when appearing in either of the above formulae can be the same or different and are selected from hydrogen; substituted and unsubstituted aliphatic groups; substituted and unsubstituted aromatic, heterocyclic and polycyclic ring structures; halogens; and thiophenyl groups;

(c) the dopant comprises a teritiary amine which is α-NPB or β-NBP.

7. An optical light-emitting diode having first and second electrodes and between said electrodes a layer comprising a compound as claimed in claim 3.

8. The diode of claim 7, wherein said layer is a hole transport layer or a hole injection layer.

9. The diode of claim 7, having an emissive layer comprising an emitter selected from:
   (a) a fluorescent emitter;
   (b) a phosphorescent emitter;
   (c) an ion fluorescent (rare earth based) emitter;
   (d) quantum dots; and
   (e) thermally activated fluorescent (TADF) materials.

10. The diode of claim 7, having a hole injection layer comprising CuPC, ZnTpTP, 2-TNATA or

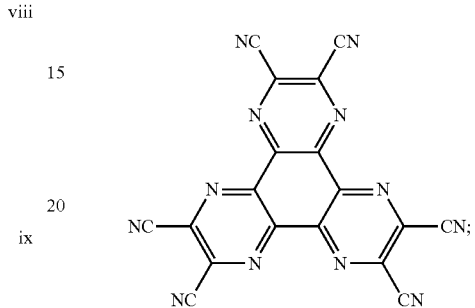

11. The diode of claim 7, which forms part of a flat panel display, a lighting panel, r an organic photovoltaic device.

12. An imaging member for forming an electrostatic latent image, an organic thin film transistor, a dye-sensitised solar cell, a printed device or a quantum dot based electroluminescent device comprising a compound as claimed in claim 3.

13. An OLED device used as a light source to print conductive, resistive, dielectric, piezoelectric or pyroelectric films or lines or grids said device comprising a compound as claimed in claim 3.

14. An OLED lighting panel comprising a compound as claimed in claim 3.

* * * * *